United States Patent
Gonçalves et al.

(10) Patent No.: US 9,487,773 B2
(45) Date of Patent: Nov. 8, 2016

(54) CELL-BASED METHODS FOR COUPLING PROTEIN INTERACTIONS AND BINDING MOLECULE SELECTION

(71) Applicant: TECHNOPHAGE, INVESTIGAçÂO E DESENVOLVIMENTO EM BIOTECNOLOGIA, SA, Lisbon (PT)

(72) Inventors: João Manuel Braz Gonçalves, Lisbon (PT); Frederico Nuno Castanheira Aires da Silva, Lisbon (PT); Sofia Volker Côrte-Real, Cruz Quebrada (PT); Soraia Rafaela Santiago de Oliveira, Lisbon (PT)

(73) Assignee: TECHNOPHAGE, INVESTIGACAO E DESENVOLVIMENTO EM BIOTECNOLOGIA, SA, Lisbon (PT)

( * ) Notice: Subject to any disclaimer, the term of this patent is extended or adjusted under 35 U.S.C. 154(b) by 0 days.

(21) Appl. No.: 14/193,679

(22) Filed: Feb. 28, 2014

(65) Prior Publication Data

US 2014/0249044 A1 Sep. 4, 2014

Related U.S. Application Data

(60) Provisional application No. 61/771,562, filed on Mar. 1, 2013.

(51) Int. Cl.
*C12N 15/10* (2006.01)
*G01N 33/537* (2006.01)
*G01N 33/566* (2006.01)

(52) U.S. Cl.
CPC ....... *C12N 15/1037* (2013.01); *C12N 15/1024* (2013.01); *C12N 15/1055* (2013.01); *G01N 33/537* (2013.01); *G01N 33/566* (2013.01); *G01N 2500/02* (2013.01); *G01N 2500/10* (2013.01)

(58) Field of Classification Search
CPC ............... G01N 33/57; G01N 33/566; G01N 2500/02; G01N 2500/103; C12N 15/1024; C12N 15/1037; C12N 15/1055
See application file for complete search history.

(56) References Cited

PUBLICATIONS

Leskela et al., "Opioid Receptor Pharmacological Chaperones Act by Binding and Stabilizing Newly Synthesized Receptors in the Endoplasmic Reticulum," J. of Biological Chemistry, vol. 282, No. 32, pp. 23171-23183, 2007.
Technophage, Investigação E Desenvolvimento Em Biotecnologia, SA, International Search Report for PCT/PT2014/000016; 6 pages, Jan. 5, 2015.

*Primary Examiner* — Robert Landsman
(74) *Attorney, Agent, or Firm* — Margaret B. Brivanlou; King & Spalding LLP

(57) ABSTRACT

The invention relates to cell-based methods for diversifying, expressing and selecting binding molecules, e.g., antibodies, and target molecules to which they bind, all of which are expressed in the same cell. The target molecule can be a member of a ligand binding pair comprising a cell-surface expressed ligand binding receptor molecule and its cognate ligand, which interact within the cell. The methods provide retaining either the antibody or its target in a cell organelle as the site of binding and interaction. By performance of the methods, the binding or non-binding of the antibody to its target molecule within the cell produces a cell phenotype that is detectable at the cell surface via high throughput assays, e.g., flow cytometry. The methods are particularly useful for generating, recovering and providing antibodies that have optimal target molecule binding properties or activities for potential therapeutic use. Methods for generating diversity in such antibodies are also provided.

56 Claims, 8 Drawing Sheets

Localization of zinc-finger target sites into light-chain and heavy-chain encompassing all three reading frames

A

B

CELL-BASED METHODS FOR COUPLING PROTEIN INTERACTIONS AND BINDING MOLECULE SELECTION

PRIORITY

This application claims the benefit of U.S. Provisional Patent Application No. 61/771,562, filed on Mar. 1, 2013, the contents of which are hereby incorporated by reference in their entirety.

SEQUENCE LISTING

This application contains a Sequence Listing which has been submitted electronically in ASCII format and is hereby incorporated by reference in its entirety. The ASCII copy of the Sequence Listing, created on Feb. 28, 2014, is named 14116-105012_SL.txt and is 19,349 bytes in size.

FIELD OF INVENTION

The present invention relates generally to methods of selecting a binding molecule, such as an antibody, in a cellular environment, wherein the binding molecule specifically binds to a target molecule, such as a ligand binding protein or its cognate ligand, as well as to methods of generating genetic diversity in one or more binding molecules, such as antibodies or functional portions thereof, having specificity for a particular target molecule, e.g., a protein or antigen, and having the potential for improved binding and/or functional properties or activities.

BACKGROUND OF THE INVENTION

Since the discovery of hybridoma technology in 1975 and with the subsequent development of recombinant DNA technologies, the genes encoding binding proteins, particularly antibodies, have been engineered to manipulate the binding protein or antibody in some way, e.g., reduction in size, such as a single-chain variable fragment (scFv) or variable fragments from antibody light chain ($V_L$) and heavy chain ($V_H$); rebuilding into multivalent high-avidity reagents; and fusion with a variety of molecules (e.g. enzymes, toxins). In addition, several selection methods and experimental approaches have been developed in order to select monoclonal antibodies (mAbs) with higher affinity and specificity.

Antibody selection techniques using an antibody library can be performed totally in vitro, without the requirement of cell transformation, or in vivo, in which cells may be transformed, e.g., using vectors encoding an antibody library. In vitro antibody selection includes techniques such as ribosome, RNA and DNA display, while in vivo antibody selection includes techniques such as phage-display, two-hybrid systems, cell-display, e.g., in bacteria, yeast, or mammalian cells and protein fragment complementation assays (PCA). Phage-display is broadly used due to its simplicity, versatility and ability to be adapted to many specific conditions. Yeast, bacterial, and mammalian cell display platforms offer an advantage over phage-display in that fluorescence activated cell sorting (FACS) can be coupled with cell surface antibody display to allow monitoring of both antibody expression on the cell surface and the ability of that antibody to bind to its target. On the other hand, ribosomal display technology allows the screening of larger libraries and facilitates the diversity and efficient antibody maturation in vitro.

Although a large number of antibodies have been selected by various technologies, most need to be affinity improved or enhanced. Such improvement in antibody affinity and subsequent selection of specific antibody are typically achieved through the use of one or more methods, systems, or technologies, such as multimerization of antibodies; *E. coli* mutator strains; B-cell lines, e.g., RAMOS, DT-40, or HEK293T cells and activation-induced cytidine deaminase (AID); retrovirus display systems; error-prone PCR; immunoglobulin chain or CDR shuffling; directed mutagenesis.

Despite the various methodologies developed to improve the affinity and subsequent selection of antibodies, significant problems are prevalent. Examples of problems that have been detected and reported include potency/affinity, expression, correct folding and post-translation modifications of isolated antibodies. Thus improved and new processes are needed for selecting specific and functional antibodies and optimizing them, as well as other types of binding molecules, particularly for therapeutic utility. It is therefore important to develop new strategies related to improved and useful methods for introducing diversification into the genes or nucleic acid sequences encoding binding molecules, such as antibodies, and to provide novel and efficient methods for selecting the expressed molecules, particularly for generating new, improved and useful therapeutic biological products.

SUMMARY OF THE INVENTION

The invention provides an intracellular platform technology and methods for the effective expression and selection of a binding molecule, such as an antibody or immunoglobulin molecule, an antibody mimetic, or other type of recognition/binding molecule, which binds to a specific target molecule, such as a target protein, polypeptide, or peptide, within the environment of a cell. The technology and methods of the invention further provide a means for genetic diversification of the binding molecule, or a fragment or portion thereof, such as an antibody, and its selection following binding to a target molecule within the environment of a single cell. It is to be understood that the term "a cell" as used herein may encompass one cell, or a single cell, in a population of cells or a cell line, or it may encompass a pool, population, or plurality of cells, such as a cell line comprising a plurality of individual cells.

The invention further provides methods for selecting a binding molecule, such as an antibody, by using recombinant technology, cellular machinery and cellular mechanisms for localizing within the cell the target of the binding molecule, for example, a member of a ligand binding pair wherein one member is, for example, a ligand binding protein and the other member is its cognate ligand. In accordance with the methods of the invention, the binding molecule, such as an antibody, specifically binds to its target, which may be either the ligand binding protein, e.g., a receptor protein, or the cognate ligand of the interacting ligand binding pair. In an embodiment, the target is the cognate ligand which is retained in a cell organelle such as the endoplasmic reticulum (ER) or the Golgi. In an embodiment, the target is the receptor protein. In an embodiment, the binding molecule, or a binding portion thereof, is retained in the cell organelle, e.g., the ER or the Golgi. In an embodiment, the binding of the binding molecule, such as an antibody, or a binding portion thereof, to its target disrupts, neutralizes, or blocks the binding or interaction between the ligand binding protein and its cognate ligand, resulting in the appearance on the cell surface of the member of the binding pair not retained or localized in the cell. The disruption or blocking of binding and appearance of binding pair member on the cell surface is indicative of the specific binding activity of the binding molecule, such as an antibody, or a binding portion thereof, to its target and allows for the selection from the cell of the binding molecule as the effector of the disruption, neutralization, or blocking activity, based on the detection of the binding pair member not retained or localized in the cell.

In one of its aspects, the invention provides a selection method employing knockdown expression of cellular receptor proteins, cell-surface membrane-bound proteins, antigens, or ligand proteins by an antibody, or a member of an antibody library, or a functional portion thereof, or by a genetically diversified antibody, or a member of a genetically diversified antibody library, all of which can be co-expressed in the same cell. The expressed cellular receptor proteins, cell surface membrane-bound proteins, or ligand proteins are molecularly engineered to harbor and express retention signal sequences or tags, which allow these proteins to be expressed, for example, as fusion proteins having a retention signal and to be selectively retained in a cell organelle, such as the ER or the Golgi. In an embodiment, one member of an antibody library or one member of a ligand binding molecule library can be co-expressed in the cell with its target molecule, e.g., a cellular receptor protein, a cell-surface membrane-bound protein, or antigen in a cell.

In another of its aspects, the invention provides selection methods which take advantage of specific, and optionally natural, protein-protein interactions within a cell. The proteins can be target antigens that are recognized by a binding molecule such as an antibody, or a binding fragment or portion thereof. Such target antigen interactions include, without limitation, the interaction between a particular cellular receptor protein, or receptor protein capable of being expressed on the plasma membrane surface, with its cognate ligand or protein ("binding pair member"). In the environment of the cell, a target antigen can be bound by a binding molecule such as an antibody, or by a member of an antibody library or a library of other binding molecules, all of which can be co-expressed in the same cell. In an embodiment, within a cell, the binding molecule, e.g., the antibody or a binding portion thereof, binds to either the cellular receptor protein or receptor protein capable of being expressed on the plasma membrane surface as target, or to the cognate ligand or protein as target. This binding by the binding molecule or antibody disrupts, blocks, neutralizes, or inhibits the binding interaction that typically occurs between the cellular receptor protein or receptor protein capable of being expressed on the plasma membrane surface and its cognate ligand or protein. In an embodiment, the binding molecule, antibody, or a binding portion thereof, binds the cognate ligand. In an embodiment, the binding molecule, antibody, or a binding portion thereof, binds the cellular receptor protein or receptor protein.

In another of its aspects, the invention provides a selection method involving the intracellular retention of a ligand binding, or receptor protein, which is normally expressed at the cell surface, by its cognate ligand following the interaction of the receptor protein with its cognate ligand, and the inhibition of the interaction between the receptor protein with its cognate ligand by a binding molecule, or a binding fragment or portion thereof, resulting in the appearance and detection of the receptor protein on the cell surface. The binding molecule, or a binding fragment or portion thereof, can be a member of a binding molecule library, such as an antibody library, or a member of a genetically diversified binding molecule library, such as a diversified antibody library. Within a cell, the antibody, or member of the library, recognizes and binds to either the ligand binding protein or its cognate ligand, all of which are co-expressed in the same cell. In an aspect of the invention, the ligand binding protein or the cognate ligand is retained in the endoplasmic reticulum (ER) of the cell by virtue of operable linkage or fusion to an ER retention signal sequence.

In another aspect, the invention provides a method of molecularly introducing genetic variability and diversification into a binding molecule, in particular, an antibody, or a binding fragment or functional portion thereof, or a library thereof. The diversified binding molecule, antibody, or library thereof can be used in the inventive selection methods described herein so as to select and identify a binding molecule, or a member of a library of binding molecules, having potentially improved or optimal binding of and/or activity toward a target molecule, such as a receptor protein expressed on the cell surface, or the ligand of such a receptor protein. The methods can generate populations of binding molecules, e.g., antibodies, having increased diversity and that can be screened or selected for improved or optimized properties or activities, such as target specificity, binding and/or functional properties.

The methods of selecting binding molecules having specificity for binding target molecules according to the invention are especially conducive for selecting one or more of the genetically diversified antibodies as described herein. In an aspect, genetic variability and diversification of an antibody binding molecule is effected by the introduction of zinc finger protein recognition sites into the complementarity determining regions (CDRs), for example, CDR1 and/or CDR3, of antibody heavy and/or light chain variable regions, i.e., $V_H$ and/or $V_L$, respectively, to generate modified CDRs. Gene disruption is induced by the targeting of recognition sequences molecularly engineered within one or more of the CDRs and is effected by the creation of novel zinc finger nucleases (ZFNs) and their associated cleavage activity. In an embodiment and as described herein, one or more of the CDRs is molecularly engineered to contain one or more zinc finger DNA binding protein recognition sequences as targeting site sequences. In an embodiment, two ZFN cleavage sites comprise each CDR in a $V_H$ or $V_L$ antibody domain. For example, if a $V_L$ region comprises a modified CDR, that CDR is molecularly engineered to contain two zinc finger recognition target sites such that a pair of ZFNs generated according to the invention would cleave at or near the two recognition sites within the CDR.

In another of its aspects, the invention provides a method of selecting a binding molecule which blocks or disrupts an interaction between a cell surface expressed receptor protein and its cognate ligand within a cell, wherein the method comprises expressing in the same cell a receptor protein which is expressible on the surface of the cell; expressing in the cell a cognate ligand of the receptor protein, wherein the cognate ligand is molecularly tagged with a sequence for retaining the ligand in an intracellular organelle under conditions allowing for the retention of the ligand in the organelle and the interaction of the receptor protein and the cognate ligand in the organelle such that the receptor protein would also be retained within the cellular organelle when bound to the tagged ligand; introducing into the cell a binding molecule which specifically binds either the receptor protein or the ligand protein retained in the intracellular organelle as its target antigen; and detecting the level of the receptor protein expressed on the cell surface; wherein, if the binding molecule binds to either the receptor protein or the ligand and blocks or disrupts their interaction in the organelle, the receptor protein thereby transits through the organelle and is expressed and detectable on the cell surface. Accordingly, the binding molecule, which has bound its target antigen, blocks or disrupts the receptor protein and ligand interaction and is selectable from the cell following detection of the presence of receptor protein on the cell surface, e.g., by a detectable label binding, flow cytometry and growth expansion of the cells. In embodiments, the retention occurs in the ER or the Golgi.

In another of its aspects, the invention provides a method of detecting whether a binding molecule, or a binding fragment or portion thereof, e.g., an antibody, or a binding portion thereof, specifically binds to a cell surface expressed target protein within a cell, wherein the method comprises expressing in a cell a target protein which is expressible on the surface of the cell; expressing in the cell the binding molecule, or a binding fragment or portion thereof, which is molecularly fused or coupled to a sequence for retaining the binding molecule in an intracellular organelle, e.g., the ER or Golgi. Accordingly, if the binding molecule, or a binding fragment or portion thereof, specifically binds to the target protein in the cell, the target protein is retained in the intracellular organelle via its being bound by the binding molecule, or the binding fragment or portion thereof, which is retained in the organelle by virtue of its fusion to the retention signal, thereby preventing expression of the target protein on the cell surface. The level or amount of the target protein expressed on the cell surface is detectable, e.g., via suitable detection methods like flow cytometry, such that a virtually non-detectable or low level of the target protein detected on the cell surface relative to a suitable control indicates binding of the binding protein, or a binding fragment or portion thereof, to the target molecule inside the cell.

In an embodiment of the above-described methods, the selected binding molecule, or a binding portion thereof, can be recovered or isolated from the cell. In another embodiment, the binding molecule is selected from an antibody, or a binding fragment or portion thereof, a member of an antibody library, or a member of a single domain antibody library, e.g., $V_L$ and/or $V_H$ domains. Such antibodies or libraries may be genetically diversified. In another embodiment, the antibody, or a binding fragment or portion thereof, is selected from a polyclonal antibody, a monoclonal antibody, a chimeric antibody, a humanized antibody, a fully human antibody, a single chain antibody (Fv), or a diabody. In another embodiment, the binding fragment or portion is selected from an Fab fragment, an Fab' fragment, an F(ab')2 fragment, an Fd fragment, an Fv fragment, a single-chain variable fragment (scFv), a domain antibody (dAb), a heavy chain variable domain ($V_H$), a light chain variable domain ($V_L$), or a complementarity determining region (CDR). In an embodiment, the binding molecule is an antibody, or a binding fragment or portion thereof, directed against a ligand binding receptor molecule or receptor protein, e.g., human tumor necrosis factor alpha (hTNF-α receptor 1) receptor protein. In an embodiment, the ligand binding receptor molecule or receptor protein is expressible and/or is expressed on the surface of a cell. In an embodiment, the binding molecule is an antibody, or a binding fragment or portion thereof, directed against a cognate ligand (or ligand protein) of the ligand binding receptor protein or receptor protein, e.g., human tumor necrosis factor alpha (hTNF-α). In another embodiment, the binding molecule is a non antibody molecule. In another embodiment, the receptor protein or target molecule is a human receptor protein selected from growth factor receptors, hormone receptors, enzyme receptors, Fc receptors, metabolic enzyme receptors, neurotransmitter receptors, chemokine receptors, cytokine receptors, lymphokine receptors, interleukin receptors, tumor antigen receptors, tumor suppressor antigen receptors (e.g., p53, Rb, k-Rev, DCC receptors), multidrug resistance protein receptors, coagulation factor receptors, Factor VII receptor, Factor VIII receptor, Factor IX receptor, trophic factor receptors, cell recognition or stimulatory molecule receptors, apolipoprotein receptors, EGFR, ErbB-1R, HER1, HER2, aFGFR, bFGFR, NGFR, VEGFR, FltR, TGFR, TGFR-α-1, TGFR-β, TNFR (α), BDNFR, insulin receptor, insulin-like growth factor receptor (IGFR), PDGFR, HGFR, TRKR, BDNFR, CNTFR, GMFR, NT3R, NT5R, HARPR/pleiotrophinR, TIE receptors, Eph receptors, DDR receptors, ROR receptors, LTK receptors, AXL receptors, RET receptors, TOLL-like receptors; hormone receptors selected from steroid hormone receptors, thyroid hormone receptors, melatonin receptors; adrenergic receptors; peptide receptors selected from receptors for amylin, angiotensinogen, angiotensin, atrial natriuretic peptide, brain natriuretic peptide, calcitonin, corticotropin, erythropoietin, endothelin, enkephalin, follicle stimulating hormone, gastrin, ghrelin, glucagon, human chorionic gonadotropin, inhibin, leptin, luteinizing hormone, melanocyte stimulating hormone, oxitocin, pancreatic polypeptide, parathyroid hormone, prolactin, prolactin releasing hormone, rennin, secretin, somatostatin, thrombopoietin, thyroid stimulating hormone, thyrotropin releasing hormone; GP130 or IL6 receptors. In an exemplary embodiment, the receptor protein is human tumor necrosis factor alpha receptor 1 (hTNF-α receptor 1). In another embodiment, the ligand protein or target molecule is a human ligand protein that is a cognate ligand for one of the aforementioned types of receptor molecules. In another exemplary embodiment, the ligand protein or target protein is human tumor necrosis factor alpha (hTNF-α). In another embodiment, the binding molecule binds to one of the receptor protein, or the cognate ligand as the target protein. In another embodiment, the intracellular organelle is the endoplasmic reticulum (ER) or the Golgi. In another embodiment, the cognate ligand is molecularly tagged with a sequence for retaining the ligand in the endoplasmic reticulum (ER). In another embodiment, the ER retention sequence is KDEL (SEQ ID NO:1).

In another aspect, the invention provides a method of detecting whether an antibody, or a binding fragment or portion thereof, specifically binds to a cell surface expressed target molecule within a cell, wherein the method comprises expressing in a cell a target molecule which is expressible on the surface of the cell; expressing in the cell an antibody, or a binding fragment or portion thereof, fused to an ER or Golgi retention sequence; wherein, if the antibody, or a binding fragment or portion thereof, specifically binds to the target protein in the cell, the target protein is retained in the ER or Golgi via its being bound to the antibody, or a binding fragment or portion thereof, thereby preventing expression of the target protein on the cell surface; and detecting the level of the target protein expressed on the cell surface, such that a non-detectable or low level of the target protein detected on the cell surface, relative to a suitable control, indicates binding of the antibody, or the binding fragment or portion thereof, to the target molecule in the cell. The antibody, or a binding fragment thereof, is selectable from within the cell via methods known to the skilled practitioner.

In another of its aspects, the invention provides a method of selecting for an antibody, or a binding fragment or portion thereof, that specifically binds to a target protein expressed on the surface of a cell, wherein the method comprises establishing a cell line which expresses the target protein on the cell surface; wherein the cell surface expressed target protein is capable of being detected by a detectably labeled binding molecule; expressing in the cell line an antibody, or a binding fragment or portion thereof, for selection for binding to the target protein, wherein the antibody, or a binding fragment or portion thereof, is fused to a signal sequence for retaining the antibody, or a binding fragment or portion thereof, in an intracellular organelle under conditions allowing for the interaction and binding of the antibody, or a binding fragment or portion thereof, and the target protein within the organelle; and detecting the level of the target protein expressed on the cell surface with the detectably labeled binding molecule; wherein, if the antibody, or a binding fragment or portion thereof, specifically binds to the target protein in the organelle, the target protein is bindably retained therein, thereby decreasing or virtually eliminating the level of expression of the target protein on the cell surface; and indicating the retention of a selectable antibody, or a binding fragment thereof, that specifically binds to the target protein in the cell.

In an embodiment of the method set forth directly above, the method further comprises recovering from the cells the antibody, or a binding fragment or portion thereof, that specifically binds to the target protein by conventional methods. In another embodiment, the antibody, or a binding fragment or portion thereof, is fused to a signal sequence for retaining the antibody, or a binding fragment or portion thereof, in the endoplasmic reticulum (ER) intracellular organelle. In another embodiment, the antibody, or a binding fragment or portion thereof, is fused to the KDEL signal sequence (SEQ ID NO:1) which retains the antibody, or a binding fragment or portion thereof, in the ER. In another embodiment, the target protein is a plasma membrane-expressible protein expressed on the cell surface, e.g., a hTNF-α protein. In another embodiment, the cell line is infected or transduced with a lentiviral particle encoding the nucleic acid sequence encoding the antibody, or a binding fragment or portion thereof. In another embodiment, the antibody, or a binding fragment or portion thereof, is a member of an antibody library or a member of a library comprising antibody binding fragments or portions, which may be diversified. In another embodiment, the antibody, or a binding fragment or portion thereof, is a $V_L$ and/or $V_H$ domain of the antibody. In an exemplary embodiment, the antibody, or a binding fragment or portion thereof, is a $V_L$ and/or $V_H$ domain that binds hTNF-α. In another embodiment, the antibody, or a binding fragment or portion thereof, is a member of a $V_L$ and/or $V_H$ domain library. In an exemplary embodiment, the level of the target protein expressed on the cell surface is detected by flow cytometry and a detectably labeled anti-hTNF-α antibody.

In another of its aspects, the invention provides a method of selecting from a plurality of binding molecules a binding molecule which binds a target antigen that is a member of an interacting pair comprising a cell surface-expressed receptor binding protein and its cognate ligand. Accordingly, the method comprises (a) introducing nucleic acid encoding one of a plurality of binding molecules into cells expressing the receptor binding protein and the cognate ligand, which is fused to a retention signal that retains the cognate ligand in an intracellular organelle; (b) expressing in the cells the nucleic acid of (a), wherein an expressed binding molecule binds to the receptor binding protein or the cognate ligand target antigen retained in the organelle and disrupts or blocks the interaction between the receptor binding protein and the cognate ligand; and (c) detecting the level of receptor binding protein expressed on the cell surface; wherein, if the binding molecule binds to either the receptor binding protein or the cognate ligand in the organelle and disrupts or blocks their interaction, the receptor binding protein is expressed and detectable on the cell surface, and wherein the binding molecule that disrupts or blocks the interaction is selectable. In an embodiment, the nucleic acid encoding one of a plurality of binding molecules is introduced into the cells by lentivirus particles harboring the nucleic acid. In an embodiment, the method further comprises recovering or isolating the selected binding molecule from the cell. In an embodiment of the method, the plurality of binding molecules is selected from an antibody library, a genetically diversified antibody library, a single domain antibody library, a genetically diversified single domain antibody library, a $V_L$ library, a genetically diversified $V_L$ library, a $V_H$ library, or a genetically diversified $V_H$ library. In a specific embodiment, the plurality of binding molecules is a $V_L$ library, a genetically diversified $V_L$ library, e.g., as exemplified herein by hTNF-α $V_L$ binding domains. In an embodiment, the binding molecule, or a binding portion thereof, is selected from an antibody, or a binding fragment or portion thereof. In an embodiment, the antibody, or a binding fragment or portion thereof, is selected from a polyclonal antibody, a monoclonal antibody, a chimeric antibody, a humanized antibody, a fully human antibody, or a single chain antibody. In an embodiment, the antibody binding fragment or portion is selected from an Fab' fragment, an Fab' fragment, an F(ab')2 fragment, an Fd fragment, an Fv fragment, a single-chain antibody fragment (scFv), a domain antibody (dAb), a diabody, a heavy chain variable domain ($V_H$), a light chain variable domain ($V_L$), or a complementarity determining region (CDR). In an embodiment, the antibody binding fragment or portion thereof is a $V_L$ domain or a genetically diversified $V_L$ domain. In an embodiment, the antibody binding fragment or portion thereof is a $V_H$ domain or a genetically diversified $V_H$ domain. In various embodiments, the intracellular organelle is the ER or the Golgi; the cognate ligand is molecularly tagged with a sequence for retaining the ligand in the ER; and the ER retention sequence is KDEL (SEQ ID NO:1).

In yet another of its aspects, the invention provides a method of selecting from a plurality of binding molecules, a binding molecule, or a binding portion thereof, that binds a cell surface expressed target antigen. Accordingly, the method comprises introducing into cells nucleic acid sequences encoding one of a plurality of binding molecules operably linked to nucleic acid encoding a intracellular organelle retention signal, wherein the same cells express the target antigen which is expressible on the cell surface; expressing in the cells the plurality of binding molecules comprising the retention signal; wherein, if one of the plurality of binding molecules comprises a binding molecule, or a binding portion thereof, that specifically binds to the target protein, the target protein is retained in the cell organelle through its being bound to the binding molecule, or a binding portion thereof, that is retained in the intracellular organelle via its expressed retention signal, thereby preventing both exit of the target protein from the organelle and expression of the target protein on the cell surface; and detecting the level of the target protein expressed on the cell surface. According to the method, if a non-detectable or low level of the target protein is detected on the cell surface relative to a suitable control, this indicates the specific binding of the binding molecule, or the binding portion thereof, to the target molecule in the cell, wherein the binding molecule, or the binding portion thereof, is selected by the method and may be isolated or recovered from the cells via conventional methods. In an embodiment, the nucleic acid encoding one of the plurality of binding molecules is introduced into the cells by lentivirus particles harboring the nucleic acid. In an embodiment, the method further comprises recovering or isolating the selected binding molecule from the cell. In an embodiment, the plurality of binding molecules is selected from an antibody library, a genetically diversified antibody library, a single domain antibody library, a genetically diversified single domain antibody library, a $V_L$ domain library, or a genetically diversified $V_L$ library, a $V_H$ domain library, or a genetically diversified $V_H$ library. In an embodiment, the binding molecule, or a binding portion thereof, is selected from an antibody or a binding fragment or portion thereof. In an embodiment, the antibody, or a binding fragment or portion thereof, is selected from a polyclonal antibody, a monoclonal antibody, a chimeric antibody, a humanized antibody, a fully human antibody, or a single chain antibody. In an embodiment, the antibody binding fragment or portion is selected from an Fab fragment, an Fab' fragment, an F(ab')2 fragment, an Fd fragment, an Fv fragment, a single chain antibody fragment (Fv), a domain antibody (dAb), a diabody, a heavy chain variable domain ($V_H$), a light chain variable domain ($V_L$), or a complementarity determining region (CDR). In an embodiment, the plurality of binding molecules is an antibody $V_L$ library or a genetically diversified $V_L$ library. In an embodiment, the antibody binding fragment or portion thereof is a $V_L$ domain or a genetically diversified $V_L$ domain. In an embodiment, the plurality of binding molecules is an antibody $V_H$ library or a genetically diversified $V_H$ library. In an embodiment, the antibody binding fragment or portion thereof is a $V_H$ domain or a genetically diversified $V_H$ domain. In an embodiment, the intracellular organelle retention signal is an endoplasmic reticulum (ER) or Golgi retention signal. In an embodiment, the ER retention sequence is KDEL (SEQ ID NO:1).

In another of its aspects, the invention provides a method of selecting from a plurality of binding molecules a binding molecule which binds a target antigen that is a member of an interacting pair comprising a cell surface-expressed receptor binding protein and a cognate ligand, the method comprising: (a) co-expressing in a single cell which expresses the receptor binding protein: (i) nucleic acid sequence encoding one of a plurality of binding molecules, and (ii) nucleic acid sequence encoding a cognate ligand of the receptor binding protein, wherein either the binding molecule or the cognate ligand is operably coupled to a nucleic acid sequence encoding a retention signal for retaining either (i) or (ii) in an intracellular organelle following expression of (i) or (ii) in the cell; under conditions allowing for retention of the expressed binding molecule or the expressed cognate ligand in the intracellular organelle; wherein, if an expressed binding molecule binds to the receptor binding protein or the cognate ligand as target antigen, such binding disrupts, neutralizes, or blocks the natural interaction between the receptor binding protein and the cognate ligand and releases the receptor binding protein from its interaction with the cognate ligand for expression of the receptor binding protein on the cell surface; and (b) detecting the level of receptor binding protein expressed on the cell surface such that a high level of receptor binding protein expression of the cell surface indicates the expression and selection of a specific binding molecule which binds target antigen within the cell. In an embodiment of the method, the plurality of binding molecules is selected from an antibody library, a genetically diversified antibody library, a single domain antibody library, a genetically diversified single domain antibody library, a $V_L$ domain library, a genetically diversified $V_L$ domain library, a $V_H$ domain library, or a genetically diversified $V_H$ domain library. In an embodiment, the binding molecule is an antibody or a binding fragment or portion thereof, such as an Fab fragment, an Fab' fragment, an F(ab')2 fragment, an Fd fragment, an Fv fragment, a single-chain variable fragment (scFv), a diabody, a domain antibody (dAb), a heavy chain variable domain ($V_H$), a genetically diversified heavy chain variable domain ($V_H$), a light chain variable domain ($V_L$), a genetically diversified light chain variable domain ($V_L$), or a complementarity determining region (CDR). In embodiments, the binding molecule is a $V_L$ domain, a genetically diversified $V_L$ domain, a $V_H$ domain, or a genetically diversified $V_H$ domain. In embodiments, the binding molecule is a full length antibody comprising light chain variable domains and light chain constant domains, and heavy chain variable domains and heavy chain constant domains, such as an IgG antibody or a subclass thereof, e.g. an IgG1 antibody. In embodiments, the intracellular organelle is the endoplasmic reticulum (ER) or the Golgi and the intracellular organelle retention signal is a KDEL amino acid sequence (SEQ ID NO:1). In embodiments the target antigen can be the types of receptor proteins or cognate ligands as described herein.

In yet another aspect, the invention provides a method of preventing or "knocking down" cell surface expression of a ligand-binding receptor protein, wherein the method comprises expressing in a cell the ligand-binding receptor protein; expressing in the cell a ligand protein capable of being bound by the ligand-binding receptor protein, wherein the ligand protein is fused to an exogenous signal sequence for retaining the ligand protein in an intracellular organelle, under conditions permitting the interaction of the ligand-binding receptor protein and the ligand protein in the organelle; measuring the level of the ligand-binding receptor protein expressed on the cell surface; wherein the binding of the ligand-binding receptor protein to the ligand protein retained in the organelle concomitantly retains in the organelle the ligand-binding receptor protein bound to the ligand protein, thereby preventing or "knocking down" the cell surface expression of the ligand-binding receptor protein.

In another of its aspects, the invention provides a method of generating genetic diversity or variability in a binding molecule, or a binding portion thereof, such as an antibody, by modifying immunoglobulin complementarity determining regions (CDRs), wherein the method involves (a) introducing into one or more CDR-encoding nucleic acid sequences one or more zinc finger DNA binding domain recognition sequences, thereby producing one or more non-identical targeting sites within the one or more CDR-encoding nucleic acid sequences for binding one or more zinc finger nucleases (ZFN) and producing a modified CDR-encoding nucleic acid sequence; (b) introducing into a nucleic acid sequence encoding a zinc finger nuclease (ZFN) at least one of the one or more zinc finger DNA binding domain recognition sequence targeting sites of (a), which sequences are operably linked to a nucleic acid sequence encoding a DNA cleavage domain of a type IIS restriction enzyme, wherein DNA cleavage by the ZFN is determined by the targeting site within the modified CDR-encoding nucleic acid sequence of (a); and (c) expressing the nucleic acid sequences of (b) in a cell containing nucleic acid encoding at least an antibody heavy chain variable domain ($V_H$) and/or at least an antibody light chain variable domain ($V_L$) containing the modified CDR-encoding nucleic acid sequence of (a) under conditions in which the expressed ZFN binds and cleaves the modified CDR-encoding nucleic acid sequence within the targeting site sequence. It will be appreciated that the one or more zinc finger DNA binding domain recognition sequences are introduced into the nucleic acid sequences encoding one or more of the CDR regions of a nucleic acid sequence encoding an antibody variable region.

In accordance with this method, within the cell, the processes of recombination, repair and rejoining of cleaved DNA within the modified CDR-encoding nucleic acid sequences provides for hypermutation in and/or around the targeting site sequences, or "hotspots" where the ZFN binds and cleaves the DNA within the CDR. Expression of the resulting CDRs within at least the $V_H$ and/or $V_L$ regions expressed in the cell ultimately provides genetically diversified binding molecule or antibody products having the potential to exhibit improved or optimal binding to a target antigen. In an embodiment, in (a), the CDR-encoding nucleic acid sequences are contained within a nucleic acid vector or cassette, e.g., a DNA vector, suitable for carrying out molecular biology techniques and genetic manipulation. The zinc finger DNA binding recognition sequences are introduced into the CDR-encoding nucleic acid sequences which are harbored in the vector or cassette to produce the one or more modified CDRs, for example, CDR1, CDR2, or CDR3 of an antibody light chain and/or CDR1, CDR2, or CDR3 of an antibody heavy chain. In an embodiment, the nucleic acid vector or cassette comprising the one or more modified CDRs is thereafter introduced into nucleic acid sequence encoding a $V_L$ and/or a $V_H$ domain such that the resulting locations of the expressed CDRs are in the orientation in which they are normally expressed in the heavy or light chain variable region. In an embodiment, in (a) of the method, the CDR-encoding nucleic acid sequences are contained within nucleic acid sequences encoding an antibody heavy chain variable domain ($V_H$) and/or nucleic acid sequences encoding an antibody light chain variable domain ($V_L$) at the time that the zinc finger DNA binding domain recognition sequences are introduced into the CDR-encoding nucleic acid sequence. In an embodiment, in (c), the modified CDR-encoding nucleic acid sequence is contained within a full length antibody comprising nucleic acid sequences encoding a heavy chain variable domain ($V_H$) and a heavy chain constant region ($C_H$), and comprising nucleic acid sequences encoding a light chain variable domain ($V_L$) and a light chain constant region ($C_L$), wherein the resulting nucleic acid sequences encode full length antibodies comprising $V_H$ and $V_L$ domains comprising modified CDRs. In an embodiment, the method further comprises amplifying and, optimally, cloning the nucleic acid sequences encoding the $V_H$ and/or $V_L$ domain proteins from the cell.

In another aspect, the invention provides a method of generating a genetically diverse antibody, or a binding fragment or portion thereof, comprising modified complementarity determining regions (CDRs), wherein the method comprises producing one or more modified CDRs by introducing into nucleotide sequences encoding the one or more individual CDRs of antibody $V_H$ and/or $V_L$ domains, one or more zinc finger DNA binding domain nucleic acid recognition sequences (or targeting sites) for binding zinc finger nucleases (ZFNs) that have been engineered to contain the one or more zinc finger binding domain targeting sites as introduced into the CDR-encoding nucleic acid sequences covalently linked to the DNA cleaving domain of a type IIS endonuclease, such as Fok1; wherein the ZFNs cleave within the CDRs as determined by the specificity of the CDR-containing zinc finger DNA binding domain nucleic acid recognition sequences of (a). Nucleic acid sequences encoding $V_H$ and/or $V_L$ domains containing the one or more modified CDRs, or encoding full-length immunoglobulin molecules encoding $V_H$ and/or $V_L$ domains containing the one or more modified CDRs, are expressed in cells under the appropriate conditions and time for the ZFNs to cleave within the specific targeting sequence sites in the CDRs and for the cellular recombination and repair proteins to generate $V_H$ and/or $V_L$ domains comprising genetically diversified binding regions by virtue of the cleavage within the CDR sequence and the rejoining of sequences within the CDRs with consequent mutations in the original sequence resulting from the intra-CDR hotspots or sites within the CDRs that are bound and cleaved by the ZFNs. In this way, a genetically diverse set of CDR sequences comprising the binding regions of expressed $V_H$ and/or $V_L$ domains, or antibodies comprising such domains, are obtained. Such diversity provides an antibody or a population of antibody molecules which can have improved or optimized binding properties for the target antigen.

In the described methods, the nucleic acid sequences encoding the one or more CDRs may originate or be obtained from an antibody or antibodies that bind a known antigen, or they may originate or be obtained from a library encoding antibody molecules having a variety of binding specificities, or unknown target binding specificities. The CDRs may originate or be derived from immunoglobulins of different animal species, including, for example, mammals such as humans, mice, rats, rabbits, guinea pigs, dogs, sheep, cows, horses, pigs and the like. In an embodiment, the CDRs are human CDRs. In an embodiment, the CDRs are non-human CDRs, such as rabbit CDRs, or mouse CDRs, or rat CDRs.

In embodiments of the methods, the nucleic acid sequences of the modified CDRs and the ZFNs are introduced into a host cell under conditions in which the ZFNs target and cleave the modified CDRs within the introduced zinc finger binding recognition sites and under conditions for producing genetically diverse, i.e., mutation-containing, antibody products, or binding portions thereof. The mutations resulting from the practice of the genetic diversification methods of the invention may be in the form of, for example, insertions, deletions or substitutions of nucleotides (base pairs) within the CDR hypervariable regions of $V_H$ and/or $V_L$ domains. Such mutations may, following expression of the antibody products, positively affect the binding of the resulting, expressed binding regions to target antigen, i.e., by providing better binding specificity and/or affinity for the target antigen. In an embodiment of the methods, the CDR-encoding nucleic acid sequences are genetically modified outside of the $V_H$ and/or $V_L$ domains, e.g., within a nucleic acid vector and/or cassette, and are subsequently introduced into the $V_H$ and/or $V_L$ domain-encoding nucleic acid sequences. In an embodiment, the CDR-encoding nucleic acid sequences are genetically modified in the CDR locus within the $V_H$ and/or $V_L$ domains in which they reside. In an embodiment of the methods, the modified CDR-encoding nucleic acid sequences are introduced into the nucleic acid sequences encoding the $V_H$ and/or $V_L$ domains of an antibody protein. In an embodiment, the nucleic acid sequences encoding the $V_H$ and/or $V_L$ domains comprising the genetically modified CDRs are, in turn, molecularly cloned to be operably expressed with nucleic acid sequences encoding antibody heavy (H) and light (L) chains, wherein the resulting nucleic acid sequence encodes an antibody protein comprising modified CDR regions comprising different ZFN recognition sites within the $V_H$ and $V_L$ domains.

In an embodiment, the nucleic acid sequences encoding the modified CDRs; or the nucleic acid sequences encoding $V_H$ and/or $V_L$ domains into which the modified CDRs have been introduced; or the nucleic acid sequences encoding a full-length antibody comprising $V_H$ and/or $V_L$ domains comprising modified CDRs, are expressed in a suitable host cell using one or more suitable expression vectors, e.g., lentivirus vectors. The resulting $V_H$ and/or $V_L$ domains comprising modified CDRs, or one or more antibodies comprising $V_H$ and/or $V_L$ domains comprising modified CDRs, can be screened or selected for binding to a target antigen within the same cell according to the described methods herein. In an embodiment, the selection method comprises the methods of the invention described herein in which the $V_H$ and/or $V_L$ domain or antibody binds to target antigen, i.e., one member of a binding pair comprising a receptor binding protein or its cognate ligand, within the same cell. As described in detail herein, the cognate ligand is typically fused or coupled to a retention signal that retains the ligand in an organelle such as the ER. If the $V_H$ and/or $V_L$ domain or antibody comprising such $V_H$ and/or $V_L$ domains binds either the receptor binding protein or its ligand within the environment of the ER, the binding interaction between receptor protein and cognate ligand is disrupted, neutralized, or blocked. The ligand is retained in the organelle by virtue of its retention signal; however, the receptor protein, freed from its interaction with its ligand, can transit through the ER and be expressed on the cell surface. Such cell surface expression of the "released" receptor is detectable (and quantifiable) by the binding of specific antibodies and detection thereof, e.g., by flow cytometry. The detection of signal, relative to controls, indicates that the cell contains a $V_H$ and/or $V_L$ domain or antibody which binds to the target molecule within the cell, and that such a binding event has effectively disrupted, neutralized, or blocked the receptor-ligand interaction.

In other embodiments, the methods further comprise isolating or recovering the nucleic acid sequence encoding the binding molecule, or a binding portion thereof, e.g., an antibody or a binding portion thereof, produced in the cells, amplifying the encoding nucleic acid sequences, e.g., by PCR, and cloning the nucleic acid sequences encoding binding molecule, or a binding portion thereof, e.g., an antibody, or a binding portion thereof, or a genetically diverse form thereof from the cell.

BRIEF DESCRIPTION OF THE DRAWINGS

FIGS. 1A-1D present a demonstration of the technology and method of the invention as tested using recombinant antibodies directed either to the ligand binding receptor protein hTNF-α receptor I, or to its cognate ligand protein hTNF-α and showing that both types of antibodies can block or disrupt the interaction between the ligand receptor protein hTNF-α receptor I and its cognate ligand hTNF-α. As depicted, a Jurkat cell line expressing a representative receptor protein, i.e., hTNF-α receptor I, at the surface of the cell was molecularly engineered to express and retain certain of the expressed proteins in accordance with the invention. The presence of the receptor at the cell surface can be detected by a detectably labeled, e.g., fluorescence, antibody directed to hTNF-α receptor I. Abbreviations: ER, endoplasmic reticulum; hTNF-α, human tumor necrosis factor alpha; KDEL (SEQ ID NO:1), retention signal for ER; $V_L$, light chain variable region from anti-hTNF-α receptor I antibody.

As shown in FIG. 2A, the cell surface-expressed hTNF-α protein is detected at the surface of the cell by a detectable antibody that specifically recognizes and binds the cell surface-expressed hTNF-α protein. In FIG. 2B, because the cells are transduced with $V_L$ antibody-KDEL molecules ("KDEL" disclosed as SEQ ID NO:1), the $V_L$ antibody that specifically binds to hTNF-α protein retains this target protein in the ER, and the hTNF-α protein is no longer detected at the surface of the cell by the detectable antibody. Abbreviations: ER, endoplasmic reticulum; hTNF-α, human tumor necrosis factor alpha; KDEL (SEQ ID NO:1), retention signal for ER; $V_L$, light chain variable region from an hTNF-α antibody; "TNF-α-tmd-TEV", a TNF-α target protein comprising a transmembrane domain (tmd) and fused to the TEV protease (catalytic domain of the Nuclear Inclusion a (NIa) protein encoded by the tobacco etch virus (TEV)) as a cytoplasmic domain.

Figure 5:
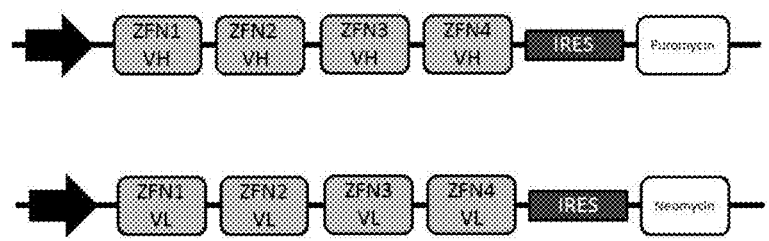

FIG. 5 shows a schematic depiction of the plasmids constructed to express all Zinc Finger Nucleases 1-4 in tandem in the backbone of the lentiviral vector FugW. In one plasmid zinc-finger-nuclease was cloned by overlap PCR with a 2 A sequence separating each gene. ZFN1VH and ZFN2VH target CDR1 in the heavy chain variable region; ZFN3VH and ZFN4VH target CDR3 in the heavy chain variable region; ZFN1VL and ZFN2VL target CDR1 in the light chain variable region; and ZFN3VL and ZFN4VL target CDR3 in the light chain variable region. The lentiviral vector for zinc-finger-nucleases targeting $V_H$ contains a puromycin resistance gene; and the lentiviral vector for zinc-finger-nucleases targeting $V_L$ contains a neomycin resistance gene. Abbreviations: ZFN1, ZFN2, ZFN3, ZFN4, Zinc Finger Nucleases 1-4; IRES, Internal Ribosome Elongation Sequence. As understood by the skilled practitioner, the internal ribosome entry site (IRES) is a noncoding RNA fragment with the ability to initiate high levels of cap-independent protein synthesis in mammalian cells. IRES sequences are used to express two proteins from a single promoter in an expression construct or a transgenic construct. A single RNA is produced, but due to the presence of the IRES, a second translational start is possible on the same RNA. As utilized in the described vectors, IRES sequences permit expression of the ZFN together with a selection marker for construction of cell lines.

FIGS. 6A-6E show schematic representations of various plasmids used to construct cell lines for demonstrating and carrying out the methods of the present invention. (A) $pV_L18$-IRES-DsRed, (B) $pV_L18$ KDEL-IRES-DsRed ("KDEL" disclosed as SEQ ID NO:1), (C) pTNFKDEL-IRES-DsRed ("KDEL" disclosed as SEQ ID NO:1), (D) pTNF-TEV, and (E) pTAX-IRES-DsRed. BamHI: restriction enzyme; c-Myc: c-Myc tag; DsRed: red fluorescence protein; EcoRI: restriction enzyme; HA: hemagglutinin tag; Tax: Transactivator of HTLV-I; $His_6$ (SEQ ID NO:46): histidine tag; HpaI: restriction enzyme; hTNF-α, human tumor necrosis factor alpha; PDGFR tmd: transmembrane region of the platelet derived growth factor receptor (PDGFR); hUbc: human ubiquitin C promoter; IgGκ-chain leader: murine Ig-κ-chain leader sequence; IRES: internal ribosome entry site; KDEL (SEQ ID NO:1): retention signal for endoplasmic reticulum; NheI: restriction enzyme; SfiI: restriction enzyme; and TEV: tobacco etch virus protease.

Figure 7A:
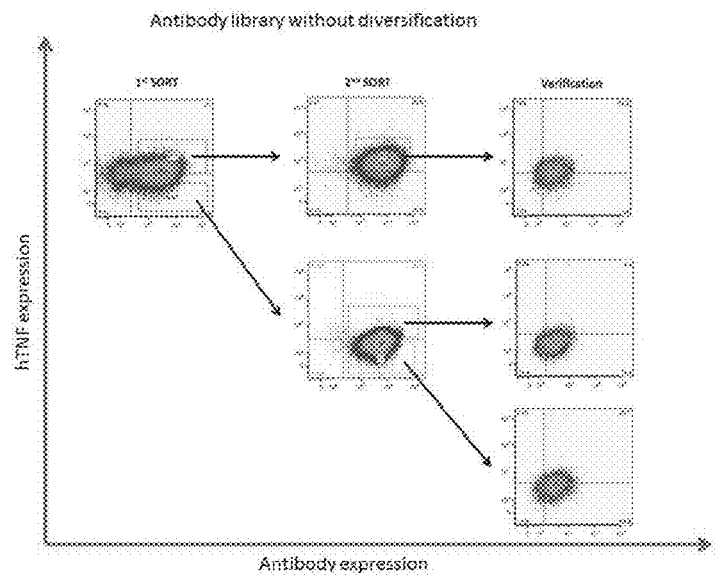
Figure 7B:
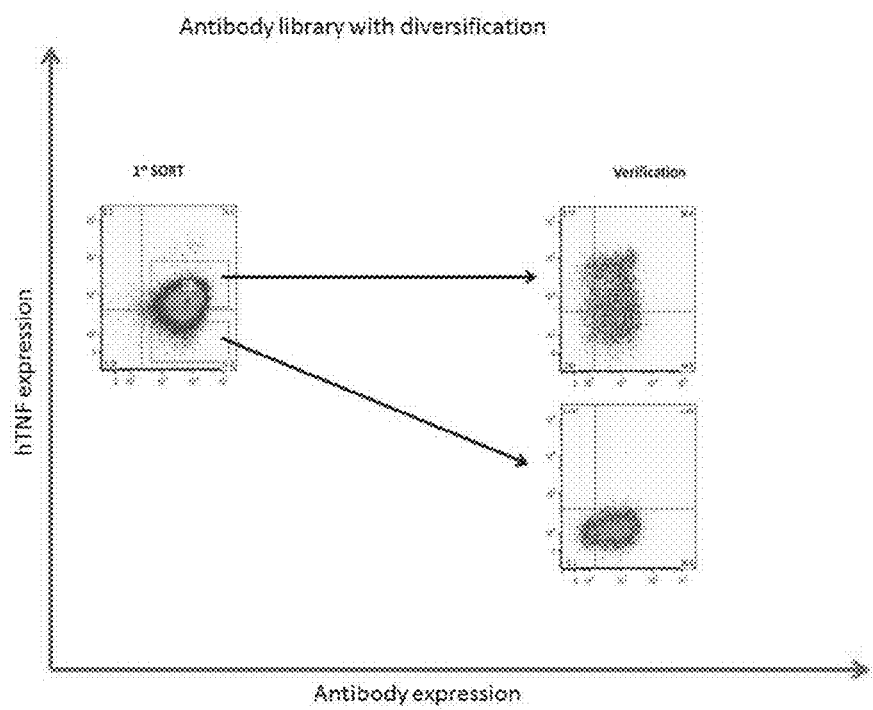

FIGS. 7A and 7B show verification results of the selection methods of the invention as determined by flow cytometry screening analysis of anti-hTNF-α antibody libraries diversified using the zinc finger nuclease methodology described herein. (7A): Antibody library without diversification; (7B): Antibody library with diversification. Cell populations were produced which expressed antibody in the absence of zinc-finger hotspots and induced diversification (7A). Other cell populations were produced which expressed antibody engineered to contain zinc finger hotspots and induced genetic diversification and which also expressed zinc finger proteins and Tax. (7B). After several cycles of sorting by flow cytometry those cells selected by the methods of the invention for having reduced expression of antigen (hTNF-α) at the cell surface, antibodies and clonal populations thereof, which bind a target molecule and reduce expression of hTNF-α at cell surface were isolated.

Figure 8:
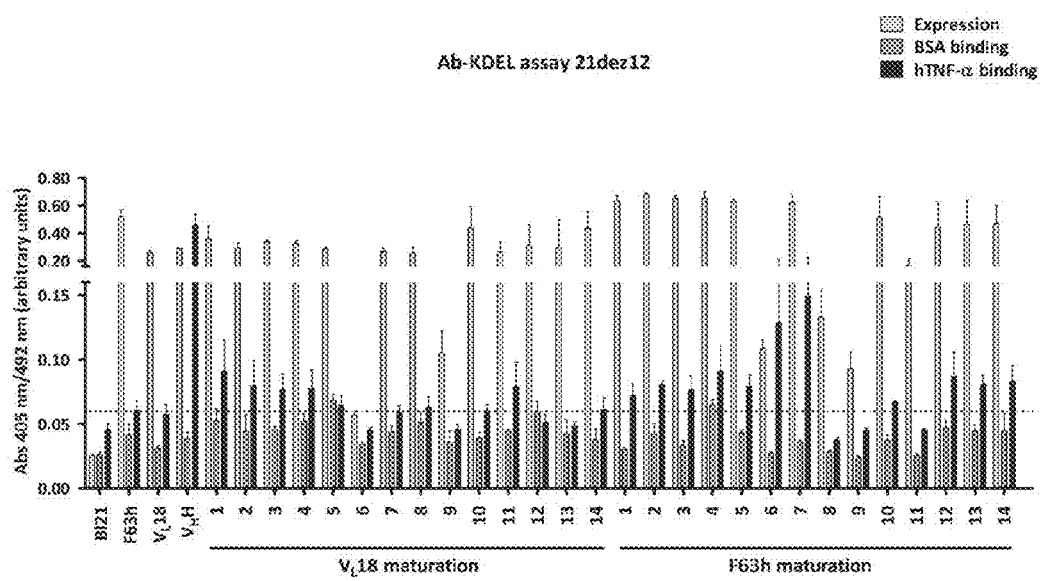

FIG. 8 shows the results of an ELISA assay in which antibody fragments derived from the selection methods of the invention were cloned into the pT7 expression vector (Sigma-Aldrich. St. Louis, Mo.), expressed and assayed by ELISA for binding to hTNF-α. A selected antibody/clone was grown in auto-induction medium. After 16 hours, the cells were lysed and the supernatant was used for the expression and binding assay in ELISA (using 200 ng of hTNF-α). BL21: bacteria used for transformation by the vectors harboring antibody-encoding DNA (used as negative control); hF63: single-domain antibody $V_L$ selected via phage-display against HIV-1 gp41 antigen (used as irrelevant control); $V_L18$, single-domain antibody $V_L$ against hTNF-α; $V_HH$: camel-single-domain antibody against hTNF-α (Ablynx); #1-14 $V_L18$ maturation: clones chosen after $V_L18$ antibody maturation in transformed cells; #1-14 hF63 maturation: clones chosen after hF63 antibody maturation in transformed cells. The results as shown indicate maturation of a light chain antibody fragment ($V_L$) that binds to hTNF-α ($V_L18$) as produced via the diversification methods according to the invention. The irrelevant antibody (F63) that does not bind hTNF-α was used as a control in assays performed in parallel As depicted in the graph, several monoclonal $V_L$ antibodies derived from $V_L18$ showed higher binding to hTNF-α indicating maturation of the antibody. Similarly, antibodies derived from F63 also showed higher binding, indicating that these antibodies have evolved to recognize a different antigen. FIG. 8. Discloses "KDEL" as SEQ ID NO:1.

DETAILED DESCRIPTION OF THE EMBODIMENTS

Described herein are a platform technology and methods for selecting a binding molecule, e.g., an antibody, or a binding portion thereof, that specifically recognizes and binds a target molecule, preferably a protein, polypeptide, or peptide, within a cell. The methods involve the co-expression in a cell of (i) the binding molecule, (ii) its target, which, in an aspect of the invention can be a cognate ligand member of a cell-surface expressible receptor protein-cognate ligand binding pair, and (iii) the cell-surface expressible receptor protein with which the cognate ligand interacts. The cognate ligand can be fused to an intracellular organelle retention signal, (e.g., an endoplasmic reticulum (ER) retention signal), such that when the cognate ligand binds and interacts with the receptor protein in the cell, both are retained and localized in the cell organelle by virtue of the ligand's possessing the retention signal. The presence of the binding molecule within the same cell as its target, the cognate ligand, allows the binding molecule to bind its target within the cell, thereby disrupting, neutralizing, or blocking the typical binding interaction between the cognate ligand target and its receptor protein. This disruption of the interaction between the ligand binding pair by the binding molecule allows the receptor protein to exit the organelle, travel to the cell surface and be expressed on the cell surface, while the cognate ligand is retained in the cellular organelle. The receptor protein, displayed on the cell surface is detectable by a specific detectable agent and detection methods, and indicates the presence of the binding molecule within the cell. The binding activity of the binding molecule to its target (the cognate ligand member of the ligand binding pair) results in the release of the receptor protein from its binding interaction with cognate ligand and its expression and detection on the cell surface. The binding molecule can be isolated from the cell in which it has been selected by the methods of the invention. Variations on the technology and methods of the invention are further described herein.

The technology and methods of the invention are useful and advantageous for (i) reducing undesirable variables due to recombinant and amplification techniques; (ii) combining affinity and expression maturation of binding molecules, such as antibodies; (iii) promoting binding molecule or antibody selection for target proteins at a native location in the cell; and (iv) integrating the foregoing features using high-throughput screening or selection methods. Accordingly the invention encompasses a new platform technology and methods that couple the aspects of effective selection, expression and maturation of binding molecules, such as antibodies, with their binding to target proteins or antigens in a cellular environment, in which both the binding and the target molecules are located and expressed.

In an embodiment, the binding molecule is an antibody, or a binding fragment or portion thereof, which specifically binds a target molecule or antigen, as described herein. In an embodiment, the binding molecule is a $V_L$ and/or a $V_H$ domain portion of an antibody. In an embodiment, the $V_L$ and/or $V_H$ domain, or the antibody, or a binding fragment or portion thereof, is genetically diversified as described herein. In an embodiment, a library of binding molecules is used for selecting or screening for those member molecules that specifically bind a target molecule or antigen in accordance with the methods of the invention. In an embodiment, an antibody library, either constructed or otherwise obtained, is used for selecting or screening for those antibodies that specifically bind a target molecule or antigen. In an embodiment, the antibodies, or binding portions thereof, are genetically diversified by the methods as described herein and are selected or screened for binding to a target antigen utilizing the cellular selection methods described herein.

In an embodiment, the target molecule is a ligand binding molecule, e.g., a ligand binding receptor protein, i.e., "receptor protein", that is expressed on the cell surface. In an embodiment, the receptor protein is a membrane-spanning receptor protein comprising an extracellular domain that can be recognized and bound by a specific antibody. In an embodiment, the target molecule is a protein or antigen, e.g., a cognate ligand, that binds and interacts with a ligand binding molecule, e.g., a ligand binding receptor protein. The cognate ligand is preferably a protein, polypeptide, or peptide. In an embodiment, the cognate ligand or ligand binding protein can be expressed, or can be molecularly engineered to be expressed, in the cell's plasma membrane.

Expression of the ligand binding molecule, or receptor protein, or the cognate ligand in the cell membrane relates to the ability of the ligand binding molecule or the cognate ligand to be recognized and specifically bound by a detectable molecule, such as an antibody, in a suitable detection assay. Accordingly, a bindable portion of the ligand binding molecule or the cognate ligand is exposed to the extracellular environment such that it (and its relevant epitopes) can be specifically recognized and bound by the detectable molecule or antibody. In an embodiment, the detectable molecule or antibody, e.g., a "first" antibody, can be directly labeled with a detectable label, which can be detected, measured, or quantified by conventional methods. In an embodiment, the detectable molecule or antibody is not directly labeled, but instead is specifically bound by a secondary binding molecule or antibody, which is detectably labeled and can be detected, measured, or quantified. The detectable secondary binding molecule or antibody serves as an indirect label for the first antibody, which may provide a higher or more optimal signal, such as in flow cytometry detection methods.

As used herein a "binding molecule" refers to a molecule, or a binding fragment or portion thereof, that binds to a target molecule or antigen. A binding molecule is preferably a protein, polypeptide, or peptide that can recognize and bind to a target molecule or antigen. The target molecule or antigen is preferably a protein, a glycoprotein, a polypeptide or a peptide. The binding molecule can be an antibody or immunoglobulin, or a binding or functional fragment or portion thereof. A functional fragment or portion of an antibody or immunoglobulin encompasses a binding fragment or portion thereof, such as a $V_L$ and/or a $V_H$ domain, that specifically binds to a target molecule. The binding molecule may also be a non-antibody molecule or a functional fragment or portion thereof.

The target molecule or antigen that is bound by a binding molecule or antibody may be a ligand binding protein (or ligand binding receptor protein), polypeptide, or peptide, such as a receptor protein, e.g., a cell-surface expressed receptor protein, that typically binds to a cognate ligand or ligand protein. A "cognate ligand" or "ligand protein" refers to the ligand/protein/peptide, etc. with which the ligand binding protein typically interacts and/or binds. The cognate ligand may be modified, derivatized, or fused to other sequences or domains; however, it can still interact with its ligand binding protein or receptor protein. Alternatively, the target molecule or antigen that is bound by a binding molecule or antibody may be a cognate ligand that interacts with and/or binds to its ligand binding protein to form an interacting ligand binding protein/cognate ligand pair, also termed a "binding pair" herein. A nonlimiting example of a ligand binding receptor protein is human TNF-α receptor 1 (hTNF-α receptor 1), while a nonlimiting example of its cognate ligand is human TNF-α (hTNF-α). Illustratively, human TNF-α receptor 1 interacts with and binds human TNF-α (hTNF-α) and together they form a binding pair, with each protein being a member of the binding pair. It will be understood that throughout this application, human TNF-α receptor 1 (hTNF-α receptor 1) represents a nonlimiting example of a ligand binding receptor protein that interacts with and binds human TNF-α (hTNF-α), which represents a nonlimiting example of a cognate ligand. Accordingly, verification of the selection and diversification methods of the invention using such a ligand binding protein-cognate ligand pair, for example, as set forth in the Examples herein, are not intended to limit the various embodiments of the invention in any way.

The term "antibody" includes an intact immunoglobulin having four polypeptide chains, two heavy (H) chains and two light (L) chains linked by disulfide bonds. The term "antibody" is synonymous with the term "immunoglobulin" and encompasses polyclonal antibodies, monoclonal antibodies (mAbs), chimeric antibodies, humanized antibodies, fully human antibodies, single chain antibodies and molecules having functionality to bind a specified target, protein, or antigen. The term "antibody" also encompasses antibody fragments or portions thereof, illustratively including, but not limited to, fragments such as an Fab fragment, an Fab' fragment, an F(ab')2 fragment, an Fd fragment, an Fv fragment, a single-chain variable fragment (scFv), a diabody and a domain antibody (dAb). Also encompassed by "antibody" are the variable (V) regions of the H and L chains of the antibody, i.e., $V_H$ and $V_L$, respectively, that contain complementarity determining regions (CDRs) or regions of hypervariability that typically interact with epitopes on antigen or target molecules that are specifically targeted, recognized and bound by antibodies. Preferably, antibodies and fragments and portions thereof are functional fragments and portions in that they target and specifically bind a target antigen or target protein, such as a ligand binding protein or a cognate ligand protein in accordance with aspects of the invention. The antibodies may be from any species or derivable therefrom, e.g., human, non-human primate, sheep, goat, mouse, rat, rabbit, dog, cow, pig, and the like. In an embodiment, the antibodies are human antibodies. In an embodiment, the antibodies are humanized antibodies. In addition, the antibodies, or binding fragments or portions thereof, may be of any class, e.g., IgM, IgA, IgD, IgG, or IgE, or of any subclass thereof, e.g., IgG1, IgG2, IgG2a, IgG2b, IgG3, or IgG4. In an embodiment, the antibody, or a binding fragment thereof, is an IgG1 antibody. The antibody light chains, or fragments or portions thereof, may be of the kappa or lambda type. It will be understood that as used herein, the term antibody is meant to encompass a binding and/or functional fragment and portion thereof.

In some embodiments, the methods encompass the use of an antibody library, e.g., a cloned library of immunoglobulins, or a library of functional fragments or portions of antibodies, such as a single domain antibody (SDA) library, e.g., library of $V_L$ regions. Antibody libraries, including diversified antibody libraries, are particularly useful for selecting antibodies with high or optimal affinity or specificity for binding a given target protein in accordance with the methods of the invention as further described herein. Antibodies or portions thereof that are derived or produced from antibody libraries that have been genetically diversified by the methods described herein are also useful for selecting for their binding capabilities to a given target antigen/target protein within a cell in accordance with the methods of the invention.

Antibodies and antigen binding antibody fragments and methods for their generation, e.g., employing conventional molecular techniques, are known in the art and are described in further detail, for instance, in *Antibody Engineering*, Kontermann, R. and Dubel, S. (Eds.), Springer, 2001; Harlow, E. and Lane, D., *Antibodies: A Laboratory Manual*, Cold Spring Harbor Laboratory Press, 1988; Ausubel, F. et al., (Eds.), *Short Protocols in Molecular Biology*, Wiley, 2002; J. D. Pound (Ed.) *Immunochemical Protocols, Methods in Molecular Biology*, Humana Press; 2nd ed., 1998; B. K. C. Lo (Ed.), *Antibody Engineering: Methods and Protocols*, Methods in Molecular Biology, Humana Press, 2003; and Kohler, G. and Milstein, C., Nature, 256:495-497 (1975) [1].

In other embodiments, the binding molecules encompassed by the invention include proteins, polypeptides, peptides, modified and derivatized forms thereof antibody mimetics, e.g., designed ankyrin repeat proteins (DARPins), affilins, affitins, avimers, anticalins, monobodies, affibody molecules; or a molecule or substance that interacts with the cell membrane and binds a protein or can be bound, e.g., haptomers, aptamers, etc.

In an embodiment, the binding molecule, e.g., an antibody, which has been introduced into a cell by recombinant techniques, expressed and produced in the cell and demonstrated to bind to a target molecule as described herein, can be recovered or isolated from cells using conventional methods in the art. For example, genomic DNA can be isolated and specific fragments amplified using primer oligonucleotides from a cell that has been selected for expression of an antibody which binds a particular target molecule as described in the methods of the invention. A plasmid vector constructed to harbor the amplified DNA fragments can be used to transform bacteria and colonies expressing cloned segments containing antibody-encoding DNA are assayed by binding analysis for expression of antibodies having specific binding properties. See, e.g., Example 4 herein. Antibodies can be expressed directly from the isolated cell clones, without the need for re-cloning. In addition, the cell clones can be isolated and antibody-encoding genes, e.g., IgG antibody-encoding genes, can be amplified, e.g., by polymerase chain reaction (PCR), and re-cloned, for example, in a mammalian expression plasmid for expression and subsequent purification. Optionally, the binding molecule, e.g., an antibody, can be further modified, developed, or purified for therapeutic use using methods known to the skilled practitioner. In an embodiment, the binding molecule, e.g., an antibody, which binds to a ligand binding receptor protein or a ligand protein is identified, recovered, or isolated from cells, and optionally purified, for further use.

According to the invention, antibodies generated and/or selected by the described methods may be employed as therapeutic biological agents. For example, antibodies selected using the described methods may demonstrate improved, more desirable, and/or optimal structural and functional properties compared with known or used antibodies. Through the genetic diversification and selection methods of the invention, binding molecules are provided which may show improved, desirable and/or optimal binding to a cell receptor protein or its cognate ligand, either of which may be associated with a disease, pathology or condition in a subject, such as a human patient, needing treatment. Such binding molecules, e.g., antibodies, when employed as therapeutic agents, may, for example, block, inhibit, or disrupt the binding of a ligand to its cell surface-expressed receptor and prevent activation of intracellular signaling events leading to cell transformation, uncontrolled cell proliferation, or cancer. If the binding molecule is an antibody, the antibody may be directed against a cell surface ligand binding receptor protein and may exhibit enhanced binding and/or functional properties. An antibody as binding molecule may alternatively be directed against a ligand binding protein and may exhibit enhanced binding and/or functional properties.

In an exemplary embodiment in which the selected antibody is directed against human tumor necrosis factor-α (hTNF-α) receptor, such an antibody may be used, for example, in blocking or antagonizing the binding of hTNF-α to its receptor so as to treat a disease or condition associated with hTNF-α expression, e.g., aberrant expression or overexpression, in a subject, preferably a human subject, although treatment of other non-human species is encompassed for the binding molecule products of the methods described herein. Similarly, an antibody directed against the hTNF-α ligand of the hTNF-α receptor may also serve to block the binding of the ligand to its receptor, thereby antagonizing the receptor-ligand interaction and treating a hTNF-α-associated disease or condition. For example, human TNF (such as TNF-α) binding molecules or antagonists, e.g., antibodies and fusion proteins, are useful in the treatment of several immune-mediated, e.g., autoimmune, inflammatory diseases, such as rheumatoid arthritis (RA), juvenile rheumatoid and psoriatic arthritis, plaque psoriasis, ankylosing spondylitis, or inflammatory bowel disease (IBD). Also encompassed by the invention are binding molecules, such as antibodies, that are selected, or diversified and selected, by the cellular methods described herein, wherein the binding molecules, or antibodies, bind other types of receptors expressed on the cell surface, or their cognate ligands. By binding to either the ligand binding receptor protein or the cognate ligand, such antibodies may block, disrupt, inhibit, or eliminate the receptor-ligand interaction.

An antibody, binding molecule, or binding protein included in the embodiments of the present methods may include, or be detectable using, a detectable label. Detectable labels may also be used in various aspects and embodiments of the described methods, e.g., for detection and confirmation of the presence of intracellularly expressed proteins, including binding molecules or antibodies, by flow cytometry methods in which a detectably labeled antibody (or reporter molecule) is used to bind cell surface expressed proteins. Illustrative examples of detectable labels include, without limitation, fluorescent labels, e.g., fluorescein isothiocyanate (FITC), rhodamine, green fluorescent protein (GFP), DsRed; radioactive labels, e.g., $^{13}C$, $^{131}I$, $^{125}I$, $^{3}H$; chemiluminescent labels, e.g., luminol; enzyme labels, e.g., alkaline phosphatase, horseradish peroxidase, glucose oxidase, beta-galactosidase; FRET labels, e.g., europium, in which the detectable label is a FRET donor which interacts via FRET with a FRET acceptor incorporated into a given substrate; biotin label and strepavidin label for the subsequent binding of biotin and strepavidin, wherein either biotin or strepavidin is present on one or the other member of binding pair of molecules. When an enzyme is used as the labeling substance, detection is performed using a suitable substrate depending on the enzyme used. For example, if peroxidase is used as an enzyme label, the substrate o-phenylenediamine (OPD), tetramethyl benzidine (TMB), or the like, is used. If alkaline phosphatase is used as an enzyme label, the substrate p-nitrophenyl phosphate (PNPP), or the like is used.

In an embodiment, a fluorescent label is used and is detectable and quantifiable by flow cytometry methods. In another embodiment, an antibody against a cell-surface expressed target molecule or protein is detectably labeled with a fluorescence label and the binding or non-binding of the antibody to the cell-surface expressed target molecule or protein is determined, thereby allowing, in turn, detection and quantification of the level of the target molecule or protein on the cell surface. In another embodiment, a labeled secondary antibody is used, which specifically binds to the antibody that binds to the cell-surface expressed target molecule.

Examples of ligand binding proteins or receptor proteins as referred to herein include, without limitation, growth factor receptors, hormone receptors, enzyme receptors, Fc receptors, metabolic enzyme receptors, neurotransmitter receptors, chemokine receptors, cytokine receptors, lymphokine receptors, interleukin receptors, tumor antigen receptors, tumor suppressor antigen receptors (e.g., p53, Rb, k-Rev, DCC receptors), multidrug resistance protein receptors, coagulation factor receptors (e.g., Factor VII, Factor VIII, Factor IX receptors), trophic factor receptors, cell recognition or stimulatory molecule receptors, apolipoprotein receptors, and the like. Particular binding proteins or receptors include, without limitation, receptors in receptor families such as EGFR, ErbB-1R, HER1, HER2, aFGFR, bFGFR, NGFR, VEGFR, FltR, TGFR, TGFR-α-1, TGFR-β, TNFR (α), BDNFR, insulin receptor, insulin-like growth factor receptor (IGFR), PDGFR, HGFR, TRKR, BDNFR, CNTFR, GMFR, NT3R, NT5R, HARPR/pleiotrophinR, TIE receptors, Eph receptors, DDR receptors, ROR receptors, LTK receptors, AXL receptors, RET receptors, TOLL-like receptors; hormone receptors, such as steroid hormone receptors, thyroid hormone receptors, melatonin receptors, adrenergic receptors; peptide receptors, e.g., receptors for amylin, angiotensinogen, angiotensin, atrial natriuretic peptide, brain natriuretic peptide, calcitonin, corticotropin, erythropoietin, endothelin, enkephalin, follicle stimulating hormone, gastrin, ghrelin, glucagon, human chorionic gonadotropin, inhibin, leptin, luteinizing hormone, melanocyte stimulating hormone, oxitocin, pancreatic polypeptide, parathyroid hormone, prolactin, prolactin releasing hormone, rennin, secretin, somatostatin, thrombopoietin, thyroid stimulating hormone, thyrotropin releasing hormone; or GP130 or IL6 receptors. Also included are cell surface molecules that bind and/or interact with virus proteins and peptides. The foregoing is not meant to be an exhaustive list; other receptors that may find use in the invention will be understood to be useful by one having skill in the art. The ligand binding molecules, or receptor proteins, are preferably expressed on the cell surface and may be membrane receptors or transmembrane receptors. The ligand binding proteins may be modified, post-translationally modified or non-post-translationally modified, glycosylated or non-glycosylated. In an embodiment, a binding molecule or antibody as described herein specifically recognizes and binds to the ligand binding protein, or receptor protein. Encompassed herein are the nucleic acid sequences (DNA and RNA) and genes which encode the binding molecules, receptor proteins, or fragments or portions thereof.

Examples of cognate ligands (ligand proteins or antigens), which are recognized and bound, preferably specifically recognized and bound, by ligand binding proteins or receptor proteins, include, without limitation, the cognate ligand partner(s) of each of the above-listed, exemplary receptors. For example, ligands, such as growth factors, hormones, enzymes, metabolic enzymes, lipid transfer proteins, neurotransmitters, chemokines, cytokines, lymphokines, tumor-associated antigens, tumor suppressor antigens (e.g., p53, Rb, k-Rev, DCC), multidrug resistance proteins, coagulation factors (e.g., Factor VII, Factor VIII, Factor IX), cell recognition molecules, cell stimulatory molecules, and the like. More specifically, nonlimiting examples of ligand proteins (or peptides) include EGF, aFGF, bFGF, VEGF, Flt, TGF-β, TNF (TNF-α, TNF-β), NGF, insulin, insulin-like growth factor (IGF), PDGF, HGF, TRK, BDNF, CNTF, GMF, NT3, NT5, HARP/pleiotrophin. Such cognate ligands may be soluble or membrane-bound. The ligand proteins may be modified, post-translationally modified or non-post-translationally modified, glycosylated or non-glycosylated. In an embodiment, a binding molecule or antibody as described herein specifically recognizes and binds to a cognate ligand (protein). In an exemplary embodiment, the ligand protein is human tumor necrosis factor-α (hTNF-α). Also included are virus proteins and peptides which bind and/or interact with cell surface molecules. Encompassed herein are the nucleic acid sequences (DNA and RNA) and genes which encode the cognate ligands, ligand proteins or antigens, or fragments or portions thereof.

It will be understood that isolated nucleic acids (genes) encoding binding molecules such as antibodies, ligand binding proteins, receptors, ligand proteins, or any target protein according to the invention, can be inserted into appropriate vectors, which are used to transfect, transduce, or infect suitable host cells, particularly for subsequent expression in the cells, using methods known to the skilled practitioner in the art. The nucleic acids can be deoxyribonucleic acid (DNA) or ribonucleic acid (RNA) and can comprise naturally occurring sequences and sequences of synthetic or artificial origin. Suitable nucleic acids can include genomic DNA, cDNA, mRNA, tRNA, rRNA, hybrid sequences, synthetic or artificial sequences, or semi-synthetic or semiartificial sequences. The nucleic acids sequences can be eukaryotic or mammalian and of human origin or of non-human origin, e.g., animal or plant. In some cases, the nucleic acid sequences can be bacterial, viral, yeast, etc.

Such nucleic acids encoding a target protein, or binding molecule, or antibody, can be obtained by conventionally known techniques and methods practiced by those having skill in the art. Illustratively, nucleic acid sequences encoding proteins of interest can be obtained by screening nucleic acid/sequence libraries or gene banks, by chemical synthesis, or by a combination of methods including chemical or enzymatic modification of sequences obtained by screening nucleic acid/sequence libraries, cloned nucleic acids (DNA), or gene banks. Nucleic acid sequences encoding vast numbers of proteins of interest, including ligand binding molecules (cell-membrane associated), ligands and immunoglobulins, along with the encoded protein sequences, are available to the practitioner through public databases, such as the National Center for Biotechnology Information (NCBI), accessible via the worldwide website (ncbi.nlm.nih.gov), and through nucleotide and protein databases such as GenBank, RefSeq, or UniProtKB/Swiss-Prot. In addition, full length immunoglobulin libraries, e.g., human IgG, and immunoglobulin domain libraries are commercially available to one skilled in the art.

Suitable vectors include expression vectors that are expressible in mammalian or eukaryotic cells as host cells. Such vectors allow for the proper expression, cellular processing and production of members of a protein binding pair (e.g., a ligand binding molecule and its cognate ligand). In general, an expression vector encompasses any DNA cloning vector recombinant construct comprising a nucleic acid sequence to be expressed operably linked to a suitable control sequence capable of allowing the expression and control the transcription of the inserted nucleic acid in a suitable host. Such vectors, or plasmids, may be readily modified to construct expression vectors that produce the desired sequence in a variety of host organisms, including, e.g., E. coli, Sf9 (for baculovirus), yeast and mammalian cell hosts.

Vectors also relate to recombinant DNA cloning vectors, which are autonomously replicating constructs, which may include, without limitation, plasmids, phages, and viruses, comprising a DNA molecule to which one or more additional nucleic acids have been added.

Nonlimiting examples of vectors include viral vectors (e.g., lentivirus, modified form of HIV-1, adenovirus, adeno-associated virus vectors for infecting or transducing cells), phage particles, plasmid vectors, eukaryotic expression vectors, prokaryotic vectors, wherein the nucleic acid, including heterologous sequence(s) encoding a protein of interest, may or may not integrate into the host cell's genome. Within the vectors, the nucleic acid sequence or gene to be expressed and produced in a cell is operably linked to a control sequence in a manner allowing for expression, e.g., transcription and translation, of the nucleic acid sequence or gene in a host cell. Control sequences are known to those in the art and are selected to express the nucleic acid encoding the protein of interest, e.g., a ligand binding protein or receptor, a ligand protein, or a binding molecule, e.g., an antibody according to the invention, and to control the transcription. Such control sequences include, but are not limited to, a polyadenylation signal, a promoter (a natural or synthetic promoter), e.g., gene promoters such as CMV, RSV, MLP, E1A, etc., or an enhancer to effect transcription, an optional operator sequence to control transcription, a locus control region or silencer to allow tissue-specific transcription, a sequence encoding suitable ribosome binding sites on the mRNA, sequence(s) for stabilizing mRNA, sequences that control termination of transcription and translation.

Other sequences can be included with, or operably linked to, the nucleic acid or gene to be expressed in a vector, as will be appreciated by one skilled in the art, such as detectable or selectable biomarker sequences, tag sequences, selectable marker sequences, e.g., antibiotic resistance sequences, etc, or cellular signal sequences (e.g., either natural to the gene product or artificial, positioned upstream of the gene of interest and which directs the gene product synthesized into the secretion pathways of the host cell). Further, the expressed proteins may be additionally modified by including activation sequences, regulation sequences, organelle retention signal sequences, etc.

The technology and methods described herein relate are applicable to mammalian or eukaryotic cell expression systems and mammalian or eukaryotic host cells or cell lines for expression, activity and function of the components of the methods. It will be apparent to the skilled practitioner to use a cell line that has the capability of expressing a selected or desired ligand binding protein or receptor, or ligand, or target protein at the cell surface. As described herein, a given ligand protein may be engineered to be expressed within the cell membrane and/or on the cell surface. Eukaryotic expression systems are not limited for use in a particular host cell. A variety of eukaryotic host cells are available, for example, from depositories such as the American Type Culture Collection (ATCC), Manassas, Va., and may be used with a variety of vectors. The selection of a host cell is related to the character of the expression vector used and will be known to one skilled in the art. Nonlimiting examples of eukaryotic or mammalian cells and cell lines suitable for use in the methods of the invention include T-cell lines, e.g., Jurkat cells and JLTRG-R5 cells described herein; HEK293 cells, COS cells, CHO cells, B-cell lines, T-cell lines, etc. Cultured cell populations or cell lines can be developed or established from tissue or organ explants or immortalized cells. In an embodiment, the cell line is a human or human-derived cell line. In an embodiment, the cell line is a non-human primate cell line or a non-human primate-derived cell line. In an embodiment, the cell line is from or derived from a non-human species or a non-human primate species.

The expression and production of protein sequences composed of amino acids by recombinant techniques is well known and can be carried out by the skilled practitioner using conventional and standard methods. (See, e.g., Sambrook, J., Fritsch, E. F. and Maniatis, T., 1989, Molecular Cloning: A Laboratory Manual and later editions, e.g., 1991, 2001 and 2012 (J. Sambrook)). In general, the recombinant preparation of a protein, or a fusion protein which harbors additional sequence, such as a retention signal or tag, is carried out by either selecting the desired native nucleic acid sequence, e.g., DNA sequence, or by modifying a native DNA sequence, by transforming the DNA sequence into a suitable host and expression of the native or modified DNA sequence to form the desired protein sequence. A vector for expressing a protein can be introduced into a host cell using any suitable method, e.g., transformation, electroporation, transfection using calcium chloride, rubidium chloride, calcium phosphate, DEAE dextran, or other substances, microprojectile bombardment, lipofection, infection, or transduction. Methods for introducing DNA into a host cell by one of the foregoing processes are found, for example, in Sambrook, J., 1989, supra.

The recovery or isolation of the desired protein can be performed using methods and procedures that are standard in the art, including separating the host cells from the medium by centrifugation or filtration, if necessary after disruption of the cells, precipitating the proteinaceous components from the supernatant using a salt, e.g., ammonium sulfate, followed by purification using a number of chromatographic techniques, e.g., ion exchange chromatography, affinity chromatography or similar, known procedures.

Methods for Intracellular Selection and Screening of Binding Molecules

Provided herein are methods for selecting and screening for binding molecules, or genetically diversified binding molecules, within a cell. The binding molecules, which bind or interact with a target molecule within a cell, may have optimal binding properties and/or activity toward the target molecule. Encompassed by the methods is the intracellular localization and retention of binding molecules, as well as target molecules, which allows for the subsequent selection of a binding molecule that specifically binds to a target molecule within an intracellular organelle or compartment in the cell. Preferred but nonlimiting examples of suitable binding molecules are antibodies, or a binding fragment or portion thereof, antibody domains, e.g., $V_L$ and $V_H$, and libraries thereof.

In an embodiment of the invention, an antibody or a member of a genetically diversified antibody population, or a binding fragment or portion thereof, having a specific binding activity for a target molecule is effectively expressed, matured and selected in a cellular environment that also harbors its target molecule, thereby providing a convenient technique for antibody detection, selection and recovery based on the co-expression of the antibody as binding molecule and its target antigen within one cell. Thus, an advantage of the present selection methods is that only a single cell is needed to express an antigen binding molecule, e.g., an antibody, or a member of a diversified library or population of antigen binding molecules or antibodies, as well as its target antigen, and to select for the binding molecule or antibody that specifically and/or optimally binds to its target. In addition, such single cell methods of generating and selecting an antibody from a diversified antibody population advantageously do not involve ribosomal or nucleic acid display, or phage or cell display systems and do not require the use of particular B-cell lines harboring enzymes such as AID; nor do they involve conventional affinity maturation, receptor editing, or somatic hypermutation techniques. The cell-based methods of the invention can be used to select those antibodies or diversified antibodies that show optimal properties of binding and/or interaction with a given target molecule or antigen all expressed within the same cell, wherein that same cell can be assayed to determine the binding properties of an expressed antibody, and selected for recovering a desired antibody.

Several compartments within the secretory pathway are capable of retaining a protein. For each compartment, a particular amino acid sequence can be fused or coupled to a protein (or "signal sequence") to retain the protein in the specific cellular location. Illustratively, for retention of a protein in the ER, the KDEL (SEQ ID NO:1) amino acid sequence may be employed; for retention of a protein in the trans-Golgi network, the YQRL (SEQ ID NO:2) amino acid sequence may be used; for retention of a protein in peroxisomes, the SKL amino acid sequence may be used; for retention of a protein in the plasma membrane of a cell, an H-Ras or K-Ras CAAX (SEQ ID NO:3) amino acid sequence may be used; for retention of a protein in mitochondria, MSVLTPLLLRGLTGSARRLPVPRAK (SEQ ID NO:4) amino acid sequence may be used; and for retention of a protein in the nucleus, the PPKKKRKV (SEQ ID NO:5) amino acid sequence may be used. The ER with its tubular architecture combined with the precise channeling of the proteins through the secretory pathway and with the presence of ER-resident chaperones makes this organelle an optimal intracellular location for the retention of proteins. It will be appreciated that post-translationally modified, e.g., glycosylated, or glycan-containing proteins will typically be retained in the Golgi if such proteins comprise a Golgi retention sequence such as YQRL (SEQ ID NO:2), while non-glycosylated proteins will typically be retained in the ER, if such proteins comprise an ER retention signal such as the KDEL amino acid sequence (SEQ ID NO:1).

In an embodiment, a method is provided to capture or retain within a cell a target protein that is recognized and bound by a binding molecule, e.g., an antibody, for selection, in accordance with the selection methods of the invention. In a related embodiment, a method is provided to specifically select one or more antibodies that neutralize, interrupt, block, disrupt, or eliminate an interaction between a ligand binding receptor and its cognate ligand, wherein either the ligand binding receptor or the ligand is the target protein which is specifically recognized and bound by the antibody, and wherein the target protein is retained with the cell, thereby localizing the target protein intracellularly and allowing binding access by the antibody within the cell.

In an embodiment, the binding molecule, e.g., an antibody or a binding portion thereof, specifically targets and binds to the receptor protein, which is expressible on the cell surface. In an embodiment, the binding molecule, e.g., an antibody or a binding portion thereof, specifically targets and binds to the cognate ligand protein. In an embodiment, the cognate ligand protein is molecularly engineered to be expressible on the cell surface. In various embodiments as described herein, either the binding molecule, e.g., an antibody, or the target protein, comprises an ER retention signal, which is the carboxy-terminal sequence KDEL (SEQ ID NO:1), that prevents proteins from following the normal secretory pathway by inducing the retrograde transport from cis-Golgi, thereby effectively retaining the protein in the organelle. The binding molecule, e.g., an antibody, or the target protein may also be retained in other intracellular organelles or compartments by engineering them to express, or molecularly fusing them to, other signal sequences, for example, the YQRL (SEQ ID NO:2) sequence for retention in the Golgi, the SKL sequence for retention in peroxisomes, or the CAAX (SEQ ID NO:3) sequence for retention in the plasma membrane.

Selection Methods Based on a Receptor-Negative Cell Phenotype

One embodiment of the invention relates to a selection method of the invention in which a receptor-negative phenotype of a cell is generated. In such an embodiment, a cell line is molecularly engineered to express both a cell-surface-expressed receptor protein and its cognate ligand protein, which is fused to the KDEL retention signal sequence (SEQ ID NO:1) to retain the cognate ligand protein in the ER. The cognate ligand protein is expressed and retained in the ER by virtue of the KDEL sequence (SEQ ID NO:1). Within the ER, the cognate ligand protein interacts with its expressed receptor protein. Because the cognate ligand protein was retained in the ER, the receptor protein, through its interaction with the ER-retained cognate ligand, is also consequently retained within the ER in the cells. Accordingly, the receptor protein is not transported from the ER and expressed or displayed at the cell surface as it typically would have been absent a retention signal. Retained in the cell organelle, the receptor protein is not detectable by a detectably labeled molecule specific for the receptor protein, thereby creating a receptor-negative phenotype for the cell. The receptor-negative phenotype of the cells containing the ligand binding receptor protein bound to its cognate ligand and retained in the ER can be assessed by flow cytometry utilizing a detectable antibody directed against the cell-surface ligand binding receptor protein. This aspect can be visualized and exemplified advantageously through the interaction of the ligand binding receptor, hTNF-α receptor I, and its cognate ligand, hTNF-α, as schematically depicted in FIGS. 1A and 1B.

As exemplified herein, a Jurkat cell line expresses a representative receptor protein, i.e., hTNF-α receptor I, that is displayed on the surface of the cell. As described in Example 1 herein, JLTRG R5 cells express the hTNF-α receptor I and can be readily transduced to express and retain certain proteins intracellularly in accordance with the invention. For example, the JLTRG R5 cell line can be transduced to express the ligand protein hTNF-α, fused to a KDEL sequence (SEQ ID NO:1) (hTNF-α-KDEL) ("KDEL" disclosed as SEQ ID NO:1). The hTNF-α-KDEL fusion protein ("KDEL" disclosed as SEQ ID NO:1) binds to its hTNF-α receptor I protein binding partner intracellularly, and both proteins are retained in ER. The presence and expression of the ligand protein can be further efficiently detected, for example, by the expression of a detectable label, e.g., DsRed, inside the cell. The receptor protein, due to its retention in ER via binding to its cognate ligand, which is also retained in the ER, is not detected at the surface of the cell using flow cytometry and a labeled anti-hTNF-α receptor I antibody. (FIGS. 1A and 1B), thereby creating a receptor-negative selection cell phenotype.

Selection Methods Based on a Receptor-Positive Cell Phenotype

Another embodiment of the invention relates to a selection method in which a receptor-positive phenotype of a cell is generated. This embodiment relates to the selection of a binding molecule that specifically binds a target antigen/protein. To select a binding molecule according to this embodiment, nucleic acid encoding a binding molecule is introduced into a cell line, such as the above-described cell line which expresses a cell surface expressed receptor protein. In an embodiment, the cells are transduced with lentiviral particles comprising a binding molecule, i.e., a specific antibody, or a binding portion thereof, e.g., a $V_L$ domain, that recognizes and binds to a target antigen. In an embodiment, the particles introduce into the cells one of a plurality of binding molecules, such as genetically diversified binding molecules or antibodies, one or more of which may have been genetically modified to possess optimal binding properties and to bind with high specificity or affinity to a target antigen/protein and be selected for. The target antigen of the binding molecule or antibody can be either the cell surface expressed receptor protein or the ligand of this receptor protein fused to the ER retention sequence for retention in the ER. Upon binding to either the receptor protein or the ligand protein target in the ER of the cell, the expressed antibody blocks and disrupts the interaction between the receptor protein and its cognate ligand.

The blocking of the binding of the receptor protein to its cognate ligand due to the presence and binding of the binding molecule or antibody in the ER results in the transit and release of the receptor protein from the ER and allows for its expression at the surface of the cell. The resulting receptor-positive cell phenotype can be assessed by flow cytometry utilizing a detectable antibody directed against the cell-surface ligand binding receptor protein expressed on the surface of the cell. The cell may further be engineered to contain a detectable label, such as DsRed, that is useful for selecting and sorting cells via flow cytometry. This aspect is schematically depicted in FIGS. 1C and 1D. A receptor-positive cell phenotype is determined by measuring a quantifiable level of receptor protein on the cell surface by virtue of its being bound by a detectably labeled antibody. The binding molecule, e.g., antibody, can be recovered or isolated from the cell and, optionally, further purified for use by employing standard techniques and methods. For example, the cells that have been sorted as being positive for binding by anti-receptor antibody and/or cell staining, based on fluorescence detection and mean fluorescence intensity, can be seeded and growth expanded. Such cells will harbor the binding molecule or antibody that bound to target antigen. DNA can be extracted from the expanded cell population, and the binding molecule or antibody can be isolated and further characterized using conventional methods practiced by those in the art.

As specifically demonstrated in FIGS. 1C and 1D using a representative, exemplified target antigen, the JLTRG R5 cell line is transduced with lentiviral particles encoding the $V_L$ domain (or region) of antibodies that target and bind hTNF-α receptor I. The binding of one or more of the transduced $V_L$ antibody domains blocks or disrupts the interaction between the ligand binding receptor and its cognate ligand, thereby releasing the receptor from the ER and permitting its expression on the surface of the cell. In FIG. 1C, the $V_L$ antibody, i.e., $V_L$ binding domain, is shown to bind to the hTNF-α ligand protein portion of the hTNF-α-KDEL ligand fusion protein ("KDEL" disclosed as SEQ ID NO:1), thereby blocking the interaction of hTNF-α with the hTNF-α receptor I in the ER and allowing the hTNF-α receptor I protein to be transported to and expressed on the cell surface. In FIG. 1D, the $V_L$ antibody is shown to bind to the hTNF-α receptor I protein, thereby blocking the interaction of hTNF-α with hTNF-α receptor I in the ER and allowing the hTNF-α receptor I protein to be transported to and expressed on the cell surface. Such cell-surface displayed receptor is detectable using a detectable binding agent, such as a receptor-specific antibody. It will be appreciated that in a case in which the antibody, or a binding molecule, binds specifically to a receptor protein as its target and permits the receptor protein to transit through the ER and be expressed in the plasma membrane of the cell due to the disruption or neutralization of the binding of the receptor protein to its cognate ligand that is retained in the cell organelle, the binding of the antibody, or binding molecule, to the receptor protein optimally does not concomitantly impede or block the expression of the receptor protein in the cell membrane.

To determine if a binding molecule such as an antibody, e.g., a $V_L$ antigen binding domain, has blocked, inhibited, neutralized, or disrupted the receptor-cognate ligand interaction by specifically binding to the receptor or to the ligand in the cell organelle, cells are exposed to a detectably labeled antibody directed to the expressed receptor protein, e.g., hTNF-α receptor I, and can be sorted in a flow cytometer (cell sorter). Typically, fluorescence detection is used. In addition, the cells may also be constructed to contain a detectable label to facilitate sorting, such as DsRed, GFP and the like. Illustratively, the measurement of the level of labeled antibody bound to ligand binding receptor protein on the cell surface indicates that a specific binding molecule, e.g., antibody or $V_L$ domain, within the cell has bound either the ligand binding receptor, or its cognate ligand, and has prevented, disrupted, neutralized, or blocked the interaction of the ligand binding receptor to its cognate ligand in the organelle, such as the ER. The blocking of the receptor-ligand interaction permits the receptor to exit the ER and be expressed on the cell surface where it can be detected by a detectably labeled specific binding molecule. Analysis of the cells is conducive to high throughput assays, including FACS and flow cytometry analyses and variations thereof.

In one illustrated embodiment, specific antibody, or a binding fragment or portion thereof, a cell-surface expressible ligand binding receptor protein and its cognate ligand fused to an ER retention signal are co-expressed in the same cell. At the time that the three types of proteins are present in the ER, the antibody, which, in this embodiment, is directed to the cognate ligand, specifically targets and binds to the cognate ligand retained in the ER. Consequently, the interaction between the receptor protein and its cognate ligand within the ER is blocked, neutralized, or disrupted by the antibody bound to cognate ligand as target, thereby effectively releasing the cognate ligand from its interaction with the receptor protein in the ER and liberating the receptor protein, allowing its transit from the ER to the plasma membrane of the cell where it is expressed on the cell surface. A detectably labeled antibody directed against the cell-surface expressed receptor protein is able to bind the receptor protein on the cell surface and serves to quantify the level of expressed receptor protein. The detection of expressed receptor on the cell surface is indicative of the presence of a binding molecule, e.g., an antibody, or a binding fragment or portion thereof, expressed in the cell. Conventional methods can be employed to recover and isolate the binding molecule, or antibody, and amplify its expression. Thus, the binding molecule having specific binding properties is selected through the method of the invention.

In another illustrated embodiment, specific antibody, or a binding fragment or portion thereof, a cell-surface expressible ligand binding receptor protein and its cognate ligand fused to an ER retention signal are co-expressed in the same cell. At the time that the three types of proteins are present in the ER, the antibody binds not to the cognate ligand retained in the ER, but instead is directed to and specifically targets the ligand binding receptor protein. In this case, the interaction between the receptor protein and its cognate ligand is still blocked, neutralized, or disrupted by antibody binding. In this embodiment, the receptor protein is similarly effectively released from its interaction with its cognate ligand retained in the ER. Accordingly, the receptor protein can transit from the ER and be expressed on the cell surface where it can be detected as described. For each of these embodiments, a detectably labeled antibody directed against the extracellularly-expressed portion of the cell-surface receptor protein can bind and be used to quantify the level of cell-surface expressed receptor protein. In accordance with the selection method, the gene encoding a binding molecule or antibody that has bound to either the receptor protein or the cognate ligand within the cell can then be isolated or recovered from the cell as desired. See, e.g., Example 4 herein. For example, the genes can be isolated by polymerase chain reaction or isolated from cellular DNA by cleavage using suitable restriction enzymes recognizing cleavage sites surrounding the gene of interest. In addition, not only can DNA encoding the binding molecule or antibody of interest be recovered from a pool of cells expressing the encoding DNA, but single clones expressing the DNA can be detected by FACS analysis, and the encoding DNA can be extracted from a single clone.

In another embodiment, a method is provided to select antibodies that bind to a specific target within a cell. Such antibodies preferably show optimal binding to a specific target, and preferably have high affinity or binding specificity. As a representative example of the method, a cell line expressing a desired target molecule (protein) capable of being expressed at the surface of the cell is constructed. To this end, the cell line is engineered to express and produce the target protein, which, in turn, is molecularly engineered, as necessary, to be expressed in the plasma membrane of the cell. For example, the target protein can contain, or be constructed to contain, a transmembrane domain and a cytoplasmic domain, as well as its extracellular domain, for appropriate expression (and detection) in the plasma membrane. Nucleic acid sequences encoding antibodies are introduced into the cell line, e.g., via transduction by lentivirus particles. Accordingly, the cells are transduced with lentiviral particles containing nucleic acid sequences encoding antibodies (e.g., $V_L$ and/or $V_H$ binding domains) fused to the KDEL signal sequence (SEQ ID NO:1) for retention in the ER. At a time when antibody and target protein are expressed and present in the ER, the antibody is able to bind specifically to its target molecule (protein). In accordance with the method, the target protein is retained in the ER by virtue of its being bound by the ER-retained antibody. As a consequence, the antibody-bound target molecule (protein) is unable to transit from the ER, and the expression level of the target molecule (protein) at the surface of the cell is decreased or nil. Accordingly, virtually no detection of cell-surface-expressible target protein results.

A decrease in expression of a target molecule (protein) on the cell surface is able to be determined relative to a positive control, e.g., cells expressing the target molecule on the surface, or relative to cells that express the target molecule (protein), but that are not transduced with lentiviral vectors encoding the target molecule (protein)-specific antibodies harboring an ER retention signal. In the absence of such expressed antibody in the control cells, the cell-surface expressible target molecule (protein) is not retained in the ER, is transported to and expressed in the plasma membrane, and can be detected by detectably labeled agents on the surface of the cell. Alternatively, a control may be included in which lentiviral vectors carrying nucleic acid sequences encoding an irrelevant or non-specific protein, e.g., antibody, or a binding portion thereof, can be used in parallel to transduce cells for comparative purposes. In a manner similar to that of the other embodiments described herein, the surface receptor positive or negative phenotype can be detected, for example, via flow cytometry, by employing a detectable antibody specific to the target molecule (protein), and thereafter, cells expressing the desired antibody can be selected and antibody recovered.

Figures 1A, 1B, 1C, 1D:
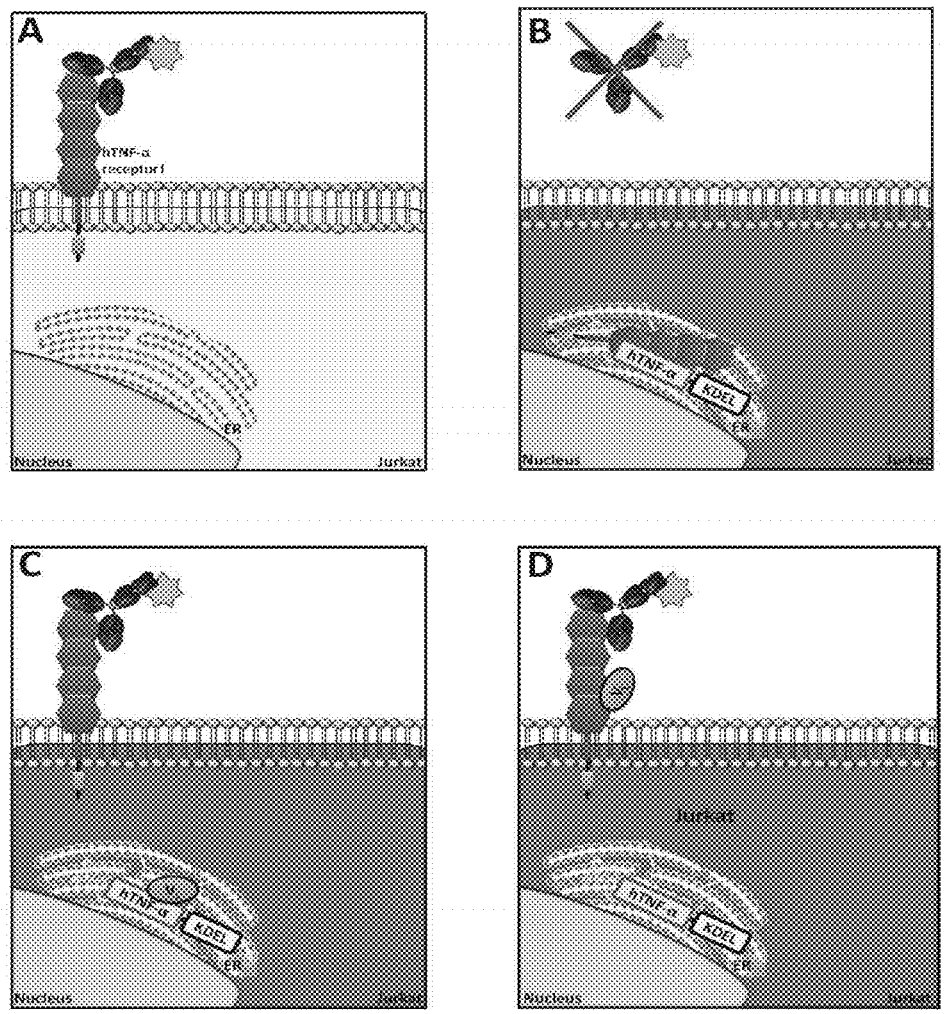
FIGS. 1A-1D show a schematic depiction of an aspect of the invention as described herein in which a KDEL-tagged ligand protein ("KDEL" disclosed as SEQ ID NO:1) is retained in the endoplasmic reticulum of the cell. Briefly, as shown.
Figure 2A:
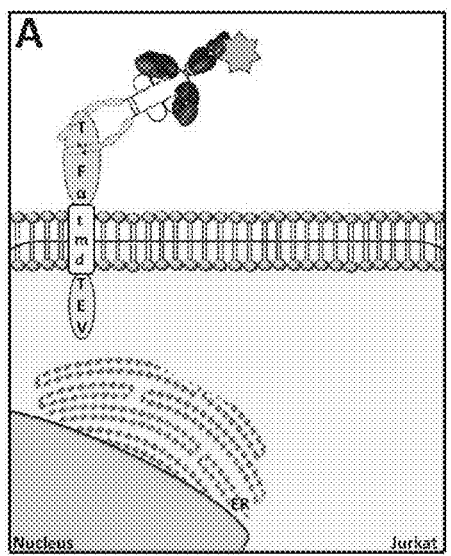
FIGS. 2A and 2B show a schematic representation of an antibody ($V_L$ domain) tagged with the KDEL sequence (SEQ ID NO:1) to retain the antibody in the ER.
Figure 2B:
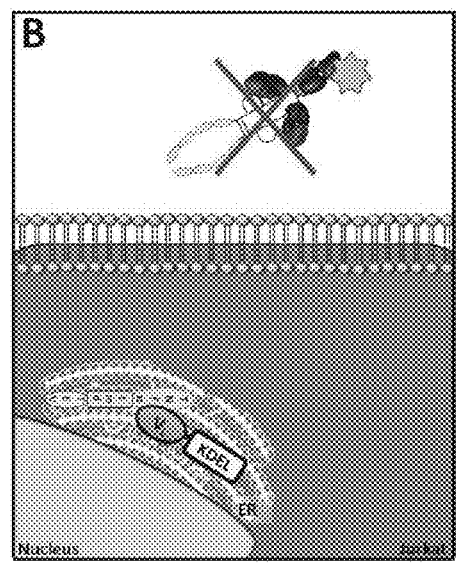

FIGS. 2A and 2B demonstrate and exemplify an embodiment of the selection methods of the invention. As depicted and exemplified, a cell line is constructed to express hTNF-α, a representative cell surface-expressed target protein, having an extracellular domain fused to a transmembrane domain and a TEV sequence, a representative cytoplasmic domain for appropriate anchoring of the protein in the cell membrane. In the figure, the expressed hTNF-α is detectable at the surface of the cell using a labeled antibody directed against hTNF-α. (FIG. 2A). The cell is transduced with lentiviral particles expressing the L chain variable regions ($V_L$) of anti-hTNF-α antibodies fused to the KDEL sequence (SEQ ID NO:1) ($V_L$ (antibody)-KDEL ("KDEL" disclosed as SEQ ID NO:1)) resulting in antibody retention in the ER, as described in the Examples herein. If a $V_L$ antibody specifically binds and/or binds with high affinity to the target protein in the ER, the complex comprising antibody bound to the hTNF-α target protein is retained in the ER, and the hTNF-α target protein is no longer detected or detectable at the surface of the cell. (FIG. 2B) The resulting cellular phenotype, i.e., the presence or absence of the target protein at the cell surface, is detected by flow cytometry employing a detectably labeled antibody directed against the target protein. As shown in FIG. 2A, the cell surface-expressed hTNF-α protein is detected at the surface of the cell by an antibody that specifically recognizes and binds the cell surface-expressed protein. In FIG. 2B, because the cells are transduced with antibody-KDEL molecules ("KDEL" disclosed as SEQ ID NO:1), the antibody that binds to hTNF-α protein retains this target protein in the ER, and the hTNF-α protein is no longer detected at the surface of the cell.

The platform technology and methods of the invention are particularly amenable to a high throughput screening or detection format. For example, flow cytometry is suitable for detecting and screening engineered cells that express or do not express a given protein, e.g., a target protein such as a ligand binding receptor protein or a ligand, on the cell surface; which express an antibody or antibodies or interest; or which contain retained proteins in a cell organelle. Other screening or detection methods suitable for use include immunoassay methods, such as enzyme linked immunosorbant assays (ELISA), radioimmunoassay (RIA), fluoroimmunoassay (FIA), chemiluminescent immunoassay (CIA), fluorescence resonance energy transfer (FRET), homogeneous time resolved fluorescence (HTRF), luminescent assay ("glow"-type signals), evanescent wave analysis, etc., which may be performed by conventional methods as known by those having skill in the art.

Intracellular Methods for Genetic Diversification of Antibody Binding Molecules

Zinc fingers, e.g., $Cys_2His_2$ zinc fingers, comprise the most common transcription factor family in organisms ranging from yeast to humans. Zinc finger proteins designed or purposefully re-engineered to contain certain DNA-binding specificities provide technology suitable for targeting functional domains to a gene of interest in various cell types. Zinc finger nucleases (ZFNs) provide a powerful tool for performing targeted genomic manipulation within a variety of cell types.

Zinc finger nucleases (ZFNs) are synthetic proteins containing an engineered DNA-binding zinc finger domain linked to a non-specific endonuclease domain. In particular, ZFNs may contain an engineered DNA-binding zinc finger domain fused to the DNA cleaving domain of the FokI restriction endonuclease. ZFNs can introduce double-stranded breaks (DSBs) that stimulate both homologous and non-homologous recombination processes that can be harnessed to perform genomic manipulation and result in genetic diversity and variation. These cellular processes can be harnessed to generate precisely-targeted in vitro or in vivo genomic edits with targeted gene deletions, i.e., knockouts, integrations, or other modifications. Targeting a double-strand break to a specific site in the genome with ZFNs has been used to disrupt permanently the genomic sequence surrounding the ZFN target site in a variety of eukaryotic organisms via imperfect DNA repair by nonhomologous end joining (NHEJ), (Ho M, Pastan I (2009), Methods Mol. Biol., 525: 337-352, xiv). Gene targeting is a method that can repair or inactivate any desired gene of interest. Gene targeting strategies use the introduction of a DSB into a genomic locus to enhance the efficiency of recombination, e.g., with an exogenously introduced homologous DNA "repair template". DSBs can stimulate recombination efficiency several thousand-fold, approaching gene targeting frequencies as high as 50%.

In accordance with the invention, the use of ZFNs and the molecular processes related thereto are used as a genetic approach to generate one or more, e.g., a population of, diversified antibodies, i.e., antibodies, or binding fragments or portions thereof, having diversity in their specific interactions and binding capabilities with target proteins and antigens. The diversity or variability resulting from directed cleavage and repair within the DNA encoding the CDRs of an antibody molecule can generate one or more diversified antibodies with specific and optimal binding properties, wherein the diversified antibodies have the potential to possess higher specificity, affinity, avidity, and the like, in interacting and binding with their target molecules/proteins and target antigens. In general, a diversified antibody or an optimum binding antibody from a population of diversified antibodies, or portions thereof, as described herein may be screened or selected for using methods known in the art, e.g., ribosomal or nucleic acid display, phage or cell display systems, or using particular B-cell lines harboring enzymes such as AID. Alternatively, a diversified antibody or an optimum binding antibody from a population of diversified antibodies, or portions thereof, can be conveniently and advantageously screened or selected for using the single cell selection methods described herein.

Accordingly, in another of its aspects, the invention provides methods of inducing variability in specific locations of binding domains of binding molecules, e.g., antibodies, using nucleic acid recognition sequences of zinc finger DNA binding proteins and zinc finger nucleases designed to bind to the recognition sequences. In an embodiment, zinc-finger recognition sites, i.e., nucleic acid sequences, are introduced into the established immunoglobulin CDR architecture of the variable domain of immunoglobulin heavy chains, for example, a human variable heavy chain domain ($hV_H$), and/or the variable domain of immunoglobulin light chains, for example, a human variable light chain domain ($hV_L$). Depending upon the extent of variability desired, zinc-finger recognition sequences can be introduced into one, two, or all three CDRs, i.e., CDR1, CDR2, CDR3, in either or both of the $V_H$ and $V_L$ domains of the heavy and light antibody chains, e.g., $V_H$ and/or $V_L$ domains.

The introduction of zinc-finger recognition sites into the CDR locus allows for targeted gene disruption induced by zinc-finger nucleases. The DNA-binding domains of individual ZFNs typically contain between three and six individual zinc finger repeats and can each recognize between about 9 to about 18 base pairs. If the zinc finger domains are perfectly specific for their intended target site, then even a pair of 3-finger ZFNs that recognize a total of 18 base pairs may target a single locus in a mammalian genome. The determination of suitable ZFN recognition sites, including finding zinc finger protein target sites and designing proteins, e.g., ZFNs, that target them, can be facilitated by available information in the art, for example, through publications and publicly available and interactive internet websites, such as are provided for use by the skilled practitioner, e.g., from the Laboratory of Carlos F. Barbas III, Ph.D., The Scripps Research Institute (TSRI), La Jolla, Calif. (worldwideweb.zincfingertools.org) and the Laboratory of Daniel Voytas, a member of The Zinc Finger Consortium, which provides publicly-available information on zinc finger design (worldwideweb.zincfingers.org).

As indicated in the "zincfingertools" website, significant progress has been made to date in the development of modular protein domains that recognize specific triplets of DNA sequence. These domains can be fused together to create proteins that can bind to a chosen DNA sequence. The $Cys_2$-$His_2$ zinc finger motif, identified first in the DNA and RNA binding transcription factor TFIIIA, is perhaps the ideal structural scaffold on which a sequence-specific protein might be constructed. A single zinc finger binding domain consists of approximately 30 amino acids with a simple $\beta\beta\alpha$ fold stabilized by hydrophobic interactions and the chelation of a single zinc ion. Presentation of the $\alpha$-helix of this domain into the major groove of DNA allows for sequence specific base contacts. Each zinc finger domain typically recognizes three base pairs of DNA, though variation in helical presentation can allow for recognition of a more extended site. In contrast to most transcription factors that rely on dimerization of protein domains for extending protein-DNA contacts to longer DNA sequences or addresses, simple covalent tandem repeats of the zinc finger domain allow for the recognition of longer asymmetric sequences of DNA by this motif. Since each zinc finger domain typically binds three base pairs of sequence, a complete recognition alphabet requires the characterization of 64 domains. The TSRI has taken a systematic approach toward generating a modular recognition alphabet using selection by phage display and refinement by site directed mutagenesis to prepare the zinc finger domains representing the 5'-GNN-3',5'-ANN-3' and 5'-CNN-3' subsets of this 64-member recognition code. Further, publications by the Barbas Laboratory have provided several 5'-TNN-3' domains and information on this recognition alphabet.

As will be understood by the skilled practitioner, the main parameters to optimize when designing a ZFP are typically the specificity and affinity for DNA binding. Illustratively, a 6-finger protein intended to recognize an 18 bp target site and constructed using the canonical TGEKP linker (SEQ ID NO: 47) provides an exemplary solution for endogenous gene regulation. Proteins that bind their target with an affinity of 10 nM or better are productive regulators; ZFPs with an affinity of 1 nM or better have optimal activity. The affinity for a ZFP can be determined by performing an Electrophoretic Mobility Shift Assay (EMSA). Publicly accessible, interactive information regarding zinc finger binding proteins facilitates the determination of particular recognition sites. In accordance with the present invention, recognition sites of the form (XXX)3N6(XXX)3, where "XXX" are triplets for which zinc fingers exist and "N" is any nucleotide. The ZFN1 through ZFN4 zinc finger nucleases described herein were created by this methodology.

In an embodiment of such methods, zinc-finger recognition sequences are introduced into one of the three CDRs in either or both of the $V_H$ and $V_L$ domains. In an embodiment, zinc-finger recognition sequences are introduced into two of the three CDRs, in any combination, in either or both of the $V_H$ and $V_L$ domains. In an embodiment, zinc-finger recognition sequences are introduced into all three of the CDRs, in any combination, in either or both of the $V_H$ and $V_L$ domains. In an embodiment, zinc-finger recognition sequences are introduced into at least one CDR in either or both of the $V_H$ and $V_L$ regions of the heavy and light antibody chains, respectively. In an embodiment, zinc-finger recognition sequences are introduced into each of CDR1 and CDR2 of the $V_H$ and $V_L$ regions of the heavy and light antibody chains, respectively. In an embodiment, zinc-finger recognition sequences are introduced into each of CDR2 and CDR3 of the $V_H$ and $V_L$ regions of the heavy and light antibody chains, respectively. In an embodiment, zinc-finger recognition sequences are introduced into each of CDR1 and CDR3 of the $V_H$ and $V_L$ regions of the heavy and light antibody chains, respectively. In an embodiment, zinc-finger recognition sequences are introduced into each of the CDRs, namely, CDR1, CDR2, or CDR3, of the $V_H$ and $V_L$ regions of the heavy and light antibody chains, respectively. In an embodiment, at least one recognition sequence is introduced into a given CDR. In an embodiment, two or more recognition sequences are introduced into a given CDR. In an embodiment, two recognition sequences are introduced into a given CDR. In an embodiment, two recognition sequences are introduced into two given CDRs, such as, for example, CDR1 and CDR3.

In a specific embodiment, the CDR1 and CDR3 sequences within the light-chain and heavy-chain variable domains contain different zinc-finger DNA binding protein recognition sequences. More specifically, each of CDR1 and CDR3 contains two different zinc-finger DNA binding protein recognition sequences. For the different target sites in each CDR, two zinc-finger protein (ZFP) DNA-binding domains, i.e., nucleic acid recognition sequences, each containing four zinc-finger motifs (recognizing a total of 24 base pairs), are assembled in vitro in accordance with published methods, e.g., Moore, M., Choo, Y. & Klug, A., Proc. Natl. Acad. Sci. USA 98, 1432-1436 (2001); Jamieson, A. C., Miller, J. C. and Pabo, C. O., Nat. Rev. Drug Discov., 2, 361-368 (2003). In total, four recognition sequences are introduced in the $V_H$ domain and four recognition sequences are introduced in the $V_L$ domain. The zinc-finger DNA binding protein recognition sequences are coupled to the DNA cleavage domain of the type IIS restriction enzyme, FokI, to produce novel ZFNs in which the location of DNA cleavage is determined by the DNA-binding specificity of the engineered ZFP domains (e.g., Urnov, F. D. et al., Nature 435, 646-651 (2005); Moore, M., Choo, Y. and Klug, A., Proc. Natl. Acad. Sci. USA 98, 1432-1436 (2001); Smith, J. et al., Nucleic Acids Res. 28, 3361-3369 (2000)).

Figure 3:
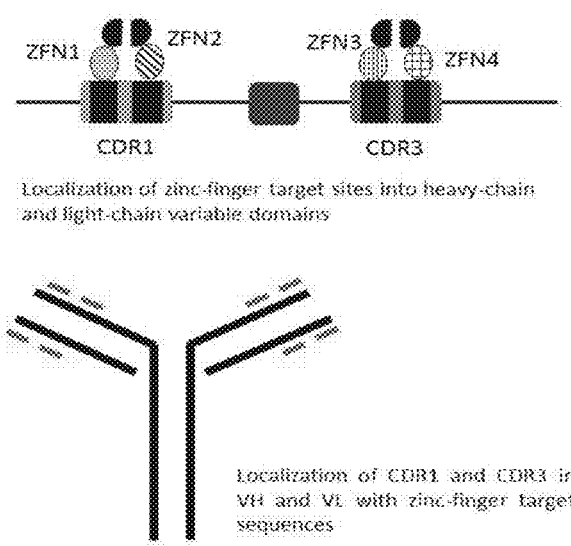
FIG. 3 shows the localization of zinc finger target sequences as introduced into the CDR regions, e.g., CDR1 and CDR3, of the human heavy chain variable domain ($V_H$) and the human light chain variable domain ($V_L$). The zinc-finger target sequences were introduced into the CDR region with three different sequence frames to suppress frame shift and a consequent lack of antibody production. The resulting human variable domains were reintroduced into human immunoglobulin type G1 (IgG1), resulting in a complete antibody protein with molecularly engineered CDR1 and CDR3 regions containing different zinc-finger recognition sites. In each CDR, two different zinc-finger recognition sites were positioned and were able to be recognized by two different zinc-finger-nucleases. CDR1 bones by molecular techniques to generate different antibody classes having diverse and variable binding specificities.
Figure 4:
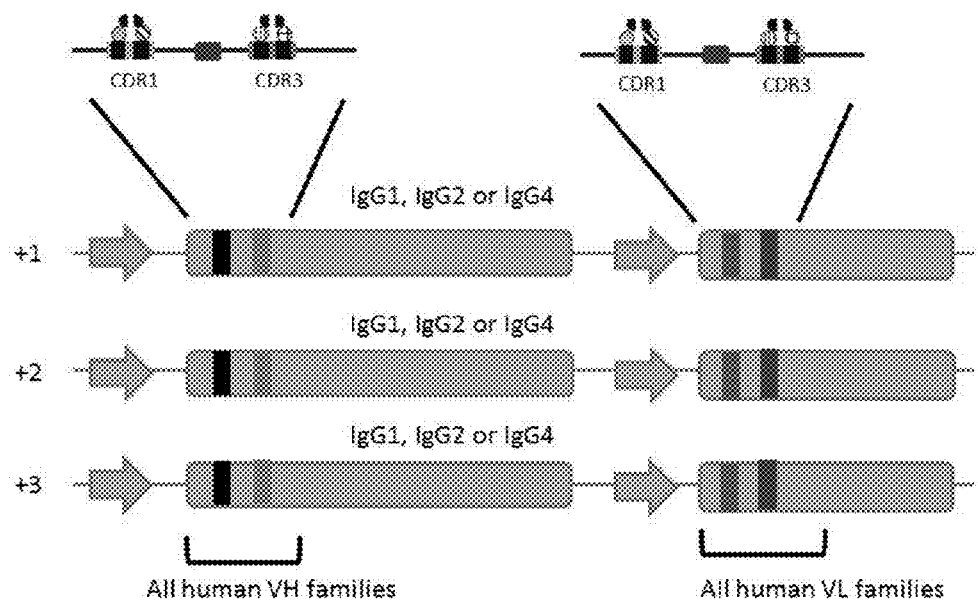

In a representative example, $V_H$ and $V_L$ region CDR1 and CDR3 comprising introduced zinc finger targeting sequences are shown in FIG. 3. The rectangular area between the CDR1 and CDR3 regions represents CDR2, which does not contain zinc finger target sequences in this instance. In a 5' to 3' direction, the following is a representative sequence of the CDR region (e.g., both CDR1 and CDR3) with two zinc finger targeting sequences represented by contiguous "Ns": 5' tactcaNNNNNNNNNNNNctgatNNNNNNNNNNNNttactca 3' (SEQ ID NO:6). The total number of amino acids in each of the CDR regions of $V_H$ and $V_L$ differ depending on the specific CDR, the specific antibody or type of antibody, and whether the CDR resides within the L or the H chain of an antibody. In general terms, a CDR comprises from about 6 to about 10 or 15 amino acids; however, CDRs of antibody molecules are well established and can be identified based on sequence information, including framework sequence information, as described, for example, by Wu, T. and Kabat, E. A., 1970, J. Exp. Med., 132:211-250; and Hood, L. et al., 1975, Ann. Rev. Genetics, 9:305-353.

It will be appreciated that the nucleic acid recognition sequences of zinc finger DNA binding proteins can be introduced into the CDRs outside of the $V_H$ and/or $V_L$ domains in which they typically reside. For example, the nucleic acid sequences encoding the CDRs, which may be isolated from a $V_H$ and/or a $V_L$ domain, can be molecularly engineered to contain the nucleic acid recognition sequences of zinc finger DNA binding proteins in the context of, e.g., a suitable plasmid or vector construct, or a nucleic acid expression cassette, as known in the art. A nucleic acid construct or a cassette can comprise one, two, or all of the CDRs, namely, CDR1, CDR2, and/or CDR3. The CDRs can be situated linearly or in tandem within the construct or cassette. The one or more CDRs, which have been modified to contain nucleic acid recognition sequences of zinc finger DNA binding proteins, can thereafter be introduced into $V_H$ and/or $V_L$ domains, i.e., the nucleic acid sequences encoding such domains, using conventional molecular techniques known to those in the art. Alternatively, the nucleic acid recognition sequences of zinc finger DNA binding proteins can be introduced into the CDRs as they naturally reside within the $V_H$ and/or $V_L$ domains. Accordingly, the $V_H$ and/or $V_L$ domain nucleic acid sequences comprising the CDR-encoding nucleic acid sequences are engineered using conventional molecular biology techniques to contain the nucleic acid recognition sequences of zinc finger DNA binding proteins within one or more of the CDR-encoding nucleic acid sequences, thus producing one or more modified CDRs. As will be understood by the skilled practitioner, the $V_H$ and/or $V_L$ domains comprising the one or more modified CDRs can be molecularly engineered as desired, such that they are operably expressed with suitable immunoglobulin H and L chain constant regions to produce a full-length antibody comprising modified CDRs.

In an embodiment, the zinc-finger target sequences are introduced into the CDR region with three different sequence frames to suppress frame shift and a consequent lack of antibody production. The resulting engineered human variable domains are reintroduced into human immunoglobulin G (IgG), for example, IgG1, producing a full-length antibody protein with variable regions containing artificial CDR1 and CDR3 engineered to include different zinc-finger recognition sequences or targeting sites. (FIGS. 3 and 4). In an embodiment, in each CDR, two different zinc-finger recognition sites are positioned such that the two different zinc finger recognition sites are recognized by two different zinc-finger-nucleases. In this representative case, CDR1 and CDR3 are thus targeted by this strategy to induce specific cleavage at these intra-CDR sequence sites. Depending on the extent of variability desired, CDR2 can remain in its native sequence, or it can be subjected to zinc-finger targeting, in a manner similar to that described for CDR1 and CDR3. In total, for a full-length IgG, a total of four different zinc-finger hotspots in the variable heavy-chain and four different zinc-finger hotspots in the variable light-chain can be introduced. (See, e.g., FIG. 3).

The efficacy and validity of this approach was empirically assessed by introducing variability into immunoglobulin genes within the CDR1 and CDR3 regions as described and by expressing zinc finger nuclease (ZFN) proteins targeting the $V_H$ and $V_L$ sequences in Jurkat T cells. Analysis of the DNA isolated from each cell type employing the Surveyor nuclease assay (such as is available from Transgenomic Inc, USA/Transgenomic, Ltd., Europe), as used to detect ZNF-induced mutations, showed efficient mutation of the IgG1 gene. The Surveyor nuclease assay is a simple and flexible mutation detection technology for the discovery and mapping of both known and unknown mutations. This technology is based on a mismatch-specific DNA endonuclease from celery, Surveyor nuclease, which is a member of the CEL nuclease family of plant DNA endonucleases. Surveyor nuclease cleaves with high specificity at the 3' side of any mismatch site in both DNA strands, including all base substitutions and insertion/deletions up to at least 12 nucleotides. Surveyor nuclease technology involves four steps: (i) PCR to amplify target DNA from both mutant and wild-type reference DNA; (ii) hybridization to form heteroduplexes between mutant and wild-type reference DNA; (iii) treatment of annealed DNA with Surveyor nuclease to cleave heteroduplexes; and (iv) analysis of digested DNA products using the detection/separation platform of choice. The technology is highly sensitive. Sequence analysis of cloned immunoglobulin genes amplified from Jurkat T cells was employed to confirm the presence of ZFN-induced insertions and deletions in the corresponding gene.

In some embodiments, in addition to the ZFN-mediated genetic mutation and diversity described herein, the mutagenesis efficiency within the CDRs can be further increased. This can be achieved by co-expression in cells that express one or more binding molecules, e.g., antibodies, or binding portions thereof, comprising modified CDRs and one or more members of a ligand receptor-cognate ligand pair bindable by the binding molecule(s), other regulatory proteins involved in DNA and recombination events, including but not limited to, the viral-derived Tax regulator protein (Lemoine, F. et al., 2000, AIDS Research and Human Retroviruses, 16(16):1623-1627; Chandhasin, C. et al., 2008, J. Virology, 82(14):6954-6961; Ishikawa, C., et al., 2011, Carcinogenesis, 32(1):110-119; and Baydoun, H. et al., 2012, PLOS One, 7(8):e42226); viral-derived p30 (Baydoun, H. et al., 2011, Blood, 117(22):5897-5906); terminal transferase; or by chemical treatment. In accordance with such embodiments, the ATM-dependent, double stranded break (DSB) response (DSBR) in cells recognizes DNA DSBs and generates chromatin-associated complexes around DSBs that promote DSB repair via C-NHEJ. For this process, the activation of several phosphatidylinositol-3-kinase-like serine/threonine kinases, including DNA-PKcs and ATM, is required. The ATM-dependent DSB response leads to the assembly of macromolecular foci over large (e.g., two megabases or more) chromatin regions flanking the DSB. These foci are thought to serve as scaffolds to stabilize DSB ends and facilitate the recruitment of additional repair and checkpoint signaling factors. For example, DNA-PKcs-deficient cells require ATM for the repair of RS ends, indicating that DNA-PKcs and ATM have overlapping roles in the context of immunoglobulin V(D)J recombination. Therefore, to increase C—NHEJ, the use of ATM kinase inhibitors, e.g., (2-Morpholin-4-yl-6-thianthren-1-yl-pyran-4-one), or DNA-PK inhibitors, e.g., (2-(Morpholin-4-yl)-benzo[h]chromen-4-one, LY293646) can increase the variability of CDR diversification in accordance with the methods of the invention.

As described herein, sequences of zinc finger nucleases are used together with the zinc finger protein targeting sequences inserted into the $V_H$ and/or $V_L$ CDRs in accordance with the described methods of generating diversity, particularly, diversity in target antigen binding activity, in one or more antibody molecules. The ZFNs used in the methods herein are designed to contain at least one, e.g., two, zinc finger protein DNA binding recognition sequence ("targeting region"), which directs the expressed ZFNs to bind to the recognition sequences or targeting regions introduced into the CDRs. Illustratively, but without limiting the invention, FIG. 5 presents representative constructs designed to express zinc finger nucleases in the cells into which one or more antibodies (or one or more diversified antibodies) and target proteins are also co-expressed in accordance with the methods of the invention.

The invention encompasses a method of generating antibody genetic diversity or variability by modifying immunoglobulin complementarity determining regions (CDRs). Accordingly, the method comprises (a) introducing into one or more CDR-encoding nucleic acid sequences one or more zinc finger DNA binding domain recognition sequences to generate one or more non-identical targeting sites within the CDR-encoding nucleic acid sequences for binding one or more zinc finger nucleases (ZFN), thereby producing modified CDR-encoding nucleic acid sequences; (b) introducing into a nucleic acid sequence encoding a zinc finger nuclease (ZFN) the zinc finger DNA binding domain targeting site sequences of (a) operably linked to a nucleic acid sequence encoding a DNA cleavage domain of a type IIS restriction enzyme, wherein DNA cleavage by the ZFN is determined by the targeting site sequences within the modified CDR-encoding nucleic acid sequence of (a); and (c) expressing the nucleic acid sequences of (b) in a cell containing nucleic acid encoding at least an antibody heavy chain variable domain ($V_H$) and/or at least an antibody light chain variable domain ($V_L$) comprising the modified CDR-encoding nucleic acid sequence of (a) under conditions in which the expressed ZFN binds and cleaves the modified CDR-encoding nucleic acid sequence within the targeting site sequence.

In an embodiment of the above method for generating genetically diverse binding molecules, the zinc finger DNA binding domain recognition sequences that are introduced into one or more of CDR1, CDR2 and CDR3 comprise different recognition sequences. In various embodiments, the one or more zinc finger DNA binding domain recognition sequences are introduced into one or more of CDR1, CDR2 and CDR3; the one or more zinc finger DNA binding domain recognition sequences are introduced into each of CDR1, CDR2 and CDR3; the one or more zinc finger DNA binding domain recognition sequences are introduced into each of CDR1 and CDR3. In various embodiments, one zinc finger DNA binding domain recognition sequence is introduced into one or more of CDR1, CDR2 and CDR3; at least two zinc finger DNA binding domain recognition sequences are introduced into one or more of CDR1, CDR2 and CDR3; or two zinc finger DNA binding domain recognition sequences are introduced into one or more of CDR1, CDR2 and CDR3. In various other embodiments, one zinc finger DNA binding domain recognition sequence is introduced into each of CDR1, CDR2 and CDR3; at least two zinc finger DNA binding domain recognition sequences are introduced into each of CDR1, CDR2 and CDR3; or two zinc finger DNA binding domain recognition sequences are introduced into each of CDR1, CDR2 and CDR3. In an embodiment, the introduced zinc finger DNA binding domain recognition sequences are different. In an embodiment, two different zinc finger DNA binding domain recognition sequences are introduced into each of CDR1 and CDR3.

In yet other embodiments of the above-described method, two different zinc finger DNA binding domain recognition sequences are introduced into one or more of CDR1, CDR2 and CDR3 or into each of the three CDRs. In an embodiment, the two different zinc finger DNA binding domain recognition sequences introduced into each of the CDRs comprise SEQ ID NO:6. In an embodiment, the two different zinc finger DNA binding domain recognition sequences introduced into each of CDR1 and CDR3 comprise SEQ ID NO:6. In another embodiment, the two different zinc finger DNA binding domain recognition sequences introduced into each of CDR1 and CDR3 of the $V_H$ and the $V_L$ antibody domains comprise a total of 24 base pairs. In another embodiment, in (b) of the above method, the type II restriction enzyme is Fok I. In an embodiment, in (b) of the method, the nucleic acid sequences encoding the zinc finger nucleases (ZFNs) are introduced into a construct which comprises a first ZFN sequence for cleavage within CDR1 of a $V_H$ domain, a second ZFN sequence for cleavage within CDR1 of a $V_H$ domain, and a first ZFN sequence for cleavage within CDR3 of a $V_H$ domain and a second ZFN sequence for cleavage within CDR3 of a $V_H$ domain. In an embodiment, the method encompasses (i) the first ZFN sequence for cleavage within CDR1 comprises a targeting sequence as set forth in SEQ ID NO:7 and a ZFP recognition sequence as set forth in SEQ ID NO:8, and the second ZFN sequence for cleavage within CDR1 comprises a targeting sequence as set forth in SEQ ID NO:9 and a ZFP recognition sequence as set forth in SEQ ID NO:10; and (ii) the first ZFN sequence for cleavage within CDR3 comprises a targeting sequence as set forth in SEQ ID NO:11 and a ZFP recognition sequence as set forth in SEQ ID NO:12, and the second ZFN sequence for cleavage within CDR3 comprises a targeting sequence as set forth in SEQ ID NO:13 and a ZFP recognition sequence as set forth in SEQ ID NO:14. In an embodiment, in (b) of the method, the nucleic acid sequences encoding the zinc finger nucleases (ZFNs) are introduced into a construct which comprises a first ZFN sequence for cleavage within CDR1 of a $V_L$ domain, a second ZFN sequence for cleavage within CDR1 of a $V_L$ domain; and a first ZFN sequence for cleavage within CDR3 of a $V_L$ domain and a second ZFN sequence for cleavage within CDR3 of a $V_L$ domain. In an embodiment, the method encompasses (i) the first ZFN sequence for cleavage within CDR1 comprises a targeting sequence as set forth in SEQ ID NO:15 and a ZFP recognition sequence as set forth in SEQ ID NO:16, and the second ZFN sequence for cleavage within CDR1 comprises a targeting sequence as set forth in SEQ ID NO:17 and a ZFP recognition sequence as set forth in SEQ ID NO:18; and (ii) the first ZFN sequence for cleavage within CDR3 comprises a targeting sequence as set forth in SEQ ID NO:19 and a ZFP recognition sequence as set forth in SEQ ID NO:20, and the second ZFN sequence for cleavage within CDR3 comprises a targeting sequence as set forth in SEQ ID NO:21 and a ZFP recognition sequence as set forth in SEQ ID NO:22. In embodiments, the construct comprises a lentivirus vector. In various embodiments, the full length antibody is selected from an IgG, IgM, IgA, IgD, or IgE antibody; the full length antibody is an IgG antibody; the IgG antibody is an IgG1, IgG2a, IgG2b, IgG3, or IgG4 antibody; or the antibody is an IgG1 antibody. In an embodiment, in (c) of the method, the cell is a T-cell line or a Jurkat T-cell line. In an embodiment, the method further comprises (d) expressing in the cell a receptor protein which is expressible on the cell surface and which is a potential target bindable by the $V_H$ and/or $V_L$ domain comprising modified CDRs of (c); (e) expressing in the cell a cognate ligand of the receptor protein, the cognate ligand being molecularly tagged with a sequence for retaining the ligand in an intracellular organelle under conditions allowing for the retention of the ligand in the organelle and the interaction of the receptor protein and the cognate ligand in the organelle, wherein the cognate ligand is a potential target bindable by the $V_H$ and/or $V_L$ domain of (c); and (f) detecting the level of the receptor protein expressed on the cell surface; wherein, if the $V_H$ and/or $V_L$ domain binds to either the receptor protein or the cognate ligand and blocks or disrupts their binding interaction in the organelle, the receptor protein transits through the organelle and is expressed and detectable on the cell surface, and wherein the $V_H$ and/or $V_L$ domain which blocks or disrupts the receptor protein and ligand interaction is recoverable from the cell. In various embodiments of the method, the intracellular organelle retention sequence is an ER or Golgi retention sequence; and the ER retention sequence is the KDEL amino acid sequence (SEQ ID NO:1).

In an embodiment, in (a) of the above method, the CDR-encoding nucleic acid sequences are contained within a nucleic acid construct or a cassette. In an embodiment, the CDR-encoding nucleic acid sequences are contained within nucleic acid sequences encoding an antibody heavy chain variable domain ($V_H$) and/or nucleic acid sequences encoding an antibody light chain variable domain ($V_L$). In an embodiment, in (c) of the above method, the modified CDR-encoding nucleic acid sequence is contained within a full length antibody comprising nucleic acid sequences encoding a heavy chain variable domain ($V_H$) and a heavy chain constant region ($C_H$), and comprising nucleic acid sequences encoding a light chain variable domain ($V_L$) and a light chain constant region ($C_L$), wherein the resulting nucleic acid sequences encode full length antibodies comprising $V_H$ and $V_L$ domains comprising modified CDRs. In an embodiment, the above method further comprises amplifying the nucleic acid sequences encoding the $V_H$ and/or $V_L$ domain proteins and cloning the $V_H$ and/or $V_L$ domain proteins from the cell.

In another embodiment, in (b) of the above method, the type II restriction enzyme Fok I. In an embodiment, in (b) of the above method, the nucleic acid sequences encoding the zinc finger nucleases (ZFNs) are introduced into a construct which comprises a first ZFN sequence for cleavage within CDR1 of a $V_H$ domain, a second ZFN sequence for cleavage within CDR1 of a $V_H$ domain, and a first ZFN sequence for cleavage within CDR3 of a $V_H$ domain and a second ZFN sequence for cleavage within CDR3 of a $V_H$ domain. In an embodiment, the above method encompasses (i) the first ZFN sequence for cleavage within CDR1 comprises a targeting sequence as set forth in SEQ ID NO:7 and a ZFP recognition sequence as set forth in SEQ ID NO:8, and the second ZFN sequence for cleavage within CDR1 comprises a targeting sequence as set forth in SEQ ID NO:9 and a ZFP recognition sequence as set forth in SEQ ID NO:10; and (ii) the first ZFN sequence for cleavage within CDR3 comprises a targeting sequence as set forth in SEQ ID NO:11 and a ZFP recognition sequence as set forth in SEQ ID NO:12, and the second ZFN sequence for cleavage within CDR3 comprises a targeting sequence as set forth in SEQ ID NO:13 and a ZFP recognition sequence as set forth in SEQ ID NO:14. In an embodiment, in (b) of the above method, the nucleic acid sequences encoding the zinc finger nucleases (ZFNs) are introduced into a construct which comprises a first ZFN sequence for cleavage within CDR1 of a $V_L$ domain, a second ZFN sequence for cleavage within CDR1 of a $V_L$ domain; and a first ZFN sequence for cleavage within CDR3 of a $V_L$ domain and a second ZFN sequence for cleavage within CDR3 of a $V_L$ domain.

In an embodiment, the above method encompasses (i) the first ZFN sequence for cleavage within CDR1 comprises a targeting sequence as set forth in SEQ ID NO:15 and a ZFP recognition sequence as set forth in SEQ ID NO:16, and the second ZFN sequence for cleavage within CDR1 comprises a targeting sequence as set forth in SEQ ID NO:17 and a ZFP recognition sequence as set forth in SEQ ID NO:18; and (ii) the first ZFN sequence for cleavage within CDR3 comprises a targeting sequence as set forth in SEQ ID NO:19 and a ZFP recognition sequence as set forth in SEQ ID NO:20, and the second ZFN sequence for cleavage within CDR3 comprises a targeting sequence as set forth in SEQ ID NO:21 and a ZFP recognition sequence as set forth in SEQ ID NO:22. In embodiments, the construct comprises a lentivirus vector. In various embodiments of the above method, the full length antibody is selected from an IgG, IgM, IgA, IgD, or IgE antibody; the full length antibody is an IgG antibody; the IgG antibody is an IgG1, IgG2a, IgG2b, IgG3, or IgG4 antibody; or the antibody is an IgG1 antibody. In an embodiment, in (c) of the above method, the cell is a T-cell line or a Jurkat T-cell line.

In an embodiment, the above method further comprises (d) expressing in the cell a receptor protein which is expressible on the cell surface and which is a potential target bindable by the $V_H$ and/or $V_L$ domain comprising modified CDRs of (c); (e) expressing in the cell a cognate ligand of the receptor protein, the cognate ligand being molecularly tagged with a sequence for retaining the ligand in an intracellular organelle under conditions allowing for the retention of the ligand in the organelle and the interaction of the receptor protein and the cognate ligand in the organelle, wherein the cognate ligand is a potential target bindable by $V_H$ and/or $V_L$ domain of (c); and (f) detecting the level of the receptor protein expressed on the cell surface; wherein, if the $V_H$ and/or $V_L$ domain binds to either the receptor protein or the cognate ligand and blocks or disrupts their binding interaction in the organelle, the receptor protein exits the organelle and is expressed and detectable on the cell surface, and wherein the $V_H$ and/or $V_L$ domain which blocks or disrupts the receptor protein and ligand interaction is recoverable from the cell. In various embodiments of the method, the intracellular organelle retention sequence is an endoplasmic reticulum (ER) or Golgi retention sequence; and the ER retention sequence is KDEL (SEQ ID NO:1).

In another embodiment, the invention provides a method of generating a genetically diverse antibody, or a binding fragment or portion thereof, comprising modified complementarity determining regions (CDRs), wherein the method comprises: (a) preparing modified CDRs by introducing into one or more individual CDR-encoding nucleic acid sequences within the CDR locus of antibody $V_H$ and $V_L$ domains one or more zinc finger DNA binding domain recognition sequences, which are recognized by zinc finger nuclease proteins (ZFN), thereby producing one or more non-identical target sites in the $V_H$ and $V_L$ CDR-encoding nucleic acid sequences for specific binding of ZFNs; (b) preparing isolated nucleic acid sequences encoding zinc finger nucleases (ZFNs) having specificity for and targeting the CDR-containing zinc finger DNA binding domain recognition sequences of (a) and linked to a cleavage domain derived from a TypeII restriction endonuclease, wherein cleavage by the ZFNs is determined by the DNA binding protein recognition sequences within the modified CDRs of (a); (c) introducing the modified CDR-encoding nucleic acid sequence regions of (a) into nucleic acid sequences encoding the $V_H$ and/or $V_L$ domains, thereby producing $V_H$ and/or $V_L$ domains comprising one or more modified CDRs; (d) optionally, introducing the $V_H$ and/or $V_L$ of (c) into isolated nucleic acid sequences encoding an antibody protein comprising heavy (H) and light (L) chains, wherein the resulting nucleic acid sequences encode a full-length antibody protein comprising modified CDR regions comprising different ZFP recognition sites within its $V_H$ and $V_L$ domains; and (e) expressing the nucleic acid sequences of (b) and (c) in a suitable host cell wherein the expressed ZFNs target the modified CDRs within the $V_H$ and $V_L$ sequences of the antibody protein under conditions for producing mutations and genetic diversity in the CDR regions of the expressed $V_H$ and/or $V_L$ domains, or expressed antibody, thereby generating genetically diverse antibodies, or binding portions thereof, that may possess improved or optimal target antigen binding properties.

In an embodiment of the above method, the method further comprises isolating the nucleic acid sequence encoding the antibody produced. In another embodiment, the method further comprises amplifying and subsequently cloning the nucleic acid sequences encoding the genetically diverse antibody protein from the host cell in which they are expressed. In an embodiment, one or more zinc finger DNA binding domain recognition sequences are introduced into one or more of CDR1, CDR2 and CDR3, which are isolated from the $V_H$ and/or the $V_L$ antibody domains, for example, within a vector or cassette, and which are subsequently reintroduced into the $V_H$ and/or $V_L$ domains or into the $V_H$ and $V_L$ domains of full-length antibodies by conventional molecular biology techniques. In another embodiment, in (a) of the method, the one or more zinc finger DNA binding domain recognition sequences is introduced into each of CDR1, CDR2 and CDR3 of the $V_H$ and the $V_L$ antibody domains. In another embodiment, in (a) of the method, the one or more zinc finger DNA binding domain recognition sequences is introduced into each of CDR1 and CDR3 of the $V_H$ and the $V_L$ antibody domains. In another embodiment, in (a) of the method, two different zinc finger DNA binding domain recognition sequences are introduced into each of CDR1 and CDR3 of the $V_H$ and the $V_L$ antibody domains. In an embodiment of the method, the two different zinc finger DNA binding domain recognition sequences introduced into each of CDR1 and CDR3 of the $V_H$ and the $V_L$ antibody domains comprise SEQ ID NO:6. In an embodiment of the method, the two different zinc finger DNA binding domain recognition sequences introduced into each of CDR1 and CDR3 of the $V_H$ and the $V_L$ antibody domains comprise a total of 24 base pairs. In another embodiment, in (b) of the method, the ZFNs comprise zinc finger DNA binding domain recognition sequences coupled to a cleavage domain of the type II restriction enzyme Fok I.

As shown by the present invention, the co-expression of immunoglobulin genes, or binding portions thereof, engineered to contain zinc-finger binding domain hotspots, i.e., the introduced targeting sequences for zinc finger protein binding and activity and recognition by ZFNs, together with ZFN-encoding genes engineered to bind the DNA targeting sequences, and a target protein or antigen in a T-cell line results in a novel cellular system that conveniently couples binding molecule/antibody diversity and selection simultaneously. In accordance with the methods of the invention, an antibody, or a binding portion thereof, from a library, a diversified library, or a population of diversified antibodies, having binding specificity for a target antigen can be selected, identified and characterized by constructing cells or cell lines to contain and express the appropriate target antigen, e.g., a receptor protein or its cognate ligand, and retention signals to allow binding of a specific, expressed antibody, or a binding portion thereof, and retention of the appropriate interacting molecules within the environment of the cell.

The diversity in antibodies that can be generated by the CDR modification methods of the invention is on the order of $10^6$ to $10^{18}$, or $10^6$ to $10^{14}$, or $10^6$ to $10^{12}$ different antibody binding sites. As will be appreciated by the skilled practitioner, the variability in antibodies and their binding specificities attained in accordance with the methods of the invention, for example, in the combination of ZFN-targeted CDR1 and CDR3, will depend upon the efficiency of nuclease activity in each CDR, or in both CDRs together.

The following examples are not meant to limit the invention, but are presented to demonstrate and illustrate the invention in its various embodiments and aspects.

EXAMPLES

Example 1

Materials and Methods

Plasmids and Bacterial Cells

The rabbit $V_L$ Single Domain Antibody (SDA) library of 309 antibodies against hTNF-α and the rabbit $V_L$ SDA 18 ($V_L$18) cloned into the pT7 vector (e.g., as described in PCT/PT2012/000035, F. Aires Da Silva et al., "Anti-tumor necrosis factor-alpha agents and uses thereof" filed Sep. 19, 2012, TechnoPhage, Lisbon, Portugal, and U.S. Provisional Application No. 61/538,548, filed Sep. 23, 2011, the contents of which are hereby incorporated by reference in their entirety). The anti-hTNF-α $V_L$ dimer library was constructed using the restriction/ligation strategy as previously described (Oliveira S S, Aires da Silva F, Lourenco S, Freitas-Vieira A, Santos A C C, et al. (2012), Biotechnology and Applied Biochemistry 59: 193-204). The rabbit $V_L$ SDA F63 cloned in the pComb3X vector was selected by phage display against gp41 and deimmunized (e.g., as described in PCT/PT2012/000035, F. Aires Da Silva et al., "Anti-tumor necrosis factor-alpha agents and uses thereof" filed Sep. 19, 2012, TechnoPhage, Lisbon, Portugal, and U.S. Provisional Application No. 61/538,548, filed Sep. 23, 2011, the contents of which are hereby incorporated by reference in their entirety; and Santos, A. S., Oliveira, S. S., and Gonsalves, J., unpublished results). The plasmids pHEF-VSVG (AIDS Research and Reference Reagent Program, Division of AIDS, NIAID, NIH, from Dr. Lung-Ji Chang), pGagPol (Amendola M, Venneri M A, Biffi A, Vigna E, Naldini L (2005), Nat Biotechnol 23: 108-116), pRev (Amendola M, et al. (2005), Nat Biotechnol 23: 108-116), and pFugW (Lois C, Hong E J, Pease S, Brown E J, Baltimore D (2002), Science (New York, N.Y.)) 295: 868-872 were used to produce lentiviral particles.

Cell Lines and Culture Conditions

HEK293T cells (American Type Culture Collection (ATCC), Manassas, Va., USA) were cultured in DMEM supplemented with 10% FBS (DMEM-10), 2 mM L-glutamine, and 1% penicillin/streptomycin (Thermo Scientific). Jurkat cells (ATCC) and cell lines, e.g., JLTRG-R5 (Ochsenbauer-Jambor C. et al., 2006, BioTechniques, 40(1):91-100), were grown in Roswell Park Memorial Institute medium (RPMI)-1640, supplemented with 10% FBS (RPMI-10), 2 mM L-glutamine, and 1% penicillin/streptomycin. All cell cultures were maintained at 37° C. in 5% $CO_2$. Cell culture media and reagents, unless otherwise indicated, were purchased from Lonza (Basel, Switzerland).

Plasmid/Vector Constructs

Antibody Vectors

In general, all of the expression plasmids were constructed by polymerase chain reaction (PCR) using a polymerase with proofreading activity (Phusion High-Fidelity DNA polymerase, Finnzymes, Thermo Fisher Scientific, Vantaa, Finland).

Figures 6A, 6B, 6C, 6D, 6E:
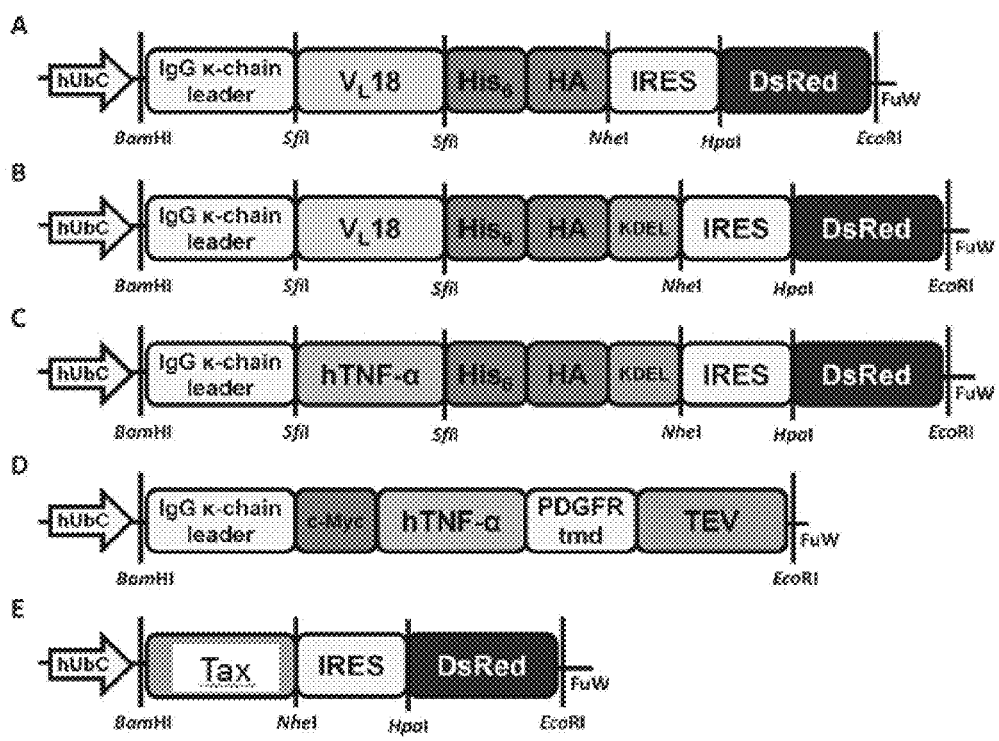

To express the antibodies with and without a retention signal for endoplasmic reticulum (ER), e.g., KDEL (SEQ ID NO:1), two base vectors were constructed: $pV_L18$-IRES-DsRed and $pV_L18$ KDEL-IRES-DsRed ("KDEL" disclosed as SEQ ID NO:1) (FIGS. 6A and 6B, respectively). For $pV_L18$-IRES-DsRed, two fragments were amplified by PCR. The first fragment was generated by amplification of the SDA $V_L18$ from the pT7 vector using the oligonucleotide primers "Leader-Ab-F1" and "Ab-HA-IRES-R1" as presented in Table 1. The forward primer "Leader-Ab-F1" added a murine Ig-κ-chain leader sequence, i.e., $(NH_2)$-METDTLLLWVLLLWVPGSTGD (SEQ ID NO:23)-(COOH), which directs the protein to the secretory pathway (Coloma, M J et al., 1992, J. Immunol. Meths., 152:89-104), while the reverse primer "Ab-HA-IRES-R1" added a polyhistidine ($His_6$ (SEQ ID NO:46)) and a hemagglutinin (HA) tag for detection of the expressed protein via Western blot. The second fragment, IRES-DsRed, was amplified from the pIRES2-DsRed 2 vector (Clontech, Takara Bio Company, CA, USA) using the oligonucleotide primers "HA-IRES-Red-F2" and "IRES-Red-R2" as presented in Table 1. After purification, a PCR overlap of these two fragments was performed using conventional techniques and the oligonucleotide primers "Leader-Ab-F1" and "IRES-Red-R2" as presented in Table 1. The resulting fragment was gel-purified, digested with restriction endonucleases BamHI and EcoRI and cloned into the FugW vector under the control of the human ubiquitin C promoter.

To construct the base vector $pV_L18$ KDEL-IRES-DsRed ("KDEL" disclosed as SEQ ID NO:1), the SDA $V_L18$ was amplified with the oligonucleotide primers "Leader-Ab-F1" and "Ab-HA-KDEL-R1" ("KDEL" disclosed as SEQ ID NO:1) as presented in Table 1. The forward primer was the same as described above, and the reverse primer introduced the ER retention signal, 5' aaggatgagctc 3', (SEQ ID NO:24) (NH2)-KDEL-(COOH) (SEQ ID NO:1), in addition to adding the $His_6$ (SEQ ID NO:46) and HA tags as described. After gel-purification, the PCR fragment was digested with the restriction endonucleases BamHI and NheI and was cloned into the previously constructed vector $pV_L18$-IRES-DsRed, which was also digested by these enzymes. To facilitate the antibody cloning, the SDA $V_L18$ gene was flanked by two restriction sites for the SfiI endonuclease in both vectors (FIGS. 6A and 6B). The base vectors constructed for use in the examples illustrating the invention are schematically represented in FIGS. 6A-6E.

TABLE 1

Oligonucleotides

| Name | Sense | 5'-3' Sequence |
|---|---|---|
| Leader-Ab-F1 | Forward | aaaggatccatggagacagacacactcctgctatgggtactgctgctctgggttccaggt tccactggtgacacggcccaggcggccgagct (BamHI) (SEQ ID NO: 25) |
| Ab-HA-IRES-R1 | Reverse | ttagggggggggagggagaggggcgctagcctaagaagcgtagtccggaacgtcg- tacgg (SEQ ID NO: 26) |
| HA-IRES-Red-F2 | Forward | gactacgcttcttaggctagcgcccctctccctccccccccctaacgttactggccgaa (SEQ ID NO: 27) |
| IRES-Red-R2 | Reverse | tttgaattcctactggaacaggtggtggcg (EcoRI) (SEQ ID NO: 28) |
| Ab-HA-KDEL-R1 ("KDEL" disclosed as SEQ ID NO: 1) | Reverse | ttagggggggggagggagaggggc gctagcctagagctcatccttctcgctagaagcgta gtccggaacgtcgta (NheI) (SEQ ID NO: 29) |
| pComb-1F | Forward | gttggccgattcattaatgcag (SEQ ID NO: 30) |
| pComb-1R | Reverse | aatgaaaccatcgatagcagcac (SEQ ID NO: 31) |
| pComb-3F | Forward | agcgcaacgcaattaatgtgag (SEQ ID NO: 32) |
| pComb-3R | Reverse | ggtcatagcccccttattagcg (SEQ ID NO: 33) |
| CDR1-Lib | Forward | gtgaccattaaatgcagcggcggcggcagcSHRSHRSHRSHRSHRSHRSH RSHRSHRSHRSHRSHRagcggcggcggcagctggtatcagcagaaaccg (SEQ ID NO: 34) |
| CDR1-R | Reverse | gctgccgccgccgctgcatttaatggtcacggtgcc (SEQ ID NO: 35) |
| CDR3-Lib | Forward | acctattattgcagcggcggcggcagcSHRSHRSHRSHRSHRSHRSHRSH RSHRSHRSHRagcggcggcggcagcggcggcggcaccgaactggaa (SEQ ID NO: 36) |
| CDR3-R | Reverse | gctgccgccgccgctgcaataataggtcgccgcatccgc (SEQ ID NO: 37) |
| Leader-TNF-F | Forward | gacgatatcatggagacagacacactc (EcoRV) (SEQ ID NO: 38) |
| TNF-TEV-R | Reverse | tttgaattcctactggctgtagactagctc (EcoRI) (SEQ ID NO: 39) |
| TNF-KDEL-F ("KDEL" disclosed as SEQ ID NO: 1) | Forward | gacacggcccaggcggcccctgtagcccatgttgtagcaaac (SfiI) (SEQ ID NO: 40) |

TABLE 1-continued

Oligonucleotides

| Name | Sense | 5'-3' Sequence |
|---|---|---|
| TNF-KDEL-R ("KDEL" disclosed as SEQ ID NO: 1) | Reverse | atggtgctggccggcctgcccagggcaatgatccc (SfiI) (SEQ ID NO: 41) |
| Tax-F | Forward | ctaggatccatggacagcctcttgatgaac (BamHI) (SEQ ID NO: 42) |
| Tax-R | Reverse | tttgctagctcaaagtcccaaagtacg (NheI) (SEQ ID NO: 43) |
| Seq-Leader-F | Forward | atggagacagacacactcctgctatgg (SEQ ID NO: 44) |
| Seq-HA-R | Reverse | gtagtccggaacgtcgtacgggta (SEQ ID NO: 45) |

The underlined nucleotides indicate the recognition sites of restriction endonucleases used. The double underlines indicate a CDR region with wobble bases, as provided by the UIB code from ThermoScientific or from the single letter codes for nucleotides as provided by NCBI through its website at www.ncbi.nlm.nih.gov/staff/tao/tools/tool lettercode.html.

Vectors for Cell Line Construction

For the generation of a cell line expressing hTNF-α protein in fusion with the retention signal KDEL (SEQ ID NO:1), the vector pTNFKDEL-IRES-DsRed ("KDEL" disclosed as SEQ ID NO:1) was constructed. (FIG. 6C). The gene encoding hTNF-α (GenBank accession number P01375) was amplified by PCR using the oligonucleotide primers "TNF-KDEL-F ("KDEL" disclosed as SEQ ID NO:1)" and "TNF-KDEL-R ("KDEL" disclosed as SEQ ID NO:1)" (Table 1). After gel-purification, the nucleic acid fragment was digested with restriction endonuclease SfiI and cloned into the previously constructed plasmid pV$_L$18KDEL-IRES-DsRed ("KDEL" disclosed as SEQ ID NO:1), replacing the SDA V$_L$18 nucleic acid sequence.

To construct the cell line expressing hTNF-α, the vector pTNF-TEV (FIG. 6D) was engineered. The hTNF-α gene was amplified by PCR with oligonucleotides "Leader-TNF-F" and "TNF-TEV-R" (Table 1). The amplified nucleic acid fragment was digested with restriction endonucleases EcoRV and EcoRI and cloned into the FugW vector, which was digested with BamHI and EcoRI. The synthesized gene was designed to have a murine Ig-κ-chain leader sequence and a c-Myc tag upstream of the hTNF-α gene for western blot detection.

For the development of the cell line expressing a Tax polypeptide, the vector pTax-IRES-DsRed (FIG. 6E) was constructed. Accordingly, the Tax gene (Genbank accession number P03409) was amplified using the oligonucleotide primers "Tax-F" and "Tax-R" (Table 1). After purification, the amplified nucleic acid fragment was digested with BamHI and NheI endonucleases and cloned into the previously constructed vector pV$_L$18-IRES-DsRed plasmid. This cloning removed the murine IgG leader sequence and the His$_6$ (SEQ ID NO:46) and HA tags.

Unless otherwise indicated herein, all enzymes used in the Examples were from Fermentas (Thermo Fisher Scientific, Waltham, Mass., USA). Each of the constructed vectors was transformed into the E. coli strain JM109 (Life Technologies, Regensburg, Germany) by electroporation (200Ω, 25 μFD, 1.8 kV, Bio-Rad Pulse Controller; Bio-Rad, CA, USA) to allow vector propagation and DNA extraction and isolation of desired nucleic acids.

Expression of Plasmid Constructs in HEK 293T Cells

To evaluate the expression of the plasmid constructs, HEK293T cells were transfected with 5 μg of plasmid DNA for each plasmid by the conventional calcium phosphate transfection method. After 48 hours, the cells were washed with phosphate buffer solution (PBS) and lysed with HBS buffer [50 mM HEPES; 150 mMNaCl; 2 mM EDTA; 10% (v/v) glycerol; 0.5% (w/v) deoxycholic acid; 1% (v/v) triton X-100] supplemented with a cocktail of protease inhibitors (Roche Diagnostics GmbH). This mixture was incubated on ice for 30 minutes and then was centrifuged at 12.000×g for 30 minutes at 4° C. The recovered soluble fraction was used for Western blot analysis. The protein concentration was quantified using the Bradford colorimetric assay (BioRad, CA, USA).

SDS-PAGE and Immunoblot Analysis

For SDS-PAGE and immunoblot analysis, equal amounts of protein were boiled in Laemmli buffer (Laemmli, 1970) and loaded onto 10% SDS-PAGE gels. Proteins were separated by electrophoresis (Mini-Protean™ tetra electrophoresis system; Bio-Rad) and blotted onto nitrocellulose membrane Hybond-C Extra (Amersham Bioscience UK, Buckinghamshire, UK). The nitrocellulose membranes were soaked in blocking solution (5% (w/v) nonfat milk in Tris-buffered saline plus 0.1% of Tween20 (TBS-T) buffer) for 1 hour at room temperature. Following blocking, the nitrocellulose membranes blotted with antibody protein expressed from the antibody constructs and with hTNF-α protein expressed from the TNF-α construct were incubated with HRP-conjugated anti-HA monoclonal antibody (clone 3F10; Roche Diagnostics GmbH) or with HRP conjugated anti-c-myc monoclonal antibody (clone 9E10; Roche Diagnostics GmdH), respectively, diluted 1:5.000 in 3% (w/v) nonfat dry milk in TBS-T at room temperature for 1 hour.

Lentiviral Particle Production and Cell Line Construction JLTRG-R5TNFKDEL ("KDEL" Disclosed as SEQ ID NO:1) Cell Line For the generation of cell lines stably expressing TNF-KDEL-IRES-DsRed ("KDEL" disclosed as SEQ ID NO:1), HEK293T cells (6×10$^6$ cells) were co-transfected by the conventional calcium phosphate method with pTNFKDEL-IRES-DsRed ("KDEL" disclosed as SEQ ID NO:1), pVSVG, pRev, and pGagPol in the proportions of 1.5:0.2:1:2 to produce lentiviral particles encoding TNFKDEL-IRES-DsRed ("KDEL" disclosed as SEQ ID NO:1). The pVSVG, pRev, and pGagPol plasmids, i.e., lentiviral packaging plasmids as known in the art, are used to provide the necessary proteins for lentivirus production within transduced cells. More specifically, VSV is used as an envelope vector and allows virus endocytosis. Rev, an HIV-1 protein, is a nuclear transactivator that is essential for the expression of viral structural proteins from unspliced (gag/pol) and incompletely spliced (env) HIV-1 mRNAs in late phases of infection. GagPol are HIV-1 genes; Gag encodes the HIV-1 Gag polyprotein, which is processed during virus maturation to matrix protein (MA, p17), capsid protein (CA, p24), spacer peptide 1 (SP1, p2), nucleocapsid protein (NC, p7), spacer peptide 2 (SP2, p1) and p6. Pol encodes the viral enzymes reverse transcriptase, integrase and HIV protease. The lentivirus particles carry the plasmid construct. After transduction of cells, the DNA is integrated into the genome of the host cell and is expressed along with other host cell genes.

After 48 hours, lentiviral particles were collected and used to transduce JLTRG-R5 cells. JLTRG-R5 cells express the hTNF-α receptor and also contain an HIV LTR promoter that controls the expression of green fluorescent protein (GFP), which is only activated when the cells are infected by an HIV virus, or when cells are transduced or transfected by plasmids encoding HIV activating proteins, such as the Tat protein, the HIV-1 transcription activator. The cells were resuspended in a lentivirus preparation with polybrene (8 µg/mL) and subjected to spinoculation at 930×g for 90 minutes at 32° C. The lentivirus was used in an amount sufficient to produce an approximately 60%-80% transduction efficiency as observed by flow cytometry. The spinoculation was performed in a 24-well plate, with about $2.5 \times 10^5$ cells in 250 µL of RPMI+FBS plus 750 µL of lentivirus particles in each well of the plate. After 6 hours, the cells were washed and the medium was replaced with RPMI containing 10% FBS. At 72 hours post-transduction, the cells were collected, washed twice with PBS supplemented with 0.5% (w/v) of Bovine Serum Albumin (BSA) fraction V, sorted for DsRed positive cells in a BD FACS ARIA III cell sorter (Beckton Dickinson Bioscience, CA, USA) and seeded in 24-well plates, typically at a density of $5 \times 10^6$ cells per 500 µL. Untransduced cells were used as negative control. In this way, when DsRed-positive cells are sorted, the selected cells express both hTNF-α-KDEL ("KDEL" disclosed as SEQ ID NO:1) and its receptor. After 6 days, the sorted cells were stained for the expression of hTNF-α receptor I with 125 ng of an allophycocyanin (APC)-conjugated mouse monoclonal antibody directed against anti-hTNF-α R1 to validate that these cells were able to retain this receptor in the ER due to the expression of TNFKDEL protein ligand ("KDEL" disclosed as SEQ ID NO:1) as described. The FACS ARIA III apparatus was used to acquire at least 10,000-gated events from each sample and the data were analyzed using FlowJo software (Tree Star, Oreg., USA).

JLTRG-R5-TNF-TEV-Expressing Cell Line

To produce TNF-TEV-encoding lentiviral particles for the construction of the JLTRG-R5-TNF-TEV cell line expressing hTNF-α ligand protein, HEK293T cells were co-transfected by the conventional calcium phosphate method with pTNF-TEV, pVSVG, pRev, and pGagPol in the proportions of 1.5:0.2:1:2. After 48 hours, lentiviral particles were harvested and were used to transduce JLTRG-R5 cells. The cells were resuspended in a lentiviral preparation with polybrene (8 µg/mL) and subjected to spinoculation at 930×g for 90 minutes at 32° C. After 6 hours, cells were washed and medium was replaced. At 72 hours post-transduction, the cells were collected, washed twice with PBS-BSA 0.5%, and stained for hTNF-α surface expression with 2.5 µg of etanercept (Enbrel®) for 30 minutes at 4° C. The cells were washed two times with PBS-BSA, and etanercept (Enbrel®) binding to hTNF-α was detected by staining the cells with a secondary antibody [Alexafluor® 647-conjugated AffiniPure anti-human IgG (Alexafluor®)] (1:500) for 30 minutes at 4° C. After staining, the cells were resuspended in PBS-BSA and sorted for etanercept-Alexafluor® 647-positive cells in a BD FACS ARIA III (BD Bioscience, CA, USA). Labeled untransfected cells and cells labeled only with secondary antibody were used as negative controls. All data were analyzed using FlowJo software.

JLTRG-R5-TNF-TEV and Tax-Expressing Cell Line

To generate a JLTRG-R5 cell line expressing the hTNF-α and Tax polypeptides, a conventional calcium phosphate transfection method was used. Tax-IRES-DsRed-encoding lentiviral particles were produced by co-transfection of HEK293T cells with pTax-IRES-DsRed, pVSVG, pRev, and pGagPol as described above (in the proportions of 1.5:0.2:1:2). After 48 hours, lentiviral particles were collected and used to transduce the JLTRG-R5-TNF-TEV cells expressing hTNF-α protein. Cells were resuspended in a lentiviral preparation with polybrene (8 µg/mL) and subjected to spinoculation at 930×g for 90 minutes at 32° C. After 6 hours, the cells were washed and the medium was replaced. At 72 hours post-transduction, the cells were collected, washed twice with PBS-BSA 0.5%, and stained for hTNF-α surface expression with 2.5 µg of etanercept (Enbrel®) for 30 minutes at 4° C. The cells were washed two times with PBS-BSA, and stained for 30 minutes at 4° C. with secondary antibody, Alexafluor® 647 (1:500). After staining, the cells were resuspended in PBS-BSA and sorted for DsRed and etanercept-Alexafluor® 647-positive cells in a BD FACS ARIA III. Labeled, untransfected cells and cells labeled only with secondary antibody were used as negative controls. The data from BD FACS ARIA III were analyzed using FlowJo software.

Example 2

Cell Based Assay to Select and Evolve Antibodies that Retain Target Molecules/Ligands in the ER HEK293T cells were used for the expression and production of antibody-encoding lentiviral particles, in particular, antibodies coupled to the ER retention signal KDEL (SEQ ID NO:1) (antibody-KDEL ("KDEL" disclosed as SEQ ID NO:1)). To this end, HEK293T cells were co-transfected with $pV_L18$-IRES-DsRed and with pVSVG, pREV, and pGagPol in the proportions of 1.5:0.2:1:2, respectively. After 48 hours, lentiviral particles were harvested and used to transduce cell lines JLTRG-R5-TNF-TEV or JLTRG-R5-TNF-TEV-Tax. Cells were resuspended in a lentiviral preparation with polybrene (8 µg/mL) and subjected to spinoculation at 930×g for 90 minutes at 32° C. As a control for the percentage of transduced cells, equal amounts of JLTRG-R5 cells were transduced, also by spinoculation, with an equal amount of lentiviral particles used to transduce the aforementioned cell lines. After 6 hours, the cells were washed and new medium (RPMI supplemented to contain 10% FBS) was added. At 72 hours post-transduction, the cells were collected, washed twice with PBS-BSA 0.5%, stained for hTNF-α with 2.5 µg of etanercept, and 1:500 of secondary antibody Alexafluor® 647. Cells that stained positive for DsRed expression and negative for hTNF-α surface expression were sorted in a BD FACS ARIA III, seeded, and were allowed to grow in culture for one to two weeks. The selected cells expressed antibodies that efficiently recognized hTNF-α and retained this target protein in the ER. To support the previously determined phenotype, the cells were recovered, washed, and prepared for another round of cell sorting in the BD FACS ARIA III. Sorted cells were seeded, and five days later genomic DNA from all the sorted cells was extracted with QuickExtract™ DNA Extraction Solution (Epicenter®, an Illumina® company, WI, USA). Antibody encoding genes were recovered from the cells.

Example 3

Cell Based Assay to Select Antibodies that Neutralize/Disrupt a Ligand Pair Binding Interaction HEK293T cells were used to produce the antibody-encoding lentiviral particles. Therefore, the cells were co-transfected with $pV_L18$-IRES-DsRed, and pVSVG, pREV, pGagPol. After 48 hours, lentiviral particles were collected and used to transduce the cell line JLTRG-R5-TNFKDEL ("KDEL" disclosed as SEQ ID NO:1). The lentiviral particles were typically used in an amount that yielded approximately 60%-80% transduction efficiency; in general, $2.5 \times 10^5$ cells in 250 μL of RPMI+FBS plus 750 μL of lentiviral particles in each well of a 24-well plate. The JLTRG-R5 cells were resuspended in the lentiviral preparation with polybrene (8 μg/mL) and subjected to spinoculation at 930×g for 90 minutes at 32° C. As a control for the percentage of transduced cells, equal amounts of JLTRG-R5 cells were transduced, also by spinoculation, with an amount of lentiviral particles equal to that used to transduce the JLTRG-R5-TNFKDEL ("KDEL" disclosed as SEQ ID NO:1) cells. After 6 hours, the transduced cells were washed and new medium was added. 72 hour post-transduction, the cells were harvested, washed twice with PBS-BSA 0.5%, stained for hTNF-α Receptor I with 125 ng of APC-conjugated mouse monoclonal antibody anti-hTNF-α RI, and sorted for DsRed and APC positive cells in BD FACS ARIA III. In this way, sorted cells that were positive were demonstrated to express antibodies capable of neutralizing or disrupting the interaction between the hTNF-α and its receptor, thereby allowing the receptor to be expressed on the cell surface and detected by the anti-hTNF-α RI antibody. The sorted cells were seeded and allowed to grow for one to two weeks. To corroborate the detected phenotype, the cells were washed again and prepared for another round of cell sorting in BD FACS ARIA III. The sorted cells that were positive for DsRed and hTNF-α RI expression were seeded. Normally, the cells were cultured in 24-well plates at a density of $5 \times 10^6$ cells per 500 μL. After five days, genomic DNA was extracted with QuickExtract™ DNA Extraction Solution (Epicenter®, an Illumina® company, WI, USA) so that the antibodies responsible for this phenotype in flow cytometry could be characterized. (See, e.g., FIGS. 7A and 7B).

Example 4

Cloning, Expression and Binding Analysis of Single Domain Antibodies (SDA) by ELISA The extracted genomic DNA from the different cells was amplified by PCR using the oligonucleotide primers "Seq-Leader-F" and "Seq-HA-R" (Table 1). The amplified fragments (antibodies) were digested with restriction endonuclease SfiI, cloned into the pT7 vector (kindly provided by TechnoPhage), and transformed by electroporation (200Ω, 25 μFD, 1.8 kV, Bio-Rad Pulse Controller) into E. coli strain BL21 (DE)$_3$. Several dilutions of transformed bacteria were plated in Luria broth (LB) agar plates supplemented with 100 μg/mL of ampicillin. To screen for the sorted antibodies, bacterial colonies from each cloning were isolated, diluted in 200 μL of autoinduction medium (e.g., Overnight Express Autoinduction System, Novagen, San Diego, Calif. for an automated system such as a robot) in a 96-well plate, and allowed to grow for 16 hours at 37° C. and 150 rpm. Each sorted cell population, e.g., the DsRed+Alexafluor® 647-negative for the antibody-KDEL assay ("KDEL" disclosed as SEQ ID NO:1), or DsRed+APC-positive for the hTNF-α-KDEL assay ("KDEL" disclosed as SEQ ID NO:1), was used to extract genomic DNA. From these DNA samples, the antibody genes were amplified and were cloned into the pT7 vector as described herein. Thereafter, BL21(DE)3 bacteria were transformed with the vector. The isolated colonies resulting from the bacterial transformation were picked. For each different antibody and antibody library used, a cloning was performed. Subsequently, bacteria pellets from cell cultures centrifuged for 15 minutes at 900×g were lysed with the addition of phosphate buffer solution (PBS) and BugBuster Master Mix (Novagen, Merck KGaA, Darmstadt, Germany) (in a proportion of 1:2) supplemented with a cocktail of protease inhibitors (Roche Diagnostics GmbH, Mannheim, Germany). This mixture was incubated for 4 hours at 4° C. in a stirring plate and the soluble periplasmic extract was collected after centrifugation at 900×g for 15 minutes. The recovered soluble fraction was used for ELISA.

In the expression assay, a 96-well ELISA plate was coated with 55 μL of bacteria clone soluble fraction for 1 hour at 37° C. Plate wells were washed with PBS and blocked for 1 hour at 37° C. with 3% (w/v) BSA. After washing with PBS, HRP-conjugated anti-HA monoclonal antibody (clone 3F10, Roche Diagnostics GmbH) diluted 1:1000 in 1% (w/v) BSA was added to each well, and the plate was incubated at 37° C. for 1 hour. Following the incubation time, the wells of the plate were washed with PBS, and the ELISA detection was performed by the addition of HRP substrate ABTS Chromophore (Calbiochem; Merck KGaA) combined with 0.2% (v/v) of hydrogen peroxide (Calbiochem; Merck KGaA). The absorbance was measured at 405 nm (using 492 nm as reference) on Tecan Infinite M200 (Tecan, Mannedorf, Switzerland) after 30 minutes at 37° C.

To assess the binding of antibodies to hTNF-α, a 96-well ELISA plate was coated with 200 ng of hTNF-α (Prospec, N.J. USA) and incubated overnight at 4° C. After washing with PBS, the wells of the plate were blocked for 1 hour at 37° C. with 3% (w/v) BSA. 55 μL of soluble fraction of each bacterial clone was subsequently added to the wells, and the plate was incubated for another hour at 37° C. Following this incubation time, the plate wells were washed with PBS, and HRP-conjugated anti-HA monoclonal antibody diluted 1:1000 in 1% (w/v) BSA was added to each well. The plate was incubated for 1 hour at 37° C., and the plate wells were then washed with PBS. The ELISA detection was performed by the addition of HRP substrate ABTS Chromophore combined with 0.2% (v/v) of hydrogen peroxide. The absorbance was measured at 405 nm (using 492 nm as reference) on a Tecan Infinite M200 (Tecan Systems Ltd., US and Germany) after 30 minutes at 37° C.

Example 5

Production of Plasmids Containing Zinc Finger Nucleases (ZFN) which Specifically Target CDRs Containing Zinc Finger DNA Binding Protein Recognition Sequences In plasmid vectors comprising the backbone of the FugW lentiviral vector, zinc-finger-nucleases were cloned by overlap PCR with a 2 A (Angstrom) sequence separating each gene. The zinc finger nuclease, termed ZFN1VH in FIG. 5, was designed to target CDR1 in the variable region of the heavy chain (V$_H$). ZFN1VH comprises a targeting region comprising the nucleic acid sequence gtcgaaaagcca (SEQ ID NO:7) and a zinc finger amino acid sequence LEPGEKPYKCPECGKSFSTSHSLTEHQRTHTGEKPYKCPECGKSFSRKDNLKNHQRTHT GEKPYKCPECGKSFSQSSNLVRHQRTHTGEKPYKCPECGKSFSDPGALVRHQRTHTGKKTS SEQ ID NO:8). The zinc finger nuclease, termed ZFN2VH, targets CDR1 in the variable region of the heavy chain. ZFN2VH comprises a targeting region comprising the nucleic acid sequence caaaaatcgagct (SEQ ID NO:9) and the zinc finger amino acid recognition sequence LEPGEKPYKCPECGKSFSTSGELVRHQRTHTGEKPYKCPECGKSFSQSGHLTEHQRTHT GEKPYKCPECGKSFSTTGNLTVHQRTHTGEKPYKCPECGKSFSQSGNLTEHQRTHTGKK TS (SEQ ID NO:10). The zinc finger nuclease, termed ZFN3VH, targets CDR3 in the variable region of the heavy chain. ZFN3VH comprises a targeting region comprising the nucleic acid sequence actcagcgaacg (SEQ ID NO:11) and the zinc finger amino acid recognition sequence LEPGEKPYKCPECGKSFSRTDTLRDHQRTHTGEKPYKCPECGKSFSQSGHLTEHQRTHTGEKPYKCPECGKSFSRADNLTEHQRTHTGEKPYKCPECGKSFSTHLDLIRHQRTHTGKK TS (SEQ ID NO:12). The zinc finger nuclease, termed ZFN4VH, targets CDR3 in the variable region of the heavy chain. ZFN4VH comprises a targeting region comprising the nucleic acid sequence caatgtcggtaca (SEQ ID NO:13) and the zinc finger amino acid recognition sequence LEPGEKPYKCPECGKSFSSPADLTRHQRTHTGEKPYKCPECGKSFSTSGHLVRHQRTHTGEKPYKCPECGKSFSDPGALVRHQRTHTGEKPYKCPECGKSFSTSGNLTEHQRTHTGKK TS (SEQ ID NO:14). The zinc finger nuclease, termed ZFN1VL, targets CDR1 in the variable region of the light chain. ZFN1VL comprises a targeting region comprising the nucleic acid sequence gctcaacgtctg (SEQ ID NO:15) and the zinc finger amino acid recognition sequence LEPGEKPYKCPECGKSFSRNDALTEHQRTHTGEKPYKCPECGKSFSSRRTCRAHQRTHTGEKPYKCPECGKSFSQSGNLTEHQRTHTGEKPYKCPECGKSFSTSGELVRHQRTHTGKKTS (SEQ ID NO:16). The zinc finger nuclease, termed ZFN2VL, targets CDR1 in the variable region of the light chain. ZFN2VL comprises a targeting region comprising the nucleic acid sequence aagagaggccca (SEQ ID NO:17) and the zinc finger amino acid recognition sequence LEPGEKPYKCPECGKSFSTSHSLTEHQRTHTGEKPYKCPECGKSFSDPGHLVRHQRTHTGEKPYKCPECGKSFSQLAHLRAHQRTHTGEKPYKCPECGKSFSRKDNLKNHQRTHTGKKTS (SEQ ID NO: 18). The zinc finger nuclease, termed ZFN3VL, targets CDR3 in the variable region of the light chain. ZFN3VL comprises a targeting region comprising the nucleic acid sequence gttgccgagcga (SEQ ID NO:19) and the zinc finger amino acid recognition sequence LEPGEKPYKCPECGKSFSQSGHLTEHQRTHTGEKPYKCPECGKSFSRSDNLVRHQRTHTGEKPYKCPECGKSFSDCRDLARHQRTHTGEKPYKCPECGKSFSTSGSLVRHQRTHTGKKTS (SEQ ID NO:20). The zinc finger nuclease, termed ZFN4VL, targets CDR3 in the variable region of the light chain. ZFN4VL comprises a targeting region comprising the nucleic acid sequence cgcatggttaag (SEQ ID NO:21) and the zinc finger amino acid recognition sequence LEPGEKPYKCPECGKSFSRKDNLKNHQRTHTGEKPYKCPECGKSFSTSGSLVRHQRTHTGEKPYKCPECGKSFSRRDELNVHQRTHTGEKPYKCPECGKSFSHTGHLLEHQRTHTGKKTS (SEQ ID NO:22). In the constructs of this Example, the lentiviral vector for zinc finger-nuclease targeting V$_H$ contained a puromycin resistance gene, and the lentiviral vector for zinc finger nuclease targeting V$_L$ contained a neomycin resistance gene, as well as an IRES sequence.

All patents, patent applications and publications referred to or cited herein are hereby incorporated by reference in their entireties for all purposes.

It is understood that the embodiments and examples described herein are for illustrative purposes and that various modifications or changes in light thereof will be suggested to persons skilled in the pertinent art and are to be included within the spirit and purview of this application and scope of the appended claims.

The invention claimed is:

1. A method of selecting a binding molecule which blocks or disrupts an interaction between a cell surface expressed receptor protein and its cognate ligand within a cell, comprising:
   (a) expressing in the cell a receptor protein which is expressible on the surface of the cell;
   (b) expressing in the cell a cognate ligand of the receptor protein, said cognate ligand being molecularly tagged with a peptide for retaining the ligand in an intracellular organelle under conditions allowing for the retention of the ligand in the organelle and the interaction of the receptor protein and the cognate ligand in the organelle; wherein the intracellular organelle is selected from the group consisting of endoplasmic reticulum (ER), Golgi, cellular plasma membrane; mitochondrion; nucleus; and peroxisome;
   (c) introducing into the cell a binding molecule, or a binding fragment or portion thereof, which specifically binds either the receptor protein or the ligand protein retained in the intracellular organelle; and
   (d) detecting the level of the receptor protein expressed on the cell surface;
   wherein, if the binding molecule, or a binding fragment or portion thereof, binds to either the receptor protein or the ligand and blocks or disrupts their interaction in the organelle, the receptor protein is expressed and detectable on the cell surface, and wherein the binding molecule, or a binding fragment or portion thereof, which blocks or disrupts the receptor protein and ligand interaction is selectable.

2. The method according to claim 1, further comprising recovering or isolating the selected binding molecule, or a binding fragment or portion thereof, from the cell.

3. The method according to claim 1, wherein the binding molecule, or a binding fragment or portion thereof, is selected from an antibody, or a binding fragment or portion thereof, a genetically diversified antibody, or a binding fragment or portion thereof, a member of an antibody library, or a binding fragment or portion thereof, a member of a genetically diversified antibody library, or a binding fragment or portion thereof, a single domain antibody, a member of a single domain antibody library, a member of a genetically diversified single domain antibody library, a $V_H$ domain, a genetically diversified $V_H$ domain, a $V_L$ domain, or a genetically diversified $V_L$ domain, or a complementarity determining region (CDR).

4. The method according to claim 1, wherein the binding molecule binds to the receptor protein or to the cognate ligand.

5. The method according to claim 1, wherein the cognate ligand is molecularly tagged with a peptide for retaining the ligand in the endoplasmic reticulum (ER).

6. The method according to claim 5, wherein the ER retention sequence is set forth in SEQ ID NO: 1.

7. The method according claim 3, wherein the antibody, or a binding fragment or portion thereof, is selected from a Fab fragment, a Fab' fragment, a F(ab')2 fragment, an Fd fragment, an Fv fragment, a single-chain variable fragment (scFv), a diabody, or a domain antibody (dAb).

8. The method according to 3, wherein the antibody binding fragment or portion thereof is selected from
   (i) a $V_L$ domain or a genetically diversified $V_L$ domain; or
   (ii) a $V_H$ domain or a genetically diversified $V_H$ domain.

9. The method according to claim 1, wherein the binding molecule is a non-antibody molecule.

10. The method according to claim 1, wherein the binding molecule binds (i) to the receptor protein, or (ii) to the cognate ligand.

11. The method according to claim 1, wherein the cognate ligand is molecularly tagged with a peptide for retaining the ligand in the Golgi and wherein the Golgi retention signal peptide sequence is set forth in SEQ ID NO: 2.

12. A method of detecting whether a binding molecule, or a binding fragment or portion thereof, specifically binds to a cell surface expressed target protein within a cell, comprising:
   (a) expressing in a cell a target protein which is expressible on the surface of the cell;
   (b) expressing in the cell the binding molecule, or a binding fragment or portion thereof, fused to a sequence for retaining the binding molecule in an intracellular organelle selected from the group consisting of endoplasmic reticulum (ER), Golgi, cellular plasma membrane; mitochondrion; nucleus; and peroxisome;
   wherein, if the binding molecule, or a binding fragment or portion thereof, specifically binds to the target protein in the cell, the target protein is retained in the intracellular organelle bound to the binding molecule, or the binding fragment or portion thereof, thereby preventing expression of the target protein on the cell surface; and
   (c) detecting the level of the target protein expressed on the cell surface, such that a non-detectable or low level of the target protein detected on the cell surface indicates binding of the binding protein, or a binding fragment or portion thereof, to the target molecule in the cell.

13. The method according to claim 12, wherein the binding molecule, or a binding fragment or portion thereof, is molecularly tagged with a peptide for retaining the ligand in the endoplasmic reticulum (ER).

14. The method according to claim 13, wherein the ER retention sequence is set forth in SEQ ID NO: 1.

15. The method according to claim 12, further comprising recovering or isolating the binding molecule, or a binding fragment or portion thereof, from the cell.

16. The method according to claim 12, wherein the binding molecule, or a binding fragment or portion thereof, is selected from an antibody, or a binding fragment or portion thereof, a genetically diversified antibody, or a binding fragment or portion thereof, a member of an antibody library, or a binding fragment or portion thereof, a member of a genetically diversified antibody library, or a binding fragment or portion thereof, a single domain antibody, a member of a single domain antibody library, a member of a genetically diversified single domain antibody library, a $V_H$ domain, a genetically diversified $V_H$ domain, a $V_L$ domain, or a genetically diversified $V_L$ domain, or a complementarity determining region (CDR).

17. The method according to claim 16, wherein the antibody, or a binding fragment or portion thereof, is selected from a Fab fragment, a Fab' fragment, a F(ab')2 fragment, an Fd fragment, an Fv fragment, a single-chain variable fragment (scFv), a diabody, or a domain antibody (dAb).

18. The method according to 12, wherein the antibody binding fragment or portion thereof is selected from
   (i) a $V_L$ domain or a genetically diversified $V_L$ domain; or
   (ii) a $V_H$ domain or a genetically diversified $V_H$ domain.

19. A method of selecting for an antibody, or a binding fragment or portion thereof, that specifically binds to a target protein expressed on the surface of a cell, comprising:

(a) expressing the target protein on the surface of cells in a cell line, wherein the cell surface-expressed target protein is detectable by a detectably labeled binding molecule, an antibody or a binding fragment or portion thereof, for selection for binding to the target protein, wherein the antibody, or a binding fragment or portion thereof, is fused to a signal peptide for retaining the antibody or a binding fragment or portion thereof in an intracellular organelle under conditions allowing for the interaction and binding of the antibody, or a binding fragment or portion thereof, and the target protein within the organelle; wherein the intracellular organelle is selected from the group consisting of endoplasmic reticulum (ER), Golgi, cellular plasma membrane; mitochondrion; nucleus; and peroxisome; and (b) detecting the level of the target protein expressed on the cell surface with the detectably labeled binding molecule;

wherein, if the antibody, or a binding fragment or portion thereof, specifically binds to the target protein in the organelle, the target protein is bindably retained therein, thereby decreasing or eliminating the level of expression of the target protein on the cell surface; and indicating the retention of a selectable antibody, or a binding fragment thereof, in the cell.

20. The method according to claim 19, further comprising: recovering from the cells the antibody, or a binding fragment or portion thereof, that specifically binds to the target protein.

21. The method according to claim 19, wherein the antibody or a binding fragment or portion thereof is fused to a signal peptide for retaining the antibody, or a binding fragment or portion thereof, in the endoplasmic reticulum (ER) intracellular organelle.

22. The method according to claim 21, wherein the sequence encoding the peptide for retaining the antibody, or a binding fragment or portion thereof, in the ER is set forth in SEQ ID NO:1.

23. The method according to claim 19, wherein the antibody or a binding fragment or portion thereof is fused to a signal peptide for retaining the antibody, or a binding fragment or portion thereof, in the Golgi intracellular organelle.

24. The method according to claim 23, wherein the sequence encoding the peptide for retaining the antibody, or a binding fragment or portion thereof, in the Golgi is set forth in SEQ ID NO:2.

25. The method according to claim 19, wherein the target protein is a receptor protein or a membrane-expressible ligand protein.

26. The method according to claim 19, wherein the antibody or a binding fragment or portion thereof is selected from a member of an antibody library, a member of a genetically diversified antibody library, a member of an antibody single domain library, a member of a genetically diversified antibody single domain library; an antibody $V_L$ domain; a genetically diversified antibody $V_L$ domain; an antibody $V_H$ domain; or a genetically diversified antibody $V_H$ domain; a polyclonal antibody, a monoclonal antibody, a chimeric antibody, a humanized antibody and a fully human antibody.

27. The method according to claim 19, wherein the antibody, or a binding fragment or portion thereof, is selected from a Fab fragment, a Fab' fragment, a F(ab')2 fragment, an Fd fragment, an Fv fragment, a single-chain variable fragment (scFv), a diabody, or a domain antibody (dAb).

28. The method according to claim 19, wherein the level of the target protein expressed on the cell surface is detected by flow cytometry and a detectably labeled antibody.

29. A method of selecting from a plurality of binding molecules a binding molecule which binds a target antigen that is a member of an interacting pair comprising a cell surface-expressed receptor binding protein and a cognate ligand, the method comprising:

(a) introducing a nucleic acid molecule encoding one of a plurality of binding molecules into cells expressing the receptor binding protein and the cognate ligand, wherein the cognate ligand is fused to a retention signal peptide that retains the cognate ligand in an intracellular organelle selected from the group consisting of endoplasmic reticulum (ER), Golgi, cellular plasma membrane; mitochondrion; nucleus; and peroxisome;

(b) expressing in the cells the nucleic acid molecule of (a), wherein an expressed binding molecule binds to the receptor binding protein or to the cognate ligand target antigen retained in the organelle and disrupts or blocks the interaction between the receptor binding protein and the cognate ligand; and (c) detecting the level of receptor binding protein expressed on the cell surface; wherein, if the binding molecule binds to either the receptor binding protein or to the cognate ligand in the organelle and disrupts or blocks their interaction, the receptor binding protein is expressed and detectable on the cell surface, and wherein the binding molecule that disrupts or blocks the interaction is selectable.

30. The method according to claim 29, wherein the plurality of binding molecules is selected from one or more of:

(i) an antibody $V_L$ library or a genetically diversified $V_L$ library; or (ii) an antibody $V_H$ library or a genetically diversified $V_H$ library.

31. The method according to claim 29, further comprising recovering or isolating the selectable binding molecule from the cell.

32. The method according to claim 29, wherein the plurality of binding molecules is selected from an antibody library, a genetically diversified antibody library, a single domain antibody library, a genetically diversified single domain antibody library, a $V_L$ domain library, a genetically diversified $V_L$ domain library, a $V_H$ domain library, or a genetically diversified $V_H$ domain library.

33. The method according to claim 29, wherein the binding molecule is an antibody or a binding fragment or portion thereof.

34. The method according to claim 33, wherein the antibody binding fragment or portion is selected from a Fab fragment, a Fab' fragment, a F(ab')2 fragment, an Fd fragment, an Fv fragment, a single-chain variable fragment (scFv), a diabody, a domain antibody (dAb), a heavy chain variable domain ($V_H$), a genetically diversified heavy chain variable domain ($V_H$), a light chain variable domain ($V_L$), a genetically diversified light chain variable domain ($V_L$), or a complementarity determining region (CDR).

35. The method according to claim 33, wherein the antibody binding fragment or portion is selected from a $V_L$ domain; a genetically diversified $V_L$ domain; a $V_H$ domain; or a genetically diversified $V_H$ domain.

36. The method according to claim 29, wherein the intracellular organelle is the endoplasmic reticulum (ER)

and the cognate ligand is molecularly tagged with an ER retention peptide having the sequence as set forth in SEQ ID NO: 1.

37. The method according to claim 29, wherein the intracellular organelle is the Golgi and the cognate ligand is molecularly tagged with an Golgi retention peptide having the sequence as set forth in SEQ ID NO: 2.

38. A method of selecting from a plurality of binding molecules, a binding molecule, or a binding portion thereof, that binds a cell surface expressed target protein, comprising:
   (a) introducing into cells a nucleic acid molecule encoding one of a plurality of binding molecules and operably linked to a nucleic acid molecule encoding a intracellular organelle retention signal peptide, wherein the cells express the target protein which is expressible on the cell surface;
   (b) expressing in the cells one of the plurality of binding molecules comprising the retention signal peptide; wherein, if one of the plurality of binding molecules comprises a binding molecule, or a binding portion thereof, that specifically binds to the target protein, the target protein is retained in the cell organelle through its being bound to the binding molecule, or a binding portion thereof, which is retained in the intracellular organelle, thereby preventing both exit of the target protein from the organelle and expression of the target protein on the cell surface; and
   (c) detecting the level of the target protein expressed on the cell surface, such that a non-detectable or low level of the target protein detected on the cell surface indicates specific binding of the binding molecule, or the binding portion thereof, to the target molecule in the cell, wherein the binding molecule, or the binding portion thereof, is selectable from the cells.

39. The method according to claim 38, wherein the nucleic acid molecule encoding one of a plurality of binding molecules is introduced into the cells by lentivirus particles harboring the nucleic acid molecule.

40. The method according to claim 38, further comprising recovering or isolating the selected binding molecule from the cell.

41. The method according to claim 38, wherein the plurality of binding molecules is selected from an antibody library, a genetically diversified antibody library, a single domain antibody library, a genetically diversified single domain antibody library, a $V_L$ domain library, a genetically diversified $V_L$ domain library, a $V_H$ domain library, or a genetically diversified $V_H$ domain library.

42. The method according to claim 41, wherein the plurality of binding molecules is selected from one or more of:
   (i) an antibody $V_L$ library or a genetically diversified $V_L$ library; or
   (ii) an antibody $V_H$ library or a genetically diversified $V_H$ library.

43. The method according to claim 38, wherein the binding molecule or a binding portion thereof is an antibody or a binding fragment or portion thereof.

44. The method according to 198, wherein the antibody binding fragment or portion is selected from a Fab fragment, a Fab' fragment, a F(ab')2 fragment, an Fd fragment, an Fv fragment, a single-chain variable fragment (scFv), a diabody, a domain antibody (dAb), a heavy chain variable domain ($V_H$), a genetically diversified heavy chain variable domain ($V_H$), a light chain variable domain ($V_L$), a genetically diversified light chain variable domain ($V_L$), or a complementarity determining region (CDR).

45. The method according to claim 38, wherein the binding molecule, or a binding portion thereof, is selected from one or more of:
   (i) a $V_L$ domain or a genetically diversified $V_L$ domain; or
   (ii) a $V_H$ domain or a genetically diversified $V_H$ domain.

46. The method according to claim 38, wherein the intracellular organelle retention signal peptide is the ER signal peptide having the sequence set forth in SEQ ID NO: 1 or the Golgi signal peptide having the sequence set forth in SEQ ID NO: 2.

47. A method of preventing or knocking down cell surface expression of a ligand-binding receptor protein, comprising:
   (a) expressing in a cell the ligand-binding receptor protein;
   (b) expressing in the cell a ligand protein capable of being bound by the ligand-binding receptor protein, wherein the ligand protein is fused to exogenous signal peptide for retaining the ligand protein in an intracellular organelle, under conditions permitting the interaction of the ligand-binding receptor protein and the ligand protein in the organelle wherein the intracellular organelle is selected from the group consisting of endoplasmic reticulum (ER), Golgi, cellular plasma membrane; mitochondrion; nucleus; and peroxisome;
   (c) measuring the level of the ligand-binding receptor protein expressed on the cell surface; wherein the binding of the ligand-binding receptor protein to the ligand protein retained in the organelle concomitantly retains the ligand-binding receptor protein bound to the ligand protein in the organelle, thereby preventing or knocking down the cell surface expression of the ligand-binding receptor protein.

48. A method of selecting from a plurality of binding molecules a binding molecule which binds a target antigen that is a member of an interacting pair comprising a cell surface-expressed receptor binding protein and a cognate ligand, the method comprising:
   (a) co-expressing in a single cell which expresses the receptor binding protein
      (i) a nucleic acid molecule encoding one of a plurality of binding molecules, and
      (ii) a nucleic acid molecule encoding a cognate ligand of the receptor binding protein,
   wherein either the nucleic acid molecule encoding the binding molecule or the nucleic acid molecule encoding the cognate ligand is operably coupled to a nucleic acid molecule encoding a retention signal peptide for retaining either (i) or (ii) in an intracellular organelle following expression of (i) or (ii) in the cell; under conditions allowing for retention of the expressed binding molecule or the expressed cognate ligand in the intracellular organelle;
   wherein the intracellular organelle is selected from the group consisting of endoplasmic reticulum (ER), Golgi, cellular plasma membrane; mitochondrion; nucleus; and peroxisome and wherein, if an expressed binding molecule binds to the receptor binding protein or the cognate ligand as target antigen, such binding disrupts, neutralizes, or blocks the natural interaction between the receptor binding protein and the cognate ligand and releases the receptor binding protein from its interaction with the cognate ligand for expression of the receptor binding protein on the cell surface; and
   (b) detecting the level of receptor binding protein expressed on the cell surface such that a high level of receptor binding protein expression of the cell surface indicates the expression and selection of a binding molecule which binds a target antigen within the cell.

49. The method according to claim 48, wherein the plurality of binding molecules is selected from an antibody library, a genetically diversified antibody library, a single domain antibody library, a genetically diversified single domain antibody library, a $V_L$ domain library, a genetically diversified $V_L$ domain library, a $V_H$ domain library, or a genetically diversified $V_H$ domain library.

50. The method according to claim 48, wherein the binding molecule is an antibody or a binding fragment or portion thereof.

51. The method according to 50, wherein the antibody or a binding fragment or portion thereof is selected from a Fab fragment, a Fab' fragment, a F(ab')2 fragment, an Fd fragment, an Fv fragment, a single-chain variable fragment (scFv), a diabody, a domain antibody (dAb), a heavy chain variable domain ($V_H$), a genetically diversified heavy chain variable domain ($V_H$), a light chain variable domain ($V_L$), a genetically diversified light chain variable domain ($V_L$), or a complementarity determining region (CDR).

52. The method according to 48, wherein the binding molecule is selected from one or more of:
(i) a $V_L$ domain or a genetically diversified $V_L$ domain; or
(ii) a $V_H$ domain or a genetically diversified $V_H$ domain.

53. The method according to claim 48, wherein the intracellular organelle is the endoplasmic reticulum (ER) and the cognate ligand is molecularly tagged with an ER retention peptide having the sequence as set forth in SEQ ID NO: 1.

54. The method according to claim 48, wherein the intracellular organelle is the Golgi and the cognate ligand is molecularly tagged with an Golgi retention peptide having the sequence as set forth in SEQ ID NO: 2.

55. The method according to claim 48, wherein the target antigen is selected from growth factor receptors, hormone receptors, enzyme receptors, Fc receptors, neurotransmitter receptors, chemokine receptors, cytokine receptors, lymphokine receptors, interleukin receptors, tumor antigen receptors, cell recognition or stimulatory receptors, receptors in receptor families selected from apolipoprotein receptors, EGFR, ErbB-1R, HER1, HER2, aFGFR, bFGFR, NGFR, VEGFR, FltR, TGFR, TGFR-α-1, TGFR-β, TNFR-α, BDNFR, insulin receptor, insulin-like growth factor receptor (IGFR), PDGFR, HGFR, TRKR, BDNFR, CNTFR, GMFR, NT3R, NT5R, HARPR/pleiotrophinR, TIE receptors, Eph receptors, DDR receptors, ROR receptors, LTK receptors, AXL receptors, RET receptors, or TOLL-like receptors; steroid hormone receptors, thyroid hormone receptors, melatonin receptors, adrenergic receptors; receptors for peptides selected from amylin, angiotensinogen, angiotensin, atrial natriuretic peptide, brain natriuretic peptide, calcitonin, corticotropin, erythropoietin, endothelin, enkephalin, follicle stimulating hormone, gastrin, ghrelin, glucagon, human chorionic gonadotropin, inhibin, leptin, luteinizing hormone, melanocyte stimulating hormone, oxitocin, pancreatic polypeptide, parathyroid hormone, prolactin, prolactin releasing hormone, rennin, secretin, somatostatin, thrombopoietin, thyroid stimulating hormone, or thyrotropin releasing hormone; or GP130 or IL6 receptors.

56. The method according to claim 48, wherein the target antigen is selected from growth factors, hormones, enzymes, metabolic enzymes, neurotransmitters, chemokines, cytokines, lymphokines, interleukin, tumor antigens, tumor suppressor antigens, multidrug resistance proteins, coagulation factors, Factor VII, Factor VIII, Factor IX, trophic factors, cell recognition or stimulatory molecules, apolipoproteins, EGF, ErbB-1, HER1, HER2, aFGF, bFGF, NGF, VEGF, Flt, TGF, TGF-α-1, TGF-β, TNF-α, BDNF, insulin, insulin-like growth factor (IGFR), PDGF, HGF, TRK, BDNF, CNTF, GMF, NT3, NT5, HARP/pleiotrophin, TIE proteins, Eph proteins, DDR proteins, ROR proteins, LTK proteins, AXL proteins, RET proteins, TOLL-like proteins; hormones selected from steroid hormones, thyroid hormones, melatonin; adrenergic protein; peptides selected from amylin, angiotensinogen, angiotensin, atrial natriuretic peptide, brain natriuretic peptide, calcitonin, corticotropin, erythropoietin, endothelin, enkephalin, follicle stimulating hormone, gastrin, ghrelin, glucagon, human chorionic gonadotropin, inhibin, leptin, luteinizing hormone, melanocyte stimulating hormone, oxitocin, pancreatic polypeptide, parathyroid hormone, prolactin, prolactin releasing hormone, rennin, secretin, somatostatin, thrombopoietin, thyroid stimulating hormone, thyrotropin releasing hormone; GP130 or IL6.

* * * * *

SEQUENCE LISTING

```
<160> NUMBER OF SEQ ID NOS: 47

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Asp Glu Leu
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Gln Arg Leu
1
```

```
<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 3

Cys Ala Ala Xaa
1

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Ser Val Leu Thr Pro Leu Leu Leu Arg Gly Leu Thr Gly Ser Ala
1               5                   10                  15

Arg Arg Leu Pro Val Pro Arg Ala Lys
            20                  25

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Pro Lys Lys Lys Arg Lys Val
1               5

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(18)
<223> OTHER INFORMATION: a, c, t, g, unknown or other
<220> FEATURE:
<221> NAME/KEY: modified_base
<222> LOCATION: (24)..(35)
<223> OTHER INFORMATION: a, c, t, g, unknown or other

<400> SEQUENCE: 6
tactcannnn nnnnnnnnct gatnnnnnnn nnnnnttact ca                    42

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 7
gtcgaaaagc ca                                                              12

<210> SEQ ID NO 8
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Glu Pro Gly Glu Lys Pro Tyr Lys Cys Pro Glu Cys Gly Lys Ser
1               5                   10                  15

Phe Ser Thr Ser His Ser Leu Thr Glu His Gln Arg Thr His Thr Gly
            20                  25                  30

Glu Lys Pro Tyr Lys Cys Pro Glu Cys Gly Lys Ser Phe Ser Arg Lys
        35                  40                  45

Asp Asn Leu Lys Asn His Gln Arg Thr His Thr Gly Glu Lys Pro Tyr
    50                  55                  60

Lys Cys Pro Glu Cys Gly Lys Ser Phe Ser Gln Ser Ser Asn Leu Val
65                  70                  75                  80

Arg His Gln Arg Thr His Thr Gly Glu Lys Pro Tyr Lys Cys Pro Glu
                85                  90                  95

Cys Gly Lys Ser Phe Ser Asp Pro Gly Ala Leu Val Arg His Gln Arg
            100                 105                 110

Thr His Thr Gly Lys Lys Thr Ser
        115                 120

<210> SEQ ID NO 9
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caaaaatcga gct                                                             13

<210> SEQ ID NO 10
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Leu Glu Pro Gly Glu Lys Pro Tyr Lys Cys Pro Glu Cys Gly Lys Ser
1               5                   10                  15

Phe Ser Thr Ser Gly Glu Leu Val Arg His Gln Arg Thr His Thr Gly
            20                  25                  30

Glu Lys Pro Tyr Lys Cys Pro Glu Cys Gly Lys Ser Phe Ser Gln Ser
        35                  40                  45

Gly His Leu Thr Glu His Gln Arg Thr His Thr Gly Glu Lys Pro Tyr
    50                  55                  60

Lys Cys Pro Glu Cys Gly Lys Ser Phe Ser Thr Thr Gly Asn Leu Thr
65                  70                  75                  80
```

Val His Gln Arg Thr His Thr Gly Glu Lys Pro Tyr Lys Cys Pro Glu
            85                  90                  95

Cys Gly Lys Ser Phe Ser Gln Ser Gly Asn Leu Thr Glu His Gln Arg
            100                 105                 110

Thr His Thr Gly Lys Lys Thr Ser
            115                 120

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
actcagcgaa cg                                                          12

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Leu Glu Pro Gly Glu Lys Pro Tyr Lys Cys Pro Glu Cys Gly Lys Ser
1               5                   10                  15

Phe Ser Arg Thr Asp Thr Leu Arg Asp His Gln Arg Thr His Thr Gly
            20                  25                  30

Glu Lys Pro Tyr Lys Cys Pro Glu Cys Gly Lys Ser Phe Ser Gln Ser
        35                  40                  45

Gly His Leu Thr Glu His Gln Arg Thr His Thr Gly Glu Lys Pro Tyr
    50                  55                  60

Lys Cys Pro Glu Cys Gly Lys Ser Phe Ser Arg Ala Asp Asn Leu Thr
65                  70                  75                  80

Glu His Gln Arg Thr His Thr Gly Glu Lys Pro Tyr Lys Cys Pro Glu
            85                  90                  95

Cys Gly Lys Ser Phe Ser Thr His Leu Asp Leu Ile Arg His Gln Arg
            100                 105                 110

Thr His Thr Gly Lys Lys Thr Ser
            115                 120

<210> SEQ ID NO 13
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
caatgtcggt aca                                                         13

<210> SEQ ID NO 14
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Leu Glu Pro Gly Glu Lys Pro Tyr Lys Cys Pro Glu Cys Gly Lys Ser
1               5                   10                  15

Phe Ser Ser Pro Ala Asp Leu Thr Arg His Gln Arg Thr His Thr Gly
            20                  25                  30

Glu Lys Pro Tyr Lys Cys Pro Glu Cys Gly Lys Ser Phe Ser Thr Ser
        35                  40                  45

Gly His Leu Val Arg His Gln Arg Thr His Thr Gly Glu Lys Pro Tyr
    50                  55                  60

Lys Cys Pro Glu Cys Gly Lys Ser Phe Ser Asp Pro Gly Ala Leu Val
65                  70                  75                  80

Arg His Gln Arg Thr His Thr Gly Glu Lys Pro Tyr Lys Cys Pro Glu
                85                  90                  95

Cys Gly Lys Ser Phe Ser Thr Ser Gly Asn Leu Thr Glu His Gln Arg
            100                 105                 110

Thr His Thr Gly Lys Lys Thr Ser
        115                 120

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gctcaacgtc tg                                                        12

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Leu Glu Pro Gly Glu Lys Pro Tyr Lys Cys Pro Glu Cys Gly Lys Ser
1               5                   10                  15

Phe Ser Arg Asn Asp Ala Leu Thr Glu His Gln Arg Thr His Thr Gly
            20                  25                  30

Glu Lys Pro Tyr Lys Cys Pro Glu Cys Gly Lys Ser Phe Ser Ser Arg
        35                  40                  45

Arg Thr Cys Arg Ala His Gln Arg Thr His Thr Gly Glu Lys Pro Tyr
    50                  55                  60

Lys Cys Pro Glu Cys Gly Lys Ser Phe Ser Gln Ser Gly Asn Leu Thr
65                  70                  75                  80

Glu His Gln Arg Thr His Thr Gly Glu Lys Pro Tyr Lys Cys Pro Glu
                85                  90                  95

Cys Gly Lys Ser Phe Ser Thr Ser Gly Glu Leu Val Arg His Gln Arg
            100                 105                 110

Thr His Thr Gly Lys Lys Thr Ser
        115                 120

<210> SEQ ID NO 17
<211> LENGTH: 12
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 17
aagagaggcc ca                                                              12

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

| Leu | Glu | Pro | Gly | Glu | Lys | Pro | Tyr | Lys | Cys | Pro | Glu | Cys | Gly | Lys | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | Ser | Thr | Ser | His | Ser | Leu | Thr | Glu | His | Gln | Arg | Thr | His | Thr | Gly |
|     |     |     | 20  |     |     |     |     | 25  |     |     |     |     | 30  |     |     |

| Glu | Lys | Pro | Tyr | Lys | Cys | Pro | Glu | Cys | Gly | Lys | Ser | Phe | Ser | Asp | Pro |
|     |     | 35  |     |     |     |     | 40  |     |     |     |     | 45  |     |     |     |

| Gly | His | Leu | Val | Arg | His | Gln | Arg | Thr | His | Thr | Gly | Glu | Lys | Pro | Tyr |
| 50  |     |     |     |     | 55  |     |     |     |     | 60  |     |     |     |     |     |

| Lys | Cys | Pro | Glu | Cys | Gly | Lys | Ser | Phe | Ser | Gln | Leu | Ala | His | Leu | Arg |
| 65  |     |     |     |     | 70  |     |     |     |     | 75  |     |     |     |     | 80  |

| Ala | His | Gln | Arg | Thr | His | Thr | Gly | Glu | Lys | Pro | Tyr | Lys | Cys | Pro | Glu |
|     |     |     |     | 85  |     |     |     |     | 90  |     |     |     |     | 95  |     |

| Cys | Gly | Lys | Ser | Phe | Ser | Arg | Lys | Asp | Asn | Leu | Lys | Asn | His | Gln | Arg |
|     |     |     | 100 |     |     |     |     | 105 |     |     |     |     | 110 |     |     |

| Thr | His | Thr | Gly | Lys | Lys | Thr | Ser |
|     |     |     | 115 |     |     |     | 120 |

```
<210> SEQ ID NO 19
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gttgccgagc ga                                                              12

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20
```

| Leu | Glu | Pro | Gly | Glu | Lys | Pro | Tyr | Lys | Cys | Pro | Glu | Cys | Gly | Lys | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | Ser | Gln | Ser | Gly | His | Leu | Thr | Glu | His | Gln | Arg | Thr | His | Thr | Gly |
|     |     |     | 20  |     |     |     |     | 25  |     |     |     |     | 30  |     |     |

| Glu | Lys | Pro | Tyr | Lys | Cys | Pro | Glu | Cys | Gly | Lys | Ser | Phe | Ser | Arg | Ser |
|     |     | 35  |     |     |     |     | 40  |     |     |     |     | 45  |     |     |     |

| Asp | Asn | Leu | Val | Arg | His | Gln | Arg | Thr | His | Thr | Gly | Glu | Lys | Pro | Tyr |
| 50  |     |     |     |     | 55  |     |     |     |     | 60  |     |     |     |     |     |

```
Lys Cys Pro Glu Cys Gly Lys Ser Phe Ser Asp Cys Arg Asp Leu Ala
 65                  70                  75                  80

Arg His Gln Arg Thr His Thr Gly Glu Lys Pro Tyr Lys Cys Pro Glu
                 85                  90                  95

Cys Gly Lys Ser Phe Ser Thr Ser Gly Ser Leu Val Arg His Gln Arg
            100                 105                 110

Thr His Thr Gly Lys Lys Thr Ser
        115                 120

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cgcatggtta ag                                                              12

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Glu Pro Gly Glu Lys Pro Tyr Lys Cys Pro Glu Cys Gly Lys Ser
 1               5                  10                  15

Phe Ser Arg Lys Asp Asn Leu Lys Asn His Gln Arg Thr His Thr Gly
             20                  25                  30

Glu Lys Pro Tyr Lys Cys Pro Glu Cys Gly Lys Ser Phe Ser Thr Ser
         35                  40                  45

Gly Ser Leu Val Arg His Gln Arg Thr His Thr Gly Glu Lys Pro Tyr
     50                  55                  60

Lys Cys Pro Glu Cys Gly Lys Ser Phe Ser Arg Arg Asp Glu Leu Asn
 65                  70                  75                  80

Val His Gln Arg Thr His Thr Gly Glu Lys Pro Tyr Lys Cys Pro Glu
                 85                  90                  95

Cys Gly Lys Ser Phe Ser His Thr Gly His Leu Leu Glu His Gln Arg
            100                 105                 110

Thr His Thr Gly Lys Lys Thr Ser
        115                 120

<210> SEQ ID NO 23
<211> LENGTH: 21
<212> TYPE: PRT
<213> ORGANISM: Mus sp.

<400> SEQUENCE: 23

Met Glu Thr Asp Thr Leu Leu Leu Trp Val Leu Leu Leu Trp Val Pro
 1               5                  10                  15

Gly Ser Thr Gly Asp
             20

<210> SEQ ID NO 24
<211> LENGTH: 12
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 24
aaggatgagc tc                                                            12

<210> SEQ ID NO 25
<211> LENGTH: 92
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aaaggatcca tggagacaga cacactcctg ctatgggtac tgctgctctg ggttccaggt        60
tccactggtg acacggccca ggcggccgag ct                                      92

<210> SEQ ID NO 26
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ttaggggggg gggagggaga ggggcgctag cctaagaagc gtagtccgga acgtcgtacg        60
g                                                                        61

<210> SEQ ID NO 27
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gactacgctt cttaggctag cgcccctctc cctccccccc ccctaacgtt actggccgaa        60

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tttgaattcc tactggaaca ggtggtggcg                                         30

<210> SEQ ID NO 29
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ttaggggggg gggagggaga ggggcgctag cctagagctc atccttctcg ctagaagcgt        60
agtccggaac gtcgta                                                        76
```

```
<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gttggccgat tcattaatgc ag                                              22

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aatgaaacca tcgatagcag cac                                             23

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agcgcaacgc aattaatgtg ag                                              22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggtcatagcc cccttattag cg                                              22

<210> SEQ ID NO 34
<211> LENGTH: 99
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtgaccatta aatgcagcgg cggcggcagc shrshrshrs hrshrshrsh rshrshrshr     60
shrshragcg gcggcggcag ctggtatcag cagaaaccg                            99

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gctgccgccg ccgctgcatt taatggtcac ggtgcc                               36
```

```
<210> SEQ ID NO 36
<211> LENGTH: 99
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acctattatt gcagcggcgg cggcagcshr shrshrshrs hrshrshrsh rshrshrshr      60
shragcggcg gcggcagcgg cggcggcacc gaactggaa                            99

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gctgccgccg ccgctgcaat aataggtcgc cgcatccgc                            39

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gacgatatca tggagacaga cacactc                                         27

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tttgaattcc tactggctgt agactagctc                                      30

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gacacggccc aggcggcccc tgtagcccat gttgtagcaa ac                        42

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atggtgctgg ccggcctggc ccagggcaat gatccc                               36
```

```
<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctaggatcca tggacagcct cttgatgaac                                        30

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tttgctagct caaagtccca aagtacg                                           27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atggagacag acacactcct gctatgg                                           27

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtagtccgga acgtcgtacg ggta                                              24

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 46

His His His His His His
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Gly Glu Lys Pro
1               5
```